United States Patent
Joffre et al.

(10) Patent No.: US 10,806,691 B2
(45) Date of Patent: Oct. 20, 2020

(54) ORGANOPOLYSILOXANE, ACID-NEUTRALIZED SALT THEREOF, AND APPLICATIONS THEREOF

(71) Applicants: Dow Silicones Corporation, Midland, MI (US); Dow Corning Toray Co., Ltd., Tokyo (JP)

(72) Inventors: Eric Jude Joffre, Midland, MI (US); Lenin James Petroff, Bay City, MI (US); Seiki Tamura, Ichihara (JP)

(73) Assignees: DOW SILICONES CORPORATION, Midland, MI (US); DOW TORAY CO., LTD., Tokyo (JP)

( * ) Notice: Subject to any disclaimer, the term of this patent is extended or adjusted under 35 U.S.C. 154(b) by 59 days.

(21) Appl. No.: 16/096,195

(22) PCT Filed: Apr. 26, 2017

(86) PCT No.: PCT/JP2017/016527
§ 371 (c)(1),
(2) Date: Jan. 3, 2019

(87) PCT Pub. No.: WO2017/188309
PCT Pub. Date: Nov. 2, 2017

(65) Prior Publication Data
US 2019/0133920 A1  May 9, 2019

Related U.S. Application Data

(60) Provisional application No. 62/238,157, filed on Apr. 27, 2016.

(51) Int. Cl.
| | |
|---|---|
| *A61K 8/898* | (2006.01) |
| *C09K 3/00* | (2006.01) |
| *C08G 77/26* | (2006.01) |
| *C08L 83/08* | (2006.01) |
| *C08G 77/388* | (2006.01) |
| *C08G 77/18* | (2006.01) |
| *C08L 83/06* | (2006.01) |

(52) U.S. Cl.
CPC ............. *A61K 8/898* (2013.01); *C08G 77/26* (2013.01); *C08L 83/08* (2013.01); *C09K 3/00* (2013.01)

(58) Field of Classification Search
CPC ...... A61K 8/898; C08G 77/26; C08G 77/388; C08G 77/18; C08L 83/08; C08L 83/06; C09K 3/00
See application file for complete search history.

(56) References Cited

U.S. PATENT DOCUMENTS

| | | |
|---|---|---|
| 3,658,867 A | 4/1972 | Prokai |
| 4,895,964 A | 1/1990 | Margida |
| 5,124,466 A | 7/1992 | Azechi et al. |
| 5,635,163 A | 6/1997 | Hansenne |
| 5,891,977 A | 4/1999 | Dietz et al. |
| 6,197,876 B1 | 3/2001 | Policello et al. |
| 6,818,610 B2 | 11/2004 | Zhang et al. |
| 6,903,061 B2 | 6/2005 | Masschelein et al. |
| 7,217,777 B2 | 5/2007 | Lange et al. |
| 8,784,787 B2 | 7/2014 | Tamura et al. |
| 9,580,600 B2 | 2/2017 | Tamura et al. |
| 9,783,643 B2 | 10/2017 | Hori et al. |
| 10,174,170 B2 * | 1/2019 | Maeshima ............... A61Q 1/02 |
| 2009/0176893 A1 | 7/2009 | Leatherman et al. |
| 2014/0135408 A1 | 5/2014 | Wang et al. |
| 2017/0218130 A1 | 8/2017 | Maeshima et al. |

FOREIGN PATENT DOCUMENTS

| | | |
|---|---|---|
| CN | 102504260 A | 6/2012 |
| EP | 0535596 A1 | 9/1992 |
| JP | S49011760 | 3/1974 |

(Continued)

OTHER PUBLICATIONS

The Cosmetic, Toiletry, and Fragrance Association, International Cosmetic Ingredient Dictionary and Handbook, 2002 Ninth Edition, vol. 1, Monographs A-L, p. 469.

International Search Report for related PCT Application No. PCT/JP2017/016527 dated May 30, 2017, 2 pages.

English language abstract and machine assisted translation for WO2015162906A1 extracted from https://worldwide.espacenet.com on Jan. 22, 2019, 138 pages.

English language abstract and machine assisted translation for JPH05112423A extracted from https://worldwide.espacenet.com on Jan. 22, 2019, 21 pages.

Tseng, Wei-Tsu et al., "Novel Polymeric Surfactants for Improving Chemical Mechanical Polishing Performance of Silicon Oxide", Electrochemical and Solid-State Letters., vol. 4, No. 5, Jan. 1, 2001, p. G42.

Sun, Hai Feng et al., "Synthesis and characterization of α-{3-[2-hydroxy-3-(N-methyl-N-hydroxy-ethylamino)propoxy]propyl}-ω-butylpolydimethylsiloxanes", Chinese Chemical Letters, Elsevier, Amsterdam, NL, vol. 19, No. 10, Oct. 1, 2008, pp. 1196-1198.

(Continued)

*Primary Examiner* — Jeffrey T. Palenik
(74) *Attorney, Agent, or Firm* — Warner Norcross + Judd LLP

(57) ABSTRACT

A silicone material is provided. The silicone material is an organopolysiloxane or acid-neutralized salt thereof that contains a side-chain bonded hydrophilic group having a tertiary-amine structure and represented by the general formula:

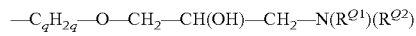

$$-C_qH_{2q}-O-CH_2-CH(OH)-CH_2-N(R^{Q1})(R^{Q2})$$

wherein q is a number ranging from 1 to 6, and wherein each of $R^{Q1}$ and $R^{Q2}$ is independently a halogen-substituted or non-substituted monovalent hydrocarbon group or an alkanol group. At least one of $R^{Q1}$ and $R^{Q2}$ has a hydroxyl group, provided the total number of hydroxyl groups in $R^{Q1}$ and $R^{Q2}$ is at most three (3). Any of $R^{Q1}$ and $R^{Q2}$ does not have a nitrogen atom in the group. The silicone material has a number of beneficial properties.

16 Claims, No Drawings

(56) References Cited

FOREIGN PATENT DOCUMENTS

| | | |
|---|---|---|
| JP | H0247138 A | 2/1990 |
| JP | H02157285 A | 6/1990 |
| JP | H05112423 A1 | 7/1993 |
| JP | H05238910 A | 9/1993 |
| JP | H07506596 A | 7/1995 |
| JP | H10330489 A | 12/1998 |
| JP | 2002537459 A | 11/2002 |
| JP | 2004505145 A | 2/2004 |
| JP | 2005513278 A | 5/2005 |
| JP | 2005520058 A | 7/2005 |
| JP | 2014505067 A | 2/2014 |
| JP | 5809849 B2 | 9/2015 |
| WO | 2003002635 A1 | 1/2003 |
| WO | 2011049247 A1 | 4/2011 |
| WO | 2011049248 A1 | 4/2011 |
| WO | 2011136397 A1 | 11/2011 |
| WO | 2012015069 A1 | 2/2012 |
| WO | 2012015070 A1 | 2/2012 |
| WO | 2012165227 A1 | 6/2012 |
| WO | 2013100176 A2 | 7/2013 |
| WO | 2013100207 A1 | 7/2013 |
| WO | 2013103147 A1 | 11/2013 |
| WO | 2014121037 A1 | 9/2014 |
| WO | 2014200111 A1 | 12/2014 |
| WO | 2015162906 A1 | 10/2015 |

OTHER PUBLICATIONS

Naghash, Hamid Javaherian et al., "Synthesis and characterization of a Nonionic Copolymeric Surfactant Based on a Monotelechelic Polydimethylsiloxane and Oxypropylated Acrylate Ester", Synthesis and Reactivity in Inorganic, Metal-Oragnic Nano-Metal Chemistry, vol. 44, No. 4, Apr. 21, 2014, p. 514-522.

English language abstract and machine assisted translation for JP5809849B2 extracted from https://worldwide.espacenet.com on Dec. 10, 2018, 128 pages.

English language abstract and machine assisted translation for WO2003002635 extracted from https://worldwide.espacenet.com on Dec. 10, 2018, 24 pages.

English language abstract and machine assisted translation for CN102504260 extracted from https://worldwide.espacenet.com on Dec. 10, 2018, 11 pages.

International Cosmetic Ingredient Dictionary and Handbook, 2002 Ninth Edition, vol. 1, Monographs A-L, p. 469.

* cited by examiner

ORGANOPOLYSILOXANE, ACID-NEUTRALIZED SALT THEREOF, AND APPLICATIONS THEREOF

CROSS-REFERENCE TO RELATED APPLICATIONS

This application is the National Stage of International Application No. PCT/JP2017/016527 filed on 26 Apr. 2017, which claims priority to and all advantages of U.S. Patent Appl. No. 62/328,157 filed on 27 Apr. 2016, the content of which is hereby incorporated by reference.

TECHNICAL FIELD

The present invention relates to a novel organopolysiloxane having a hydrophilic group containing a specific tertiary-amine structure only in a side chain of a siloxane molecular chain and having no other nitrogen atom, polyoxyalkylene structure, or reactive structure to radical polymerization, or acid-neutralized salt thereof. The present invention further relates to use (applications) of the novel organopolysiloxane or the like as a surfactant or a dispersant, an oil agent, a thickening agent, or a cosmetic raw material, and also relates to a composition including the novel organopolysiloxane or the like, in particular, a cosmetic or a preparation for external use. The present invention further relates to a method for producing the novel organopolysiloxane and the like.

In particular, the present invention relates to a novel organopolysiloxane that has two ionic properties and acid-neutralized salt thereof, unlike conventional non-ionic hydrophilic silicones such as polyether modified silicone, sugar modified silicone, and glycerin modified silicone. The novel organopolysiloxane and acid-neutralized salt thereof enables ionic management suitable for a purpose of a user, which is difficult with conventional non-ionic hydrophilic silicones. In a nutshell, the novel organopolysiloxane according to the present invention when not neutralized has a non-ionic property, dissolves in various types of hydrophobic oil agents (such as non-polar hydrocarbon oil, low-polar silicone oil, and polar oil containing ester group and the like), and thus can be stably compounded in an oil phase or an oil-water interface, whereas when neutralized with an acid, has a cationic property, has dramatically improved solubility in various types of polar solvents and water, and thus can be stably compounded in an aqueous phase containing the solvents or water.

In addition, the present invention relates to a novel organopolysiloxane or acid-neutralized salt thereof that are advantageous in that they have no polyoxyethylene group or active hydrogen-containing amino group in their structures, thus comply with a global trend of refining the entire structure of end consumer products, such as cosmetics, to have PEG-free formulations and satisfy safety-oriented market needs, and unlike conventionally known silicones with PEG-free formulations, enable good viscosity management at comparatively low viscosity and good compatibility with an oil agent, and can be designed into emulsion compositions with higher viscosity and stability than those of polyether modified silicones, when used with water.

BACKGROUND ART

Silicone chains are hydrophobic in nature. In view of this, conventionally, silicones have generally been stably compounded in the aqueous phase in the following manner: emulsification in water using a dedicated emulsifier with a surfactant used in combination; or combination of a large amount of hydrophilic groups (such as polyether chains, sugar chains, and (poly) glycerin chains) to molecular chains of silicone to strengthen molecular hydrophilicity. The former scenario is limited in terms of device, cumbersomeness, and selection of the surfactant, and thus is not convenient for a cosmetic design engineer to formulate silicones as desired. In the latter scenario, silicones cannot be efficiently hydrophilized because the hydrophilic groups are non-ionic. Furthermore, a large amount of hydrophilic groups combined to satisfy the requirements for compounding into the aqueous phase leads to a basic dilemma in terms of molecular design, that is, the silicone texture and waterproofness might be lost, or the silicone would have extremely high viscosity to be difficult to handle.

A number of alternatives have been known including: a compound obtained by grafting or combining quaternary ammonium cations or a quaternary ammonium salt structure to molecular chains of silicone; and a compound obtained by grafting or combining an amphoteric or anionic structure to molecular chains of silicone. These compounds can be stably compounded into water or a polar solvent due to their high ionicity (polarity), but lose waterproofness, do not dissolve in a hydrophobic oil agent (non-polar hydrocarbon oil, low-polar silicone oil, or polar oil including ester groups or the like), and cannot be formulated in an oil phase. Many of the ionic groups in such compounds are invariable, and thus are difficult to be converted to be non-ionic upon use.

Recently, there has been an increasing market demand for PEG-free (non-polyoxyethylene) products. For example, in Germany, a consumer information magazine has conducted a research on products including polyoxyethylene (PEG), and has reported a negative view in terms of safety. As a result, there has been an increasing demand for replacing a raw material including polyether groups into a non-polyether raw material. In Korea, non-polyether-based silicone surfactants have been attracting attention due to a concern that polyoxyethylene (PEG) produces formalin as a result of oxidative deterioration, and thus a product including PEG may be stimulating to the skin.

The inventors of the present invention have focused on a sugar derivative group and a glycerin derivative group as non-polyether hydrophilic groups, to study and evaluate characteristics of silicone compounds modified by these groups as well as a manufacturing process of these and the like (see Patent Documents 1 to 8, and 23). As the characteristics, the inventors have most heavily focused on emulsification performance for a water-in-oil emulsion, because the goal is to replace the existing polyether modified silicones without compromising the performance. In any of the cases, an emulsifier with an excellent performance was able to be manufactured through optimization of a chemical structure and a production process. Still, a task that a cost of a hydrophilic raw material for silicone modification is high has remained to be solved.

A tertiary-amine structure-containing polyhydric alcohol modified silicone, as reported in Patent Documents 9 to 21 for example, has been known as a hydrophilic silicone. It is to be noted that the compounds explicitly described in Examples of these documents are trisiloxane modified silicones, silicones having the modified portion at one terminal or both terminals, and copolymers to which silicone portions and modified portions are alternately bonded. Thus, no polysiloxane (with an average polymerization degree of siloxane portions being four or more) with a side chain having the modified portion has been reported. As described in Non-Patent Document 1, a polysiloxane combining portion with a side chain having both the modified portion and a poly(oxyethylene-oxypropylene) chain has been commercially available as DEA PG-PROPYL PEG/PPG-18/21 DIMETHICONE (INCI name). Patent Document 22 discloses a polysiloxane compound (Examples) with a side chain having both the modified portion derived from a secondary amine functional sugar derivative and a poly (oxyethylene-oxypropylene) chain, as well as a polysiloxane compound (Comparative Examples) with a side chain having only the modified portion derived from a secondary amine functional sugar derivative.

The inventors have investigated Patent Documents 9 to 21, and found out that no polymer having an organopolysiloxane chain as a main chain and tertiary-amine structure-containing polyhydric alcohol modified group as a side chain has been known, and thus its nature is unknown. The compound described in Non-Patent Document 1 and a compound according to Example in Patent Document 22 cannot satisfy the recent market demand for PEG-free (non-polyoxyethylene) products. A compound according to Comparative Example in Patent Document 21 has extremely high viscosity or is in a solid form, and thus has poor compatibility with other materials and is difficult to handle. Patent Document 21 discloses no organopolysiloxane with only a side chain (organopolysiloxane chain) having tertiary-amine structure-containing polyhydric alcohol modified group, and its effectiveness is not described or indicated in any part of the document.

It has been extremely difficult to obtain a truly high purity hydrophilic silicone compound including no residual hydrophilic modifier and the like with conventionally disclosed techniques, not only in a case with a polyether modified silicone but also in a case with any other conventionally known useful hydrophilic silicones. It is believed that this goal has not been substantially accomplished at least on a commercial scale.

In any cases, no PEG-free hydrophilic silicone material has been known that can be manufactured as a cosmetics material at a much lower cost than that manufactured with the techniques according to Patent Documents 1 to 8, while having a performance value equivalent or superior to that of a polyether modified silicone.

PRIOR ART DOCUMENTS

Patent Documents

Patent Document 1: WO 2011/049248
Patent Document 2: WO 2012/015070
Patent Document 3: WO 2013/100176
Patent Document 4: WO 2013/103147
Patent Document 5: WO 2014/200111
Patent Document 6: WO 2011/136397
Patent Document 7: WO 2012/015069
Patent Document 8: WO 2012/165227
Patent Document 9: JP S49-011760 B
Patent Document 10: JP H02-157285 A
Patent Document 11: JP H05-238910 A
Patent Document 12: JP H07-506596 A
Patent Document 13: JP 2002-537459 A
Patent Document 14: JP 2004-505145 A
Patent Document 15: JP 2005-513278 A
Patent Document 16: WO 2003/002635
Patent Document 17: JP 2005-520058 A
Patent Document 18: US Patent Publication No. 2009/0176893
Patent Document 19: JP 2014-505067 A
Patent Document 20: Chinese Patent Publication No. 102504260
Patent Document 21: WO 2014/121037
Patent Document 22: JP H10-330489
Patent Document 23: WO 2011/049247
Patent Document 24: WO 2013/100207

Non-Patent Document

Non-Patent Document 1: International Cosmetic Ingredient Dictionary and Handbook, 2002 Ninth Edition, Volume 1, Monographs A-L, page 469

SUMMARY OF THE INVENTION

Problems to be Solved by the Invention

As described above, no PEG-free hydrophilic silicone material has been known that has performance equivalent or superior to those of conventionally known non-ionic silicones and can be produced at a low cost. The goal cannot be accomplished with conventionally known tertiary-amine structure-containing polyhydric alcohol modified silicones.

The inventors of the present application have found a further problem to be solved. Conventionally known non-ionic silicones have an invariable ionicity, and thus non-ionic silicones supplied to the users can be designed in terms of formulation and handling, only based on the limited property. Thus, the degree of freedom for compounding and design cannot be adjusted or expanded on the user side. More specifically, it is impossible to implement the ionic management on site for a silicone material on the user side to adjust various characteristics (such as performance and solubility of the silicone material) for various objects of the user. All things considered, a degree of freedom for compounding and design is limited for formulation technicians in charge of various formats (such as cosmetics) and a phase of a conventional silicone material.

Conventional non-ionic silicones, known as PEG-free hydrophilic silicone materials, further include a polyhydric alcohol (polyhydroxy) modified silicone and the like. Generally, the polyhydric alcohol (polyhydroxy) modified silicone has higher viscosity than polyether modified silicone with substantially the same chemical structure in a portion other than the hydrophilic portion, and thus requires viscosity management including using an oil agent as a diluent to be more easily handled, to be produced more efficiently, and the like. However, conventionally hydrophilic silicones include a hydrophilic modifier as an impurity, and it has been difficult to reduce the viscosity thereof through dilution using the oil agent even if it has transparent outer appearance. This is because the dilution using the oil agent results in precipitation of the hydrophilic modifier, which has been dissolved in the system, resulting in cloudiness of the outer appearance. This cloudiness results in separation and sedimentation within a short period of time due to a low viscosity of the diluent. Thus, many conventional hydrophilic silicones have needed to have a high viscosity to be rolled out as a product. Furthermore, it is difficult to select a suitable diluent, and a degree of freedom for improving production efficiency is low.

The inventors of the present application have found a further problem inhibiting the accomplishment of the goal with the silicone material including the known tertiary-amine structure-containing polyhydric alcohol modified silicone, due to the following complex factors in an industrial production process.

Factor 1) An excessive amount of a hydrophilic modifier is used in the manufacturing because when the hydrophilic modifier is introduced to organopolysiloxane, reaction is not completed with a mole ratio of 1:1 between functional groups to be bonded, and because such an amount is required for preventing the polysiloxane-side functional group from remaining to satisfy the safety requirement.

Factor 2) The hydrophilic modifier has a polymer structure or has ionicity or high polarity even when the molecular weight thereof is low, and thus is non-volatile. Thus, the excess amount of the hydrophilic modifier cannot be removed through heating vacuum treatment after the production process for the modified silicone has been completed.

Factor 3) There is no practical technique available to selectively remove the hydrophilic modifier from the hydrophilic silicone composition manufactured as described above.

With the composite effect of these factors 1) to 3), it is extremely difficult to provide a PEG-free hydrophilic silicone material that has performance equivalent or superior to those of conventionally known non-ionic silicones at a low cost in an industrial and commercial scale. As a result, an object of providing a novel organopolysiloxane having a hydrophilic group containing a specific tertiary-amine structure and having no other nitrogen atom, polyoxyalkylene structure, or reactive structure to radical polymerization, or acid-neutralized salt thereof is unknown in the first place.

The present invention is made to solve the multiple fundamental problems described above, and a first object of the present invention is to provide a PEG-free hydrophilic silicone material that can be manufactured at a much lower cost than that manufactured with the prior techniques, while having a performance value equivalent or superior to that of a polyether modified silicone.

A second object of the present invention is to provide a "novel organopolysiloxane having a hydrophilic group containing a specific tertiary-amine structure and having no other nitrogen atom, polyoxyalkylene structure, or reactive structure to radical polymerization, or acid-neutralized salt thereof" that can be easily manufactured, involve no separation, sedimentation of unreacted materials, and cloudiness after the production process, have extremely high transparency, be chemically stable, and have good compatibility with various types of materials, and a manufacturing process of the same.

A third object of the present invention is to provide an acid-neutralized product of the organopolysiloxane and a manufacturing process of the same. More specifically, it is a further object to, with the basic two ionic properties of the novel organopolysiloxane according to the present invention, enable adjustment for various characteristics (such as performance and solubility of the silicone material) while the silicone is compounded into a formulation for various objects of the user, that is, provide a higher degree of freedom for compounding and design for cosmetic formulation technicians.

A fourth object of the present invention is to provide a surfactant including organopolysiloxane and/or an acid-neutralized product thereof, as well as an emulsifier for a water-in-oil emulsion, an oil agent, a powder dispersant, and a powder surface treatment agent.

A fifth object of the present invention is to provide a stable composition, emulsion, a dispersant, and a solution including the organopolysiloxane and/or an acid-neutralized product thereof as well as an oil agent and/or a polar solvent. This object further includes a larger advantage of management of achieved viscosity.

The present invention has a sixth object of providing a preparation for external use and a cosmetic containing the organopolysiloxane and/or an acid-neutralized product thereof.

Means for Solving the Problems

The inventors of the present invention have made extensive studies to obtain a compound with a silicone chain having a PEG-free hydrophilic group introduced through a simple process, using an inexpensive raw material to accomplish the goal described above. As a result, the inventors have found that the goal can be accomplished with a novel organopolysiloxane having a hydrophilic group containing a specific tertiary-amine structure only in a molecular chain side chain and having no other nitrogen atom, polyoxyalkylene structure, or reactive structure to radical polymerization, or acid-neutralized salt thereof, and thus made the present invention based on this idea.

Specifically, the problems of the present invention are solved by an organopolysiloxane or acid-neutralized salt thereof represented by the following general formula (1)

[Formula 1]

$$R^1{}_a R^2{}_b L^1{}_c Q_d SiO_{(4-a-b-c-d)/2} \qquad (1)$$

{wherein $R^1$ represents a monovalent organic group not having nitrogen atom or polyoxyalkylene structure or any reactive structure to radical polymerization (with the proviso that $R^2$, L and Q are excluded therefrom), a hydrogen atom, or a hydroxyl group;

$R^2$ represents a halogen-substituted or non-substituted, and linear or branched monovalent hydrocarbon group having 6 to 30 carbon atoms, $L^1$ is a silylalkyl group having a specific siloxane dendron structure or a chain organosiloxane group, Q represents a side-chain bonded hydrophilic group having tertiary-amine structure and represented by following general formula: $-C_qH_{2q}-O-CH_2-CH(OH)-CH_2-N(R^{Q1})(R^{Q2})$ (wherein q is a number ranging from 1 to 6, $R^{Q1}$ and $R^{Q2}$ are a halogen-substituted or non-substituted monovalent hydrocarbon group or alkanol group, at least one of $R^{Q1}$ and $R^{Q2}$ has a hydroxyl group, but total number of hydroxyl groups in $R^{Q1}$ and $R^{Q2}$ is at most three (3), and any of $R^{Q1}$ and $R^{Q2}$ does not have a nitrogen atom in the group);

and each of a, b, c, and d is independently a number having the following range: $1.0 \le a \le 2.5$, $0 \le b \le 1.5$, $0 \le c \le 1.5$, and $0.0001 \le d \le 1.5$} and having the number of Si atoms ranging from 4 to 1000.

The inventors of the present invention have found that an organopolysiloxane or acid-neutralized salt thereof that has a hydrophilic group having tertiary-amine structure that is Q in a side chain of polysiloxane represented by the following structural formula (1-1)

[Formula 2]

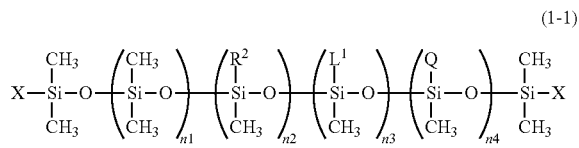

(1-1)

(where
$R^2$, $L^1$, and Q are independently the same as defined above,
X is a group selected from the group consisting of a methyl group, monoglycerol group, diglycerol group, triglycerol group, polyglycerol group or $R^2$, and $L^1$ group;
$n1+n2+n3+n4$ is a number ranging from 2 to 1,000,
n1 is a number ranging from 1 to 999,
n2 is a number ranging from 0 to 998,
n3 is a number ranging from 0 to 998, and
n4 is a number ranging from 1 to 999)
can preferably solve the problems mentioned above and achieved the present invention.

Furthermore, the inventors of the present invention have found that an organopolysiloxane or acid-neutralized salt thereof that is a hydrophilic group having tertiary-amine structure having Q represented by Formula:

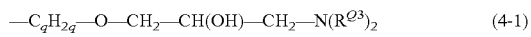

(4-1)

(wherein q is a number ranging from 1 to 6, $R^{Q3}$ independently represents linear or branched C1-C10 alkanol group having one alcoholic hydroxyl group)
can preferably solve the problems mentioned above and achieved the present invention. Furthermore, the inventors of the present invention have found that the organopolysiloxane or acid-neutralized salt thereof further including a halogen-substituted or non-substituted, and linear or branched monovalent hydrocarbon group, serving as $R^2$, having 6 to 30 carbon atoms, a silylalkyl group serving as a $L^1$ and having a specific siloxane dendron structure, or a chain organosiloxane group can extremely preferably solve the problems mentioned above and achieved the present invention.

Furthermore, the inventors of the present invention have found that a surfactant or a dispersant, an oil agent, a thickening agent, or a cosmetic raw material containing the organopolysiloxane or acid-neutralized salt thereof can solve the problems mentioned above and achieved the present invention. By adjusting the range of the molecular weight of the organopolysiloxane or acid-neutralized salt thereof depending on various applications, the problems to be solved by the present application can be more preferably solved.

Furthermore, the inventors of the present invention have found that a composition including (A) the organopolysiloxane or acid-neutralized salt thereof, and (B) at least one oil agent, which is in the form of a liquid at 5 to 100° C., and is selected from the group consisting of a silicone oil, a non-polar organic compound, and a low-polar compound, and preferably, further including (C) water and/or at least one type of alcohol selected from the group consisting of lower alcohols and polyhydric alcohols can solve the problems mentioned above and achieved the present invention.

Furthermore, the inventors of the present invention have found that a water-based composition containing (A') an acid-neutralized product of the organopolysiloxane, in which the acid of the acid-neutralized product is at least one type of acid selected from the group consisting of carboxylic acids, amino acids, and inorganic acids can solve the problems mentioned above and achieved the present invention.

Furthermore, the inventors of the present invention have found that a cosmetic or a preparation for external use containing the organopolysiloxane or acid-neutralized salt thereof can solve the problems mentioned above and achieved the present invention.

Furthermore, the inventors of the present invention have found that a manufacturing process of the organopolysiloxane or acid-neutralized salt thereof including Steps (I) to (IV) described below can solve the problems mentioned above and achieved the present invention.

(I) reacting organohydrogen polysiloxane with an epoxy compound having an unsaturated hydrocarbon group;
(II) removing unreacted epoxy compound having an unsaturated hydrocarbon group from the system following said step (I);
(III) processing ring-opening reaction between an epoxy group and a secondary amine compound having a hydroxyl group following said step (II); and
(IV) optionally, removing unreacted secondary amine compound having a hydroxyl group from the system following said step (III).

Furthermore, the inventors of the present invention have found that a manufacturing process of the organopolysiloxane or acid-neutralized salt thereof including Steps (I) to (III) described below can solve the problems mentioned above and achieved the present invention.

(I) obtaining an intermediate by ring-opening reaction between an epoxy compound having an unsaturated hydrocarbon group and a secondary amine compound having a hydroxyl group;
(II) removing unreacted raw materials from the system following said step (I); and
(III) reacting the intermediate with organohydrogen polysiloxane following said step (II).

Effects of the Invention

The present invention can provide a novel organopolysiloxane or acid-neutralized salt thereof as a PEG-free hydrophilic silicone material that has performance equivalent or superior to those of conventionally known non-ionic silicones and can be manufactured at a low cost. The ionic management of the silicone material can be implemented on the user side. Thus, the adjustment of various characteristics (such as performance and solubility of the silicone material) including whether neutralization is implemented for formulation can be performed on site, so that a degree of freedom for compounding and design is extremely improved for formulation technicians. In the most basic example, the organopolysiloxane is non-ionic unless it is neutralized, and can be dissolved in various hydrophobic oil agents (such as non-polar hydrocarbon oil, low-polar silicone oil, polar oil including ester groups or the like) and can be stably compounded in the oil phase or the oil-water interface. When the organopolysiloxane is neutralized with an acid, the acid-neutralized salt is modified to have a cationic property. As a result, there is an advantage that the solubility of the organopolysiloxane into various polar solvents and water is extremely improved, and thus can be easily stably compounded into an aqueous phase including these.

The organopolysiloxane or the like provided by the present invention is a novel organopolysiloxane having a hydrophilic group containing a specific tertiary-amine structure and having no other nitrogen atom, polyoxyalkylene structure, or reactive structure to radical polymerization, or acid-neutralized salt thereof. The functional group can be obtained by obtaining an epoxy modified silicone intermediate by introducing epoxide including an unsaturated group into organopolysiloxane including Si—H group by hydrosilylation reaction, and by further reacting the epoxy modified silicone intermediate with alkanol group-containing secondary amine. Furthermore, a modified organopolysiloxane according to the present invention is a high purity polymer including no residual hydrophilic modifier or the like. This is also a novel feature not achieved by various conventional hydrophilic silicone compositions. The high purity modified organopolysiloxane according to the present invention has a further advantage that it can be obtained through a simple process, without requiring a complex manufacturing step.

Furthermore, the organopolysiloxane and the like provided by the present invention is a hydrophilic organopolysiloxane having a PEG-free structure that can have lower viscosity and can be more easily managed, compared with organopolysiloxane obtained by replacing the hydrophilic group with a polyether modified group, due to an effect of a unique structure of the hydrophilic group, a characteristic binding position to the polysiloxane chain, a combination with a hydrophobic group, or the like. According to the conventional common technical knowledge and understanding in the industry, the hydrophilic organopolysiloxane having a PEG-free structure has been well known to have an increased viscosity. However, the organopolysiloxane and the like provided by the present invention advantageously have low viscosity and can be easily handled, even in a case with non-ionic silicones having a polyether modified group, in a non-diluted state. Furthermore, the organopolysiloxane according to the present invention dissolves into various oil agents in a transparent manner, and thus can be diluted to have lower viscosity to have improved production efficiency and usability. Alternatively, a wide range of diluents can be selected in accordance with the customer preference.

Furthermore, with organopolysiloxane and the like provided by the present invention have a property of achieving higher viscosity of a water-in-oil emulsion using the organopolysiloxane and the like as an emulsifier than that of emulsion obtained by using polyether modified silicone having substantially the same chemical structure except for a portion other than the hydrophilic portion. Specifically, the organopolysiloxane according to the present invention effectively increases the viscosity of the oil phase from that of the polyether modified silicone when water coexists, so that more stable emulsion can be achieved. Furthermore, an emulsifier achieving water-in-oil emulsion featuring low viscosity and high stability can be designed through selection of a molecular structure. Thus, the basic molecular property of the organopolysiloxane and the like according to the present invention provides a behavior of the viscosity according to needs or management of oil phase viscosity, suitable for both the manufacturer and the user.

The silicone material having a unique property as described above has not been known, and is provided as an effect of the invention that directly or indirectly relates to the characteristic technical effect of the present invention.

The present invention provides a manufacturing process of the organopolysiloxane and the like described above easily and at a low cost. The organopolysiloxane and the like obtained by the method of production feature advantages of involving no separation, sedimentation of unreacted materials, and cloudiness after the production process, having extremely high transparency, and being chemically stable and having good compatibility with various types of materials.

The present invention can provide a surfactant, an oil agent, a thickening agent, a cosmetic raw material, and the like including the organopolysiloxane and the like described above. Possible applications of the surfactant and the like include an emulsifier for water-in-oil emulsion, a powder dispersant, a powder surface treatment agent, and the like.

The present invention can provide various compositions including the organopolysiloxane and the like described above. Specifically, a stable composition, emulsion including water, aqueous composition, dispersant, or solution including the organopolysiloxane or an acid-neutralized product thereof and an oil agent and/or a polar solvent can be provided. As described above, such compositions feature easy viscosity management and have excellent stability.

The present invention can provide a preparation for external use or a cosmetic including the organopolysiloxane and the like described above. More specifically, the "novel organopolysiloxane having a hydrophilic group containing a specific tertiary-amine structure and has no other nitrogen atom, polyoxyalkylene structure, or reactive structure to radical polymerization, or acid-neutralized salt thereof" according to the present invention can be used to provide a preparation for external use or a cosmetic with a low safety risk and excellent texture and stability, including no compound containing polyoxyethylene groups to conform to a global trend of refining the entire structure of an end consumer product to be PEG-free formulations.

MODE FOR CARRYING OUT THE INVENTION

[Novel Organopolysiloxane]
An organopolysiloxane or acid-neutralized salt thereof according to the present invention will be described below in detail. The organopolysiloxane according to the present invention is represented by the following general formula (1)

[Formula 3]

$$R^1_a R^2_b L^1_c Q_d SiO_{(4-a-b-c-d)/2} \qquad (1)$$

In this formula, $R^1$s are optionally the same as or different from each other, are not a functional group corresponding to $R^2$, $L^1$, or Q, and each represent a monovalent organic group not having nitrogen atom or polyoxyalkylene structure or any reactive structure to radical polymerization, a hydrogen atom, or a hydroxyl group. The organopolysiloxane according to the present invention has no nitrogen-containing organic group other than the hydrophilic group containing the tertiary-amine structure represented by Q. The organopolysiloxane according to the present invention has a function serving as a surfactant and the like, has no polyoxyalkylene structure (polyether or the like) to achieve a PEG-free formulation, and has no reactive structure to radical polymerization. Such $R^1$ is preferably selected from a C1-C5 alkyl group, a trifluoropropyl group, a pentafluoroethyl group, an alkoxy group, a hydrogen atom, or a hydroxyl group. Industrially, $R^1$ is preferably a methyl group, an ethyl group, or a hydroxyl group, and in particular, 90% by mole to 100% by mole of the entire $R^1$ is preferably a group selected from a methyl group, an ethyl group, or a hydroxyl group.

$R^2$ is a halogen-substituted or non-substituted, and linear or branched monovalent hydrocarbon group having 6 to 30 carbon atoms, and is a certain functional group of the organopolysiloxane or acid-neutralized salt thereof according to the present invention. Such $R^2$ is preferably a halogen-substituted or non-substituted alkyl group or aryl group, and is preferably an alkyl group, an aryl group, or an aralkyl group having 6 to 30 carbon atoms, in which carbon-atom-bonded hydrogen atoms may be partly or entirely substituted with fluorine atoms. Specific examples may include hexyl groups, heptyl groups, octyl groups, decyl groups, dodecyl groups, hexadecyl groups, and other alkyl groups having 6 to 30 carbon atoms; cyclopentyl groups, cyclohexyl groups, and other cycloalkyl groups having 6 to 30 carbon atoms; phenyl groups, tolyl groups, xylyl groups, and other aryl groups; and phenethyl groups, 2-phenylpropyl groups, and other aralkyl groups. When alkyl groups and the like having 6 to 30 carbon atoms are included as $R^2$, the organopolysiloxane according to the present invention can have improved affinity or compatibility with hydrocarbon-based or ester-based oil agents and other cosmetic raw materials.

$L^1$ represents a silylalkyl group having a siloxane dendron structure, in the case of i=1, represented by the following general formula (3)

[Formula 4]

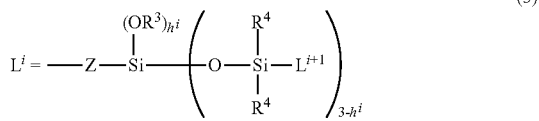

(3)

(wherein $R^3$ independently represents a substituted or non-substituted, and linear or branched monovalent hydrocarbon group having 1 to 30 carbon atoms, $R^4$ independently represents an alkyl group having 1 to 6 carbon atoms or a phenyl group, Z is a divalent organic group, i specifies a number of generations of said silylalkyl group, represented by $L^i$, in the case in which a number of generations of said silylalkyl group, which is a number of repetitions of said silylalkyl group, is k, i is an integer ranging from 1 to k, and a number of generations k is an integer ranging from 1 to 10, $L^{i+1}$ is said silylalkyl group in the case of i<k, and $L^{i+1}$ is $R^4$ in the case of i=k, and $h^i$ is a number ranging from 0 to 3), or an organosiloxane group in the form of a chain, represented by the following General Formula (2-1)

[Formula 5]

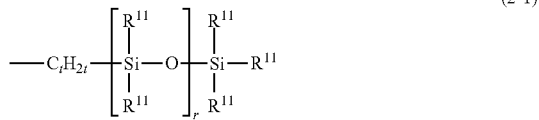

(2-1)

(wherein $R^{11}$ is independently a substituted or non-substituted monovalent hydrocarbon group having 1 to 30 carbon atoms, a hydroxyl group or a hydrogen atom, and at least one of $R^{11}$ is said monovalent hydrocarbon group; t is a number ranging from 2 to 10; and r is a number ranging from 1 to 500), or represented by the following general formula (2-2)

[Formula 6]

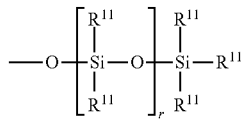

(2-2)

(wherein $R^{11}$ and r are the same as defined above); and is a certain functional group of the organopolysiloxane or acid-neutralized salt thereof according to the present invention.

In particular, the silylalkyl group having the siloxane dendron structure illustrated in general formula (3) includes a structure with a carbosiloxane unit expanding in a dendrimer form, and can be favorably combined with a hydrophilic group serving as a highly water-repellent functional group Q. Thus, this group can provide fresh and natural feel with an unpleasant sticky feeling suppressed when the preparation for external use or the cosmetic having the organopolysiloxane or acid-neutralized salt thereof according to the present invention is used. Furthermore, the silylalkyl group having the siloxane dendron structure is a functional group that is chemically stable and thus can provide an advantageous property of being used in combination with a wide variety of components.

The functional group Q is a side-chain bonded non-ionic hydrophilic functional group, implementing a characteristic property of the organopolysiloxane according to the present invention, and exerts cationic property upon being neutralized with an acid, and thus enables the ionic management during use. The organopolysiloxane including the functional group Q in the non-diluted state has lower viscosity than silicones having the functional group Q replaced with a known polyether modified group, and further features good affinity with an oil agent, so that the viscosity can be easily managed. Furthermore, the organopolysiloxane having the functional group Q, when combined with water, has a unique property of having higher viscosity than the silicones having the functional group Q replaced with a known polyether modified group, and of forming a stable emulsion composition, contrary to the non-diluted case.

Specifically, the functional group Q represents a hydrophilic group having tertiary-amine structure and represented by following general formula: $-C_qH_{2q}-O-CH_2-CH(OH)-CH_2-N(R^{Q1})(R^{Q2})$
where q is a number ranging from 1 to 6, $R^{Q1}$ and $R^{Q2}$ are a halogen-substituted or non-substituted, monovalent hydrocarbon group or alkanol group and do not have a nitrogen atom in the group, at least one of $R^{Q1}$ and $R^{Q2}$ has a hydroxyl group, but total number of hydroxyl groups in $R^{Q1}$ and $R^{Q2}$ needs to be at most three (3), and is preferably 2. On the other hand, a structure having the total number of hydroxyl groups in $R^{Q1}$ and $R^{Q2}$ more than 3 (such as a modified group derived from sugar, for example) has disadvantages including: insufficient surface activity ability; increased viscosity compromising handling ability; and compromised affinity with an oil agent. Thus, the technical effects of the present invention cannot be achieved, unless the structure described above is selected. As described later, the organopolysiloxane having the functional group Q can be manufactured to have high purity at a comparatively low cost.

In particular, the functional group Q is preferably a hydrophilic group having tertiary-amine structure represented by the following formula:

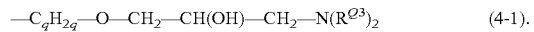

(4-1).

In the formula, q is a number ranging from 1 to 6, $R^{Q3}$ independently represents linear or branched C1-C10 alkanol group having one alcoholic hydroxyl group. Logically, the numerical limit of the hydroxyl groups in Q described above is two, because two alkanol groups including a single alcoholic hydroxyl group is provided.

Most preferably, the functional group Q bonded to the side chain of a siloxane molecule is a hydrophilic group having tertiary-amine structure represented by the formula: —$C_qH_{2q}$—O—$CH_2$—CH(OH)—$CH_2$—N($R^{Q4}$)$_2$ (4-2).

In the formula, q is a number ranging from 1 to 6, and each $R^{Q4}$ independently represents —$CH_2$—CH($CH_3$)—OH or —$CH_2$—$CH_2$—OH. When —$CH_2$—CH($CH_3$)—OH is selected as $R^{Q4}$, the organopolysiloxane having the functional group Q is likely to have good affinity with other oil agents as a whole, and thus is suitably used as a surfactant and a thickening agent. On the other hand, when —$CH_2$—$CH_2$—OH is selected as $R^{Q4}$, the organopolysiloxane having the functional group Q is likely to have good affinity with water as a whole, and thus is suitably used as a water-soluble oil agent. These policies regarding the functional group selection, molecular design, and compatibility of use are covered by an intended application of the organopolysiloxane or acid-neutralized salt thereof according to the present invention, and thus are included in the scope and the advantageous technical effects of the present invention. The functional group Q is required to be bonded only to the side chain of the siloxane molecule. Specifically, when the functional group Q is provided to a molecular chain terminal, the performance/compounding stability is compromised due to molecular design limitations. Thus, the scope of the invention according to the present application does not cover organopolysiloxane with a molecular chain terminal having the functional group Q.

In general formula (1) below, each of a, b, c, and d is independently a number having the following range: $1.0 \le a \le 2.5$, $0 \le b \le 1.5$, $0 \le c \le 1.5$, and $0.0001 \le d \le 1.5$. Preferable values of b and c, depending on the required functional group, are as follows:
(1) $0.001 \le b \le 1.5$ and $0 \le c \le 1.5$ when a group represented by $R^2$ is included;
(2) $0 \le b \le 1.5$ and $0.001 \le c \le 1.5$ when a group represented by $L^1$ is included; and
(3) $0.001 \le b \le 1.5$ and $0.001 \le c \le 1.5$ when both a group represented by $R^2$ and a group represented by $L^1$ are included.

[Polymerization Degree, Suitable Structure, and Function]

The organopolysiloxane or acid-neutralized salt thereof according to the present invention has the number of Si atoms in a range from 4 to 1000, and preferably in a range from 4 to 500. In particular, the number of various siloxane units (the M unit, D unit, T unit, and Q unit bonded with the functional groups $R^1$, $R^2$, and $L^1$ as well as the D unit bonded with the functional group Q described above) forming the main chain is preferably in a range from 4 to 500.

In particular, through the selection of the siloxane polymerization degree of the main chain of the organopolysiloxane or acid-neutralized salt thereof according to the present invention, organopolysiloxanes with a low polymerization degree, a medium polymerization degree, and a high polymerization degree can be designed, whereby organopolysiloxanes suitable for desired applications can be provided.

Specifically, in the present invention, an organopolysiloxane or acid-neutralized salt thereof with a siloxane polymerization degree in a range from 4 to 50 (preferably, approximately from 4 to 40) features good affinity with water or a polar solvent, and in particular can be used in a form of the acid-neutralized salt to be suitably used for the water-soluble oil agent. In the description below, the term "low polymerization type" may indicate the organopolysiloxane or acid-neutralized salt thereof with the polymerization degree described above.

The organopolysiloxane or acid-neutralized salt thereof according to the present invention with the siloxane polymerization degree in a range from 40 to 200, preferably in a range from 40 to 60, and is more preferably approximately 50 can have extremely good affinity with a silicone-based oil agent, or with a silicone-based oil agent and other oil agents, with the functional group Q described above or the other functional groups selected, and thus can be suitably used as a surfactant and the like for forming a stable water-in-oil emulsion. In the description below, the term "medium polymerization type" may indicate the organopolysiloxane or acid-neutralized salt thereof with the polymerization degree described above. This type is particularly suitably used as a surfactant or a dispersant.

The organopolysiloxane or acid-neutralized salt thereof according to the present invention with a siloxane polymerization degree of 200 or more (preferably in a range from 200 to 400) can be suitably used as a thickening agent for an oil agent. In particular, the organopolysiloxane with a siloxane polymerization degree of 200 or more has particularly high affinity with a silicone-based oil agent, and can be suitably used as a thickening agent for volatile silicone oil (such as decamethylcyclopentasiloxane (D5), caprylyl methicone, or dimethyl polysiloxane with a low polymerization degree) for which a general thickening agent cannot provide a sufficient thickening effect. The organopolysiloxane with the high polymerization degree that additionally includes a group represented by $R^2$ can be used as a thickening agent for volatile hydrocarbon oil (such as isododecane, isohexadecane, or light liquid isoparaffin) for which a general silicone-based thickening agent is likely to fail to provide a sufficient thickening effect. In the description below, the term "high polymerization type" may indicate the organopolysiloxane or acid-neutralized salt thereof with the polymerization degree described above. This type, which corresponds to the thickening agent, may also be used as an oil agent, a surfactant, or a dispersant.

As described above, the organopolysiloxane or acid-neutralized salt thereof according to the present invention can provide various preferable applications, depending on the polymerization degree thereof. These applications may all be applications for a cosmetic raw material.

Low polymerization type: water-soluble oil agents (acid-neutralized salt in particular), (non-neutralized or neutralized) powder dispersants or treatment agents Medium polymerization type: surfactants, emulsifiers, feel improvement oil agents, or dispersants with good affinity with silicone-based oil agents/silicone-based solutions and other oil agents High polymerization type: surfactants, dispersants, oil agents, thickening agents for oil agents (in particular, thickening agents for silicone-based oil agents including volatile silicone oil or volatile hydrocarbon oil), or viscous emulsifiers Preferably, the organopolysiloxane according to the present invention is a methyl polysiloxane preferably represented by the structural formula below, and has a linear and a side chain having a hydrophilic group having tertiary-amine structure that is the functional group Q.

Structural Formula (1-1)

[Formula 7]

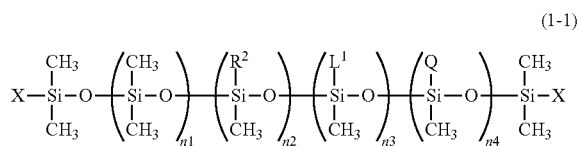
(1-1)

(wherein
$R^2$, $L^1$, and Q are independently the same as defined above,
X is a group selected from the group consisting of a methyl group, monoglycerol group, diglycerol group, triglycerol group, polyglycerol group or $R^2$, and $L^1$ group;
n1+n2+n3+n4 is a number ranging from 2 to 1,000,
n1 is a number ranging from 1 to 999,
n2 is a number ranging from 0 to 998,
n3 is a number ranging from 0 to 998, and
n4 is a number ranging from 1 to 999)

n1 is preferably a number ranging from 10 to 500, and is more preferably from 25 to 400. n2 is preferably a number ranging from 0 to 250, and is more preferably from 0 to 150. Note that if $R^2$ is the long-chain alkyl group described above, it is particularly preferable to satisfy n2>1, considering the surface activity and compatibility with oil agents other than silicone. n3 is preferably a number ranging from 0 to 250, and it is particularly preferable that n3>1 is satisfied and one or more silylalkyl groups (-$L^1$) having a siloxane dendron structure is provided in a side chain portion. n4 is preferably a number ranging from 1 to 500, and is more preferably from 1 to 50. X is preferably a methyl group.

[Acid Neutralized Product]

The organopolysiloxane according to the present invention has a hydrophilic group having tertiary-amine structure that is the side-chain bonded functional group Q, and thus is modified to have cationic property upon being neutralized with an acid so as to have solubility to various polar solvents and water largely improved, and thus can be advantageously stably compounded into the aqueous phase including these. This is a particularly advantageous property regarding the low polymerization degree type, and is a fundamental property for ionic management at the time of formulation or compounding, which is a feature of the organopolysiloxane according to the present invention.

A product obtained by neutralizing the organopolysiloxane with an acid may be a completely neutralized product or a partially neutralized product, appropriately selected depending on a requirement regarding the ionic management at the time of formulation or compounding. Specifically, when high solubility into an aqueous phase is required, the complete neutralization may be selected. When balanced solubility for both the oil phase and the aqueous phase is required, the partially neutralized product may be selected for the formulation and compounding.

An acid substance used for the neutralization is not particularly limited. Still, an acid substance featuring a low negative impact on human bodies after the neutralization is preferably used, considering the application as a cosmetic raw material. Specifically, one or more types of acids, selected from the group consisting of carboxylic acid, amino acid, and inorganic acid can be preferably used. Particularly preferable examples include (α-) hydroxy acid, lactic acid, glycolic acid, citric acid, malic acid, acetic acid, butyric acid, amino acid, and hydrochloric acid. In neutralization through ion exchange by adding acid inorganic salts such as lithium hydrogen sulfate, sodium hydrogen sulfate, potassium hydrogen sulfate, rubidium hydrogen sulfate, cesium hydrogen sulfate, ammonium hydrogen sulfate, and sodium hydrogen sulfite, liquid shifting to an acid side using a pH adjuster and the like may be employed. Such neutralization is covered by the scope of the invention according to the present application, and is included in a scheduled application.

[Purity and Method of Production]

The organopolysiloxane according to the present invention is a novel compound, that is, not a conventionally known compound, and has a favorable feature of enabling the hydrophilic modifier to be selectively removed during the production steps. Specifically, the organopolysiloxane or acid-neutralized salt thereof according to the present invention is a high purity polymer including no residual hydrophilic modifier and can be obtained through a simple process and thus requires no complex production steps, unlike various conventional hydrophilic silicone compositions.

The organopolysiloxane according to the present invention may be obtained through a step including: reacting organohydrogen polysiloxane with an epoxy compound having an unsaturated hydrocarbon group in advance; and then processing ring-opening reaction between an epoxy group introduced to the siloxane chain and a secondary amine compound having a hydroxyl group. The organopolysiloxane according to the present invention has the hydrophilic group Q introduced to the molecular chain side chain, and thus the organohydrogen polysiloxane (raw material) needs to include silicon-atom bonded hydrogen atoms bonded to at least the molecular chain side chain.

Such a method of production includes the following Steps (I) to (IV). With this method of production, the unreacted raw material can be easily removed from the system, and no remaining impurities are involved as a result of internal metastasis, and thus this is the most preferable method of production.

(I) reacting organohydrogen polysiloxane with an epoxy compound having an unsaturated hydrocarbon group;

(II) removing unreacted epoxy compound having an unsaturated hydrocarbon group from the system following said step (I);

(III) processing ring-opening reaction between an epoxy group and a secondary amine compound having a hydroxyl group following said step (II); and (IV) optionally, removing unreacted secondary amine compound having a hydroxyl group from the system following said step (III).

In the same manner, the organopolysiloxane according to the present invention may be produced by processing ring-opening reaction between an epoxy compound having an unsaturated hydrocarbon group and a secondary amine compound having a hydroxyl group and reacting an intermediate having an unsaturated hydrocarbon group with organohydrogen polysiloxane. In this case, however, reactants as a result of internal metastasis may possibly remain in the system.

Such a method of production includes the following Steps (I) to (III).

(I) obtaining an intermediate by ring-opening reaction between an epoxy compound having an unsaturated hydrocarbon group and a secondary amine compound having a hydroxyl group;

(II) removing unreacted raw materials from the system following said step (I); and (III) reacting the intermediate with organohydrogen polysiloxane following said step (II).

The step of reacting the epoxy compound having an unsaturated hydrocarbon group or the intermediate with the organohydrogen polysiloxane preferably includes a hydrosilylation reaction, and a hydrosilylation reaction catalyst is not limited to a specific catalyst, so long as the hydrosilylation reaction can be promoted. Many metals and compounds are known thus far as hydrosilylation reaction catalysts, which can be appropriately selected and used in the present invention. Examples of the hydrosilylation reaction catalyst include platinum-based catalysts, rhodium-based catalysts, and palladium-based catalysts. Specific examples of the hydrosilylation reaction catalyst can include fine particulate platinum adsorbed on silica fine powder or a carbon powder carrier, chloroplatinic acids, alcohol-modified chloroplatinic acids, olefin complexes of a chloroplatinic acid, coordinate compounds of a chloroplatinic acid and vinyl siloxane, platinum black, platinum-alkenyl siloxane complexes, platinum-olefin complexes, and platinum-carbonyl complexes, and platinum-alkenyl siloxane complexes are particularly preferable. As catalysts for promoting the hydrosilylation reaction, iron, ruthenium, iron/cobalt and other non-platinum metal catalysts can be used.

The hydrosilylation reaction conditions can be arbitrarily selected based on the raw material and the presence or absence of a solvent described later, but the composition can be obtained by adding a small amount of an antioxidant such as tocopherol (vitamin E), BHT (butylated hydroxytoluene), or the like, and then heating and stirring at room temperature to 200° C., and preferably 70 to 150° C. under an inert gas atmosphere such as nitrogen or the like. Note that the antioxidant may be added after hydrosilylation is completed. The reaction time can be selected based on the reaction scale, amount of catalyst used, and reaction temperature, and is generally within a range of several minutes to several hours. Furthermore, the reaction may be performed under reduced pressure in order to improve quality or the like, and for example, the reaction conditions proposed in JP H11-116670A can be applied without particularly limitation.

Note that the end point of the hydrosilylation reaction can be confirmed by the disappearance of Si—H bond absorption by infrared spectroscopy (IR), or the absence of hydrogen gas generation by an alkali decomposition gas. Note that the silicon-bonded hydrogen atoms (Si—H) in the organopolysiloxane containing a SiH group which is a reaction raw material can be analyzed by the same method, and therefore, the amount of hydrogen gas generation can be specified. Alkali Decomposition Gas Generation Method: Method of reacting at room temperature a 28.5 mass % caustic potash ethanol/water mixed solution with a solution where a sample is dissolved in toluene or IPA, collecting the generated hydrogen gas in a collection tube, and then measuring the volume thereof In the method of production according to the present invention, a typical epoxy compound having an unsaturated hydrocarbon group is allyl glycidyl ether (AGE). Typical hydroxyl group-containing secondary amine compounds can be, but not be limited to, one type or more selected from diisopropanolamine (DIPA), N-methyl ethanolamine (MEA), and diethanolamine (DEA). In general, these epoxy compounds having an unsaturated hydrocarbon group and hydroxyl group-containing secondary amine compounds are in expensive and easily available, and are advantageous in that they can be produced at an extremely low cost, unlike conventional non-ionic PEG-freehydrophilic silicones, such as sugar modified silicone and glycerin modified silicone.

[Composition Containing Oil Agent]

The organopolysiloxane or acid-neutralized salt thereof according to the present invention is preferably used as a composition having good affinity with an oil agent, and in particular, containing one or more oil agent, which is in the form of a liquid at 5 to 100° C., and is selected from a silicone oil, a non-polar organic compound, and a low-polar organic compound. These oil agents may be an organopolysiloxane or other diluents according to the present invention, and may be oil phase components in cosmetics or formulations such as preparation for external uses.

Specific examples of silicone oil may include, as a cyclic organopolysiloxane, hexamethyl cyclotrisiloxane (D3), octamethyl cyclotetrasiloxane (D4), decamethylcyclopentasiloxane (D5), dodecamethylcyclohexasiloxane (D6), 1,1-diethylhexamethyl cyclotetrasiloxane, phenylheptamethyl cyclotetrasiloxane, 1,1-diphenylhexamethyl cyclotetrasiloxane, 1,3,5,7-tetravinyltetramethyl cyclotetrasiloxane, 1,3,5,7-tetramethyl cyclotetrasiloxane, 1,3,5,7-tetracyclohexyltetramethyl cyclotetrasiloxane, tris (3,3,3-trifluoropropyl) trimethyl cyclotrisiloxane, 1,3,5,7-tetra (3-methacryloxypropyl) tetramethyl cyclotetrasiloxane, 1,3,5,7-tetra (3-acryloxypropyl) tetramethyl cyclotetrasiloxane, 1,3,5,7-tetra (3-carboxypropyl) tetramethyl cyclotetrasiloxane, 1,3,5,7-tetra (3-vinyloxypropyl) tetramethyl cyclotetrasiloxane, 1,3,5,7-tetra (p-vinylphenyl) tetramethyl cyclotetrasiloxane, 1,3,5,7-tetra[3-(p-vinylphenyl) propyl]tetramethyl cyclotetrasiloxane, 1,3,5,7-tetra (N-acryloyl-N-methyl-3-aminopropyl) tetramethyl cyclotetrasiloxane, and 1,3,5,7-tetra (N,N-bis(lauroyl)-3-aminopropyl) tetramethyl cyclotetrasiloxane. Examples of linear organopolysiloxanes may include molecular-chain-on-both-terminals trimethylsiloxy group-blocked dimethyl polysiloxane (low viscosity (e.g., 2 cst or 6 cst) dimethyl silicone to high viscosity (e.g., 1,000,000 cst) dimethyl silicone), organohydrogen polysiloxane, molecular-chain-on-both-terminals trimethylsiloxy group-blocked methyl phenylpolysiloxane, molecular-chain-on-both-terminals trimethylsiloxy group-blocked dimethyl siloxane-methyl phenylsiloxane copolymer, molecular-chain-on-both-terminals trimethylsiloxy group-blocked diphenylpolysiloxane, molecular-chain-on-both-terminals trimethylsiloxy group-blocked dimethyl siloxane-diphenylsiloxane copolymer, trimethyl pentaphenyltrisiloxane, phenyl (trimethyl siloxy) siloxane, molecular-chain-on-both-terminals trimethylsiloxy group-blocked methyl alkyl polysiloxane, molecular-chain-on-both-terminals trimethylsiloxy group-blocked dimethyl polysiloxane-methyl alkyl siloxane copolymer, molecular-chain-on-both-terminals trimethylsiloxy group-blocked dimethyl siloxane-methyl (3,3,3-trifluoropropyl) siloxane copolymer, α,ω-dihydroxy polydimethyl siloxane, α,ω-diethoxypolydimethyl siloxane, 1,1,1,3,5,5,5-heptamethyl-3-octyl trisiloxane, 1,1,1,3,5,5,5-heptamethyl-3-dodecyl trisiloxane, 1,1,1,3,5,5,5-heptamethyl-3-hexadecyl trisiloxane, tristrimethyl siloxymethylsilane, tristrimethyl siloxyalkylsilane, tetrakistrimethyl cyloxysilane, tetramethyl-1,3-dihydroxy disiloxane, octamethyl-1,7-dihydroxy tetrasiloxane, hexamethyl-1,5-diethoxytrisiloxane, hexamethyl disiloxane, octamethyl trisiloxane, alkyl modified silicone, higher alkoxy modified silicone, and higher fatty acid modified silicone.

As non-polar organic compounds and low-polar organic compounds, hydrocarbon oil and fatty acid ester oil are preferably used. These components are widely used particularly for base materials of cosmetics, examples of these oil agents include one or two or more types selected from known vegetable oils, animal oils, higher alcohols, fatty acid triglyceride, synthetic sebum, and fluorinated oil.

These oil agents are the same as those described in paragraphs 0130 to 0135, 0206, for example, of Patent Document WO2011/049248. Examples of the fluorinated oil may include perfluoropolyether, perfluorodecalin, and perfluorooctane.

[Compositions Containing Water or the Like]

The organopolysiloxane or acid-neutralized salt thereof according to the present invention is a special oil agent having surface activity function or water solubility, having good affinity with polar solvents such as water and at least one type of alcohols selected from lower alcohols and polyhydric alcohols, and capable of forming stable aqueous compositions or W/O emulsion.

The water used needs to contain no component harmful to the human body and be clean, and examples thereof may include tap water, purified water, mineral water, and deep ocean water.

Typical examples of the lower alcohols and the polyhydric alcohols include ethanol, isopropanol, 1,3-butylene glycol, sorbitol, dipropylene glycol, propylene glycol, glycerin, and polyethylene glycol, which are capable of enhancing stability of emulsion. In particular, ethanol is a general-use solvent, and preferable examples thereof include 1,3-butylene glycol, sorbitol, dipropylene glycol, propylene glycol, glycerin, polyethylene glycol, which are preferable for their moisturizing action.

By providing the organopolysiloxane according to the present invention in the form of acid-neutralized salt through the above-described ionic management, solubility to the aqueous phase can be dramatically improved, whereby stable water-based compositions can be formed.

The organopolysiloxane or acid-neutralized salt thereof according to the present invention forms W/O emulsion by mixing the above-described oil agents, water, and the like, using mechanical power with devices such as a homomixer, a paddle mixer, a Henschel mixer, a homodisper, a colloid mill, a propeller agitator, a homogenizer, in-line type continuous emulsifier, an ultrasonic emulsifier, and a vacuum kneader. The organopolysiloxane according to the present invention is PEG-free silicone, has comparatively low viscosity, forms easy-to-handle oil-based compositions, and is advantageous when forming W/O emulsion in that it provides higher viscosity and more stable emulsion than polyether-based silicone does.

<Preparation for External Use/Cosmetic>

The organopolysiloxane or acid-neutralized salt thereof that can be obtained with the method of production according to the present invention can be suitably formulated to be a preparation for external use or a cosmetic, and thus can form the preparation for external use or the cosmetic according to the present invention. A raw material for the preparation for external use and the cosmetic including the organopolysiloxane or acid-neutralized salt thereof obtained with the method of production according to the present invention may be manufactured, and compounded into the preparation for external use or the cosmetic.

The organopolysiloxane or acid-neutralized salt thereof according to the present invention can be used for an application that is the same as those of the co-modified organopolysiloxane described in Patent Document (WO2011/049248), Patent Document (WO2011/049247), and Patent Document (JP-A-2012-046507), or novel organopolysiloxane copolymer described in Patent Document (WO2011/049246), depending on the structure and the functional group of the organopolysiloxane or acid-neutralized salt thereof. The organopolysiloxane or acid-neutralized salt thereof according to the present invention can be used in a manner similar to that in the case of the organopolysiloxane described in these Patent Documents, for a combination with any cosmetic raw material component and a preparation for external use, in particular, for a dosage forms, types and formulation examples of cosmetics, and can be compounded into various cosmetics.

The preparation for external use according to the present invention is not particularly limited, as long as the composition thereof is applicable as a cosmetic or medicine for a human body. Specific examples of the product of the cosmetic according to the present invention include: skin cosmetic products such as skin cleansing products, skin care products, makeup products, antiperspirant products, and ultraviolet protection products; hair cosmetic products such as hair cleanser products, hair styling products, hair coloring products, hair tonic products, hair rinse products, hair conditioner products, and hair treatment products; and bathing cosmetics. Examples of the medicine according to the present invention include hair regrowth agent, hair growth agent, analgesic agent, fungicide, anti-inflammatory agent, refreshing agent, and skin aging inhibitor. Note that the cosmetic and the medicine are not limited to these.

The preparation for external use is used for the skin, nail, hair, and the like of a human body, and may have a medical active ingredient to be used for treating various diseases for example. The cosmetic is also used for the skin, nail, hair, and the like of a human body, but is focused on cosmetic purposes. Preferably, the preparation for external use or the cosmetic is antiperspirant, skin cleanser, skin preparation for external use skin cosmetic, hair cleanser, hair preparation for external use, or a hair cosmetic.

The antiperspirant, the skin cleanser, the skin preparation for external use, or the skin cosmetic according to the present invention includes the organopolysiloxane or acid-neutralized salt thereof according to the present invention, and the form thereof, which is not limited, may include a solution form, an emulsion form, a cream form, a solid form, a semi-solid form, a paste form, a gel form, a powder form, a multilayer form, a mousse form, or water-in-oil/oil-in-water emulsion composition. Specific examples of the skin preparation for external use or the skin cosmetic according to the present invention include lotions, emulsions, creams, sunscreen emulsions, sunscreen creams, hand creams, cleansing compositions, massage lotions, cleansing agents, antiperspirants, deodorants, and other basic cosmetic products; foundations, make-up bases, blushers, rouges, eye shadows, eye liners, mascaras, nail enamels, and other make-up cosmetic products; and the like.

Similarly, the hair cleanser, the hair preparation for external use, or the hair cosmetic according to the present invention includes the organopolysiloxane or acid-neutralized salt thereof according to the present invention and may be in various forms to be used. For example, the hair cosmetics may be used after dissolving or dispersing in an alcohol, a hydrocarbon, a volatile cyclic silicone, or the like, or cab be used in the form of an emulsion by dispersing in water using an emulsifier. Furthermore, the cosmetic can be used as a spray by using propane, butane, trichloromonofluoromethane, dichlorodifluoromethane, dichlorotetrafluoroethane, carbonic acid gas, nitrogen gas, or other propellant. Examples of other forms include emulsion form, a cream form, a solid form, a semisolid form, a paste form, a gel form, a powder form, a multilayer form, and a mousse form. Various forms thereof can include shampooing agents, rinsing agents, conditioning agents, setting lotions, hair sprays, permanent wave agents, mousses, hair colorants, and the like.

The preparation for external use or the cosmetic of the present invention can optionally add, to an extent that will not impair the advantageous effects of the present invention, components used in normal preparations for external use or cosmetics, water, powders or coloring agents, alcohols, water-soluble polymers, film-forming agents, oil agents, oil-soluble gelling agents, organo-modified clay minerals, surfactants, resins, UV absorbers, salts, moisturizing agents, preservatives, antibacterial agents, fragrances, salts, antioxidants, pH adjusters, chelating agents, refreshing agents, anti-inflammatory agents, skin beautifying components (whitening agents, cell activating agents, skin roughness improving agents, blood circulation promoters, skin astringents, antiseborrheic agents, and the like), vitamins, amino acids, nucleic acids, hormones, clathrate compounds, and the like; bioactive substances, medically effective components, and fragrances, and these are not particularly limited.

[Powder or Colorant]

Powder or a colorant that can be used for the cosmetic or the preparation for external use according to the present invention is a component generally used in cosmetics, and includes white and colored pigments as well as extender pigments. The white and colored pigments are used for purposes such as coloring the cosmetic. The extender pigments are used for purposes such as feel improvement form cosmetics. As the "powder" according to the present invention, the white and colored pigments as well as the extender pigments, generally used for cosmetics, can be used in a non-limiting manner. In the present invention, one or a plurality of types of powder is preferably compounded. The particle shape (such as spherical, rod-like, needle-like, plate-like, indefinite shape, spindle shape, cocoon shape, etc.), particle size (fumed shape, fine particle, pigment grade etc.) and particle structure (porous, non-) are not particularly limited. Still, the average primary particle diameter is preferably in a range from 1 nm to 100 µm. In particular, when the powder or the colorant is compounded as a pigment, one or a plurality of types of powder selected from inorganic pigment powder, organic pigment powder, and resin powder with the average particle diameter in a range from 1 nm to 20 µm is preferably compounded.

Examples of the powder include inorganic powder, organic powder, surfactant metal salt powder (metal soap), colored pigment, pearl pigment, metal powder pigment, a combination of these, and a matter obtained by performing a water repellent treatment on the surfaces of these.

Specific examples include the same powders or colorants recited in paragraphs 0150 to 0152 of Patent Document (WO/2011/049248, filed by the present applicant).

Of the powders recited, description of a silicone elastomer powder shall be given. The silicone elastomer powder is a crosslinked product of a straight diorganopolysiloxane formed principally from diorganosiloxy units (D units), and can be preferably obtained by crosslinking an organohydrogenpolysiloxane having a silicon-bonded hydrogen atom on the sidechain or the molecular terminal and a diorganopolysiloxane having an unsaturated hydrocarbon group such as an alkenyl group or the like on the sidechain or the molecular terminal, in the presence of a hydrosilylation reaction catalyst. Compared to a silicone resin powder formed from T units and Q units, the silicone elastomer powder is soft, has elasticity, and has superior oil absorbency.

Therefore, oils and fats on the skin can be absorbed and makeup smearing can be prevented. In addition, by carrying out surface treatment using the organopolysiloxane or an acid-neutralized product thereof according to the present invention, which can provide efficient and homogeneous treatment, it is possible to improve the dispersion stability of the powder in the overall cosmetic and obtain a cosmetic that is stable over time.

The silicone elastomer powder can be in various forms such as spherical, flat, amorphous, or the like. The silicone elastomer powder may also be in the form of an oil dispersion. With the cosmetic of the present invention, the silicone elastomer powder is particulate in form, and the primary particle size observed using an electron microscope and/or the average primary particle size measured by laser analysis or scattering is in a range from 0.1 to 50 µm. Additionally, a silicone elastomer powder having spherical primary particles can be preferably compounded. The silicone elastomer that constitutes the silicone elastomer powder is preferably one having a hardness, as measured using a type A durometer in the "Rubber, Vulcanized or Thermoplastic-Determination of Hardness" specified in JIS K 6253, of 80 or lower, and more preferably 65 or lower.

Of these silicone elastomer powders, specific examples of silicone elastomer spherical powders are the same as those disclosed by the applicants in paragraph [0168] of the above-mentioned Patent Document (WO/2011/049248), and may be a silicone elastomer powder that has been subjected to a variety of water-repellent treatments, as disclosed in paragraphs [0150] to [0152].

The cosmetic or preparation for external use of the present invention can further comprise other surfactants. These other surfactants are components that function as cleansing components of the skin or the hair or, alternatively, as the oil agent or an emulsifier, and can be selected as desired depending on the type and function of the cosmetic. More specifically, the other surfactants can be selected from the group consisting of an anionic surfactant, a cationic surfactant, a nonionic surfactant, an amphoteric surfactant, and a semipolar surfactant. Preferably a silicone-based nonionic surfactant is used in combination.

These surfactants are the same as those disclosed by the applicants in paragraphs [0162], [0163] and [0195] to [0201] and so on in the above-mentioned Patent Document (WO/2011/049248). The organopolysiloxane or an acid-neutralized product thereof according to the present invention has a polar group and a non-polar group in the molecule and, therefore, has functionality as a dispersing agent. Thus, in cases where used in combination with a nonionic surfactant, the component functions as an aid to enhance the stability of the nonionic surfactant and may improve overall stability of the formulation. Particularly, the organopolysiloxane or an acid-neutralized product thereof according to the present invention or a solution containing the organopolysiloxane or an acid-neutralized product thereof according to the present invention has improved compatibility and affinity with various types of modified silicones, and thus is preferably used in combination with polyoxyalkylene-modified silicones, polyglyceryl-modified silicones, glyceryl-modified silicones, sugar modified silicones and sugar alcohol-modified silicones. Moreover, the silicone-based nonionic surfactants described above in which an alkyl branch, a straight chain silicone branch, a siloxane dendrimer branch, or the like is (as desired) provided with the hydrophilic group can be advantageously used.

Depending on the purpose thereof, the cosmetic or the preparation for external use of the present invention can comprise one or two or more polyhydric alcohols and/or lower monohydric alcohols as a component. These alcohols are the same as those disclosed by the applicants in paragraphs [0159] and [0160] and the like in the above-mentioned Patent Document (WO/2011/049248).

Depending on the purpose thereof, the cosmetic or the preparation for external use of the present invention can comprise one or two or more inorganic salts and/or organic salts as a component. These salts are the same as those disclosed by the applicants in paragraph [0161] and the like in the above-mentioned Patent Document (WO/2011/049248).

Depending on the purpose thereof, the cosmetic or the preparation for external use of the present invention can include at least one selected from the group consisting of a crosslinking organopolysiloxane, an organopolysiloxane elastomer spherical powder, a silicone resin, an acryl silicone dendrimer copolymer, a silicone raw rubber, a polyamide-modified silicone, an alkyl-modified silicone wax, and an alkyl-modified silicone resin wax as a component. These silicone components are the same as those disclosed in paragraphs [0162] to [0194] and the like in the above-mentioned Patent Document (WO/2011/049248).

Depending on the purpose thereof, the cosmetic or the preparation for external use of the present invention can include one or two or more types of water soluble polymers. The water soluble polymers are the same as those disclosed in the paragraph [0201] and the like in Patent Document (WO/2011/049248).

Depending on the purpose thereof, the cosmetic or the preparation for external use of the present invention can include one or two or more ultraviolet light blocking components as a component. These ultraviolet light blocking components are the same as the organic and inorganic ultraviolet light blocking components disclosed by the applicants in paragraphs [0202] to [0204] and the like in Patent Document (WO/2011/049248) and in paragraphs [0223] to [0225] and the like in Patent Document (WO/2013/100207). The ultraviolet light blocking components that can be used particularly preferably include at least one type selected from among the group comprising fine particulate titanium oxide, fine particulate zinc oxide, paramethoxy cinnamic acid 2-ethylhexyl, 4-tert-butyl-4'-methoxydibenzoylmethane, diethylamino hydroxybenzoyl hexyl benzoate, benzotriazole-based ultraviolet radiation absorbers, and triazine-based ultraviolet radiation absorbers such as 2,4,6-tris[4-(2-ethylhexyloxycarbonyl)anilino]1,3,5-triazine {INCI: octyl triazone}, 2,4-bis{[4-(2-ethyl-hexyloxy)-2-hydroxy]phenyl}-6-(4-methoxyphenyl)-1,3,5-triazine {(INCI: bis-ethylhexyloxyphenol methoxyphenyltriazine (product name: Tinosorb S™)}. These ultraviolet light blocking components are generally used, are easy to acquire, and have high ultraviolet light blocking effects and, thus can be beneficially used. In particular, using both inorganic and organic ultraviolet light blocking components is preferable, and using a UV-A blocking component in combination with a UV-B blocking component is more preferable.

In the cosmetic or the preparation for external use of the present invention, by using the organopolysiloxane or an acid-neutralized product thereof according to the present invention and the ultraviolet light blocking component together, the ultraviolet light blocking component can be stably dispersed in the cosmetic and the tactile sensation and the storage stability of the entire cosmetic can be improved. Therefore, superior UV blocking capacity can be imparted to the cosmetic.

Various components other than the components described above can be used in the cosmetic of the present invention, provided that such use does not impair the effects of the present invention. Examples thereof include oil-soluble gelling agents, organo-modified clay minerals, preservatives, bioactive components, skin beautifying components, pH adjusting agents, antioxidants, solvents, chelating agents, moisturizing components, perfumes, and the like. These optional cosmetic product components are the same as those disclosed in paragraphs [0207], [0208] and [0220] to [0228] and the like in the above-mentioned Patent Document (WO/2011/049248).

Additionally, in cases where the cosmetic or the preparation for external use according to the present invention is an anti-perspirant, or depending on the purpose of the cosmetic, the cosmetic can contain an anti-perspiration active component and/or a deodorant agent. These anti-perspiration components and deodorant components are the same as those disclosed by the applicants in paragraphs [0209] to [0219] and the like in Patent Document (WO/2011/049248). Similarly, in cases in which the cosmetic or the preparation for external use according to the present invention is an anti-perspirant composition, the preparation and method of use of the various anti-perspirant compositions are the same as those disclosed by the applicants in paragraphs [0234] to [0275] and the like of Patent Document (WO/2011/049248).

INDUSTRIAL APPLICABILITY

The organopolysiloxane or acid-neutralized salt thereof according to the present invention features surface activity performance that is equal to or higher than conventional non-ionic hydrophilic silicones such as polyether modified silicone, sugar modified silicone, and glycerin modified silicone, and further features a unique property of enabling ionic management and viscosity management which has been difficult with the conventional non-ionic hydrophilic silicones. Furthermore, organopolysiloxane or acid-neutralized salt thereof can be obtained with a raw material that is inexpensive and easy to obtain, and thus high purity organopolysiloxane or acid-neutralized salt thereof can be easily obtained at a low cost. Thus, high yield or productivity can be achieved, so that production on a commercial scale would not be so difficult. High purity organopolysiloxane or acid-neutralized salt thereof obtained with the method of production according to the present invention has an impurity derived from an organic modifier removed, and thus substantially consists of a single component. Thus, the organopolysiloxane or acid-neutralized salt thereof is less likely to involve phase separation, sedimentation of an unreacted material, and the like after the manufacturing. Thus, a stable production step can be achieved with no performance deterioration, quality change, or the like due to a poor compatibility between the main component and impurity. Furthermore, the organopolysiloxane or acid-neutralized salt thereof is less susceptible to deterioration due to oxidation, and thus can not only achieve a stable production step, but can also achieve a higher quality level of the end product. All things considered, the present invention provides novel and high purity organopolysiloxane or acid-neutralized salt thereof that could not have been obtained with conventional methods, and thus can provide many technical advantages that could not have been achieved by conventional non-ionic hydrophilic silicones.

Specifically, the organopolysiloxane according to the present invention or an acid-neutralized product thereof obtained by the present invention can be suitable used as a raw material for preparation for external use, medicine, or cosmetic, and can also be used for various other purposes.

Examples of such purposes include a fiber treatment agent, varnishes or coating additives having superior heat resistance, weather resistance, or electrical properties; foam stabilizers or modifying agents for polyol base compounds used in various urethane and foam materials; debonding agents or release agents; antifoaming agents; grease or oil compounds; modifying agents, additives, or surface treatment agents use for oil, rubber, or resin of insulating, glazing, water repelling, heating mediums, cooling mediums, and lubricants; compounds, modifying agents, and precursors for silane coupling agents; coating materials or sealing materials for buildings or linings; protective agents, lubricants, or buffer agents for fiber optics and electrical wiring; and a raw material for a general industrial material such as an electronic/electric parts.

EXAMPLES

The present invention will be described below using examples, but the present invention is not limited thereto. In the following compositional formulae, "M" represents a $Me_3SiO$ group (or a $Me_3Si$ group), "D" represents a $Me_2SiO$ group, "$M^H$" represents a $Me_2HSiO$ group (or a $Me_2HSi$ group), "$D^H$" represents a MeHSiO group, and $M^R$ and $D^R$ respectively represent units in which a methyl group in "M" or "D" is modified by any substituent. Additionally, in the production examples, "IPA" represents isopropyl alcohol, and AGE allyl glycidyl ether.

(Example 1) <Production of Silicone Compound No. 1>

Step 1: Synthesis (Hydro Silylation) of Intermediate and Purification (General Stripping)

First, 152.5 g of a methyl hydrogen polysiloxane represented by the average composition formula $MD_{43.7}D^H{}_{7.4}M$ and 9.6 g of allyl glycidyl ether (AGE) were placed in a 500-ml separable flask, and were soaked in an oil bath and heated to 40° C. while stirring under a nitrogen stream. Then, 0.02 ml of a platinum-1,3-divinyl-1,1,3,3-tetramethyl disiloxane complex catalyst solution (Pt concentration: 4.4 wt %) was added, the resultant mixture was heated to 70 to 80° C., and a reaction was performed for 2 hours.

Next, a small amount of the reaction liquid was collected, and when the reaction rate was confirmed by an alkali decomposition gas generation method (the remaining Si—H groups are decomposed using a KOH ethanol/water solution, and the reaction rate was calculated from the volume of the produced hydrogen gas), the reaction was found to reach the target. After the liquid inside the flask was cooled to 50 to 55° C., about 3 g each of 1-hexene was put in the flask seven times (21.5 g in total), such that the reaction gradually proceeded while avoiding bumping due to reaction heat. In this process, 0.02 ml of the catalyst solution was added when heat generation became slower. It took about 1 hour to put the entire amount of 1-hexene in the flask. After aging at 55 to 65° C. was performed for 1.5 hours, it was confirmed with the same method that the reaction rate showed the completion of the reaction. The reaction liquid was maintained at 145 to 160° C. and under reduced pressure of 6 to 8 mmHg for 2 hours, the low-boiling portion containing the remaining AGE was completely distilled away, whereby an epoxy modified silicone intermediate represented by the average composition formula $MD_{43.7}D^{R*21}{}_{2.1}D^{R*11}{}_{5.3}M$ was obtained as a light brown, transparent liquid.

In the formula, $R^{*21}$ and $R^{*11}$ are as follows.

$R^{*21}$=—$C_3H_6OCH_2CH(O)CH_2$ $R^{*11}$=—$C_6H_{13}$

Step 2: Inventive Synthesis (Secondary Amino Alcohol Added) and Removal of Low-Boiling Portion After the liquid inside the flask was cooled and the pressure was recovered, while stirring under a nitrogen stream, a solution containing 16.7 g of diisopropanolamine (DIPA), 3.3 g of ion exchanged water, and 40 g of IPA was added, and aging at 75 to 85° C. was performed four 4 hours. Next, the flask was heated to 110 to 145° C. under normal pressure to completely distill IPA and water, and the resultant distillate in a receptor was removed thereafter.

Step 3: Removal of High-Boiling Portion (Reinforced Stripping)

The upper cap and the entire body from the connecting tube to the distillation head of the separable flask were closely wrapped in aluminum foil for heat retention, and a ribbon heater was wound around the portion from the connecting tube to the distillation head, and the entire structure was closely wrapped in aluminum foil to avoid cooling by the external air.

The ribbon heater was set to 130° C. and the oil bath was set to 170° C., and while stirring under a nitrogen stream, the pressure inside the flask was reduced to 6 to 9 mmHg. When the temperature of the liquid inside the flask reached 150 to 170° C. and the temperature at the head portion reached 110 to 130° C., distillation of the remaining DIPA gradually started. This state was maintained for 3 hours, from the flask top to the end of the distillation head were completely dried, and no additional distillation occurred. The temperature of the oil bath was lowered for cooling to 70° C. and then the pressure was recovered, whereby 182.7 g of tertiary-amine structure-containing polyhydric alcohol modified silicone represented by the average composition formula $MD_{43.7}D^{R*41}{}_{2.1}D^{R*11}{}_{5.3}M$ was obtained as a light brown, substantially transparent liquid.

In the formula, $R^{*41}$ and $R^{*11}$ are as follows.

$R^{*41}$=—$C_3H_6$—$OCH_2CH(OH)CH_2$—$N\{CH_2CH(CH_3)$—$OH\}_2$ $R^{*11}$=—$C_6H_{13}$

Step 4: Filtration

Since contamination due to silicone grease used for the ground glass joint of the separable flask was thought to cause some cloudiness in the appearance of the reaction product, filtration was performed using an activated-carbon-carrying depth filter. As a result, 158 g of a light brown, completely transparent liquid was obtained.

(Example 2) <Production of Silicone Compound No. 2>

Step 1: Synthesis (Hydro Silylation) of Intermediate and Purification (General Stripping)

First, 157.1 g of a methyl hydrogen polysiloxane represented by the average composition formula $MD_{43.7}D^H{}_{7.4}M$ and 9.9 g of AGE were placed in a 500-ml separable flask, and were soaked in an oil bath and heated to 40° C. while stirring under a nitrogen stream. Then, 0.02 ml of a platinum-1,3-divinyl-1,1,3,3-tetramethyl disiloxane complex catalyst solution (Pt concentration: 4.4 wt %) was added, the resultant mixture was heated to 70 to 80° C., and a reaction was performed for 2 hours. Next, a small amount of the reaction liquid was sampled, and it was confirmed by an alkali decomposition gas generation method that the target reaction rate had been achieved. After the liquid inside the flask was cooled to 40° C., about 3.1 g each of 1-hexene was put in the flask seven times (22.0 g in total), such that the reaction gradually proceeded while avoiding bumping due to reaction heat. In this process, 0.01 ml of the catalyst solution was added when heat generation became slower. It took about 1 hour to put the entire amount of 1-hexene in the flask. After aging at 55 to 65° C. was performed for 1 hour, it was confirmed with the same method that the reaction rate showed the completion of the reaction. The reaction liquid was maintained at 160 to 170° C. and under reduced pressure of 1 to 6 mmHg for 1 hour, the low-boiling portion containing the remaining AGE was completely distilled away, whereby an epoxy modified silicone intermediate represented by the average composition formula $MD_{43.7}D^{R*21}{}_{2.1}D^{R*11}{}_{5.3}M$ was obtained as a light yellow, transparent liquid.

In the formula, $R^{*21}$ and $R^{*11}$ are as follows.

$R^{*21}$=—$C_3H_6OCH_2CH(O)CH_2$ $R^{*11}$=—$C_6H_{13}$

Step 2: Inventive Synthesis (Secondary Amino Alcohol Added) and Removal of Low-Boiling Portion After the liquid inside the flask was cooled and the pressure was recovered, while stirring under a nitrogen stream, a solution containing 5.5 g of diisopropanolamine (DIPA), 1.4 g of ion exchanged water, and 40 g of IPA was added, and aging at 75 to 85° C. was performed for 4 hours. Furthermore, 5.1 g of N-methyl ethanolamine (MEA) was added, and aging was continued for 4.5 hours. The flask was heated to 130° C. under normal pressure to completely distill IPA and water, and the resultant distillate in a receptor was removed thereafter.

Step 3: Removal of High-Boiling Portion (Reinforced Stripping)

In the same manner as in Step 3 of Example 1, the ribbon heater was set to 130° C. and the oil bath was set to 160° C., and while stirring under a nitrogen stream, the pressure inside the flask was reduced to 2 to 6 mmHg. The liquid inside the flask was maintained in a state in which the temperature reached 150 to 160° C. and reached 130° C. at the head portion for 1.5 hours, from the flask top to the end of the distillation head were completely dried, and no additional distillation occurred. The pressure was recovered, and 187.0 g of tertiary-amine structure-containing polyhydric alcohol modified silicone represented by the average composition formula $MD_{43.7}D^{R*41}{}_{1.0}D^{R*42}{}_{1.1}D^{R*11}{}_{5.3}M$ was obtained as a light brown, substantially transparent liquid.

In the formula, $R^{*41}$, $R^{*42}$, and $R^{*11}$ are as follows.

$R^{*41}$=—$C_3H_6$—$CH_2CH(OH)CH_2$—$N\{CH_2CH(CH_3)$—$OH\}_2$ $R^{*42}$=—$C_3H_6$—$CH_2CH(OH)CH_2$—$N(CH_3)(CH_2CH_2OH)$ $R^{*11}$=—$C_6H_{13}$

Step 4: Filtration

Since contamination due to silicone grease used for the ground glass joint of the separable flask was thought to cause some cloudiness in the appearance of the reaction product, filtration was performed using an activated-carbon-carrying depth filter. As a result, 162 g of a slightly yellow, completely transparent liquid was obtained.

(Example 3) <Production of Silicone Compound No. 3>

Step 1: Synthesis (Hydro Silylation) of Intermediate and Purification (General Stripping)

First, 111.4 g of a methyl hydrogen polysiloxane represented by the average composition formula $MD_{37}D^{H}{}_{12.7}M$, 9.8 g of vinyl[tris(trimethylsiloxy)]silane represented by the average composition formula $CH_2$=CH—$Si(OSiMe_3)_3$, and 7.3 g of AGE were placed in a 500-ml separable flask, and were soaked in an oil bath and heated to 40° C. while stirring under a nitrogen stream. Then, 0.02 ml of a platinum-1,3-divinyl-1,1,3,3-tetramethyl disiloxane complex catalyst solution (Pt concentration: 4.4 wt %) was added, the resultant mixture was heated to 65 to 80° C., and a reaction was performed for 2 hours. Next, a small amount of the reaction liquid was sampled, and it was confirmed by an alkali decomposition gas generation method that the target reaction rate had been achieved. The temperature of the liquid inside the flask was set to 70° C., and 1-dodecen was put in the flask 3 times (66.2 g in total), such that the reaction gradually proceeded and the liquid temperature did not exceed 100° C. After heat generation became slower, 0.02 ml of the catalyst solution was added, and then aging at 70 to 100° C. was performed for 5 hours, and it was confirmed with the same method that the reaction rate showed the completion of the reaction. The reaction liquid was maintained at 130 to 160° C. and under reduced pressure of 1 to 3 mmHg for about 1 hour, the remaining AGE and the low-boiling portion including dodecen were completely distilled away, whereby an epoxy modified silicone intermediate represented by the average composition formula $MD_{37}D^{R*31}{}_{1.0}D^{R*21}{}_{2.1}D^{R*12}{}_{9.6}M$ was obtained as a light yellow brown, transparent liquid.

In the formula, $R^{*21}$, $R^{*12}$, and $R^{*31}$ are as follows.

$R^{*21}$=—$C_3H_6OCH_2CH(O)CH_2$ $R^{*12}$=—$C_{12}H_{25}$ $R^{*31}$=—$C_2H_4Si(OSiMe_3)_3$

Step 2: Inventive Synthesis (Secondary Amino Alcohol Added) and Removal of Low-Boiling Portion After the liquid inside the flask was cooled and the pressure was recovered, while stirring under a nitrogen stream, a solution containing 12.7 g of diisopropanolamine (DIPA), 2.4 g of ion exchanged water, and 40 g of IPA was added, and aging at 75 to 85° C. was performed for 4 hours. The flask was heated to 130° C. under normal pressure to completely distill IPA and water, and the resultant distillate in a receptor was removed thereafter.

Step 3: Removal of High-Boiling Portion (Reinforced Stripping)

In the same manner as in Step 3 of Example 1, the ribbon heater was set to 130° C. and the oil bath was set to 170° C., and while stirring under a nitrogen stream, the pressure inside the flask was reduced to 1 to 4 mmHg. The liquid inside the flask was maintained in a state in which the temperature reached 150 to 160° C. and reached 130° C. at the head portion for 3 hours, from the flask top to the end of the distillation head were completely dried, and no additional distillation occurred. After cooling to 40° C., the pressure was recovered, and 179.7 g of tertiary-amine structure-containing polyhydric alcohol modified silicone represented by the average composition formula $MD_{37}D^{R*31}{}_{1.0}D^{R*41}{}_{2.1}D^{R*12}{}_{9.6}M$ was obtained as a yellow brown, substantially transparent liquid.

In the formula, $R^{*41}$, $R^{*12}$, and $R^{*31}$ are as follows.

$R^{*41}$=—$C_3H_6$—$CH_2CH(OH)CH_2$—$N\{CH_2CH(CH_3)$—$OH\}_2$ $R^{*12}$=—$C_{12}H_{25}$ $R^{*31}$=—$C_2H_4Si(OSiMe_3)_3$

Step 4: Filtration

Since contamination due to silicone grease used for the ground glass joint of the separable flask was thought to cause some cloudiness in the appearance of the reaction product, filtration was performed using an activated-carbon-carrying depth filter. As a result, 154 g of a light brown, completely transparent liquid was obtained.

(Example 4) <Production of Silicone Compound No. 4>

Step 1: Synthesis (Hydro Silylation) of Intermediate and Purification (General Stripping)

First, 114.0 g of a methyl hydrogen polysiloxane represented by the average composition formula $MD^{37}D^{H}_{12.7}M$, 10.0 g of vinyl[tris(trimethylsiloxy)]silane represented by the average composition formula $CH_2=CH-Si(OSiMe_3)_3$, and 7.5 g of AGE were placed in a 500-ml separable flask, and were soaked in an oil bath and heated to 40° C. while stirring under a nitrogen stream. Then, 0.02 ml of a platinum-1,3-divinyl-1,1,3,3-tetramethyl disiloxane complex catalyst solution (Pt concentration: 4.4 wt %) was added, the resultant mixture was heated to 70 to 85° C., and a reaction was performed for 2 hours. Next, a small amount of the reaction liquid was sampled, and it was confirmed by an alkali decomposition gas generation method that the target reaction rate had been achieved. The temperature of the liquid inside the flask was set to 75° C., and 1-dodecen was put in the flask 3 times (66.8 g in total), such that the reaction gradually proceeded and the liquid temperature did not exceed 110° C. After heat generation was settled, 0.05 ml of the catalyst solution was added, aging at 75 to 95° C. was performed for 6 hours, and it was confirmed with the same method that the reaction rate showed the completion of the reaction. The reaction liquid was maintained at 130 to 160° C. and under reduced pressure of 3 mmHg for about 2 hours, the remaining AGE and the low-boiling portion including dodecen were completely distilled away, whereby an epoxy modified silicone intermediate represented by the average composition formula $MD^{37}D^{R*31}_{1.0}D^{R*21}_{2.1}D^{R*12}_{9.6}M$ was obtained as a light yellow brown, transparent liquid.

In the formula, $R^{*21}$, $R^{*12}$, and $R^{*31}$ are as follows.

$R^{*21}=-C_3H_6OCH_2CH(O)CH_2$

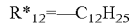
$R^{*12}=-C_{12}H_{25}$

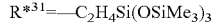
$R^{*31}=-C_2H_4Si(OSiMe_3)_3$

Step 2: Inventive Synthesis (Secondary Amino Alcohol Added) and Removal of Low-Boiling Portion After the liquid inside the flask was cooled and the pressure was recovered, while stirring under a nitrogen stream, a solution containing 6.6 g of diisopropanolamine (DIPA), 1.4 g of ion exchanged water, and 40 g of IPA were added, and aging at 65 to 80° C. was performed for 4 hours. Furthermore, 1.8 g of N-methyl ethanolamine (MEA) was added, and aging was continued for 3 hours. The flask was heated to 120° C. under normal pressure to completely distill IPA and water, and the resultant distillate in a receptor was removed thereafter.

Step 3: Removal of High-Boiling Portion (Specially Devised Stripping)

The upper cap and the entire body from the connecting tube to the distillation head of the separable flask were closely wrapped in aluminum foil for heat retention. The oil bath was set to 150 to 170° C., and while stirring under a nitrogen stream, the pressure inside the flask was reduced to 1 to 6 mmHg. The liquid inside the flask was maintained in a state in which the temperature reached 150 to 170° C. for 4 hours, from the flask top to the cap were completely dried, and distillation was stopped. After cooling to 80° C., the pressure was recovered, and 183.2 g of tertiary-amine structure-containing polyhydric alcohol modified silicone represented by the average composition formula $MD^{37}D^{R*31}_{1.0}D^{R*41}_{1.6}D^{R*42}_{0.5}D^{R*12}_{9.6}M$ was obtained as a yellow brown, substantially transparent liquid.

In the formula, $R^{*41}$, $R^{*42}$, $R^{*12}$, and $R^{*31}$ are as follows.

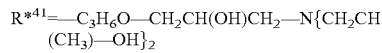
$R^{*41}=-C_3H_6O-CH_2CH(OH)CH_2-N\{CH_2CH(CH_3)-OH\}_2$

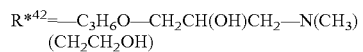
$R^{*42}=-C_3H_6O-CH_2CH(OH)CH_2-N(CH_3)(CH_2CH_2OH)$

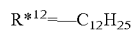
$R^{*12}=-C_{12}H_{25}$

$R^{*31}=-C_2H_4Si(OSiMe_3)_3$

Step 4: Filtration

Since contamination due to silicone grease used for the ground glass joint of the separable flask was thought to cause some cloudiness in the appearance of the reaction product, filtration was performed using an activated-carbon-carrying depth filter. As a result, 157 g of a light brown, completely transparent liquid was obtained.

(Example 5) <Production of Silicone Compound No. 5>

Step 1: Synthesis (Hydro Silylation) of Intermediate and Purification (General Stripping)

First, 167.1 g of a methyl hydrogen polysiloxane represented by the average composition formula $MD_{44.5}D^{H}_{2.1}M$ and 13.6 g of AGE were placed in a 500-ml separable flask, and were soaked in an oil bath and heated to 40° C. while stirring under a nitrogen stream. Then, 0.03 ml of a platinum-1,3-divinyl-1,1,3,3-tetramethyl disiloxane complex catalyst solution (Pt concentration: 4.4 wt %) was added, the resultant mixture was heated to 70 to 85° C., and a reaction was performed for 4 hours. Next, a small amount of the reaction liquid was sampled, and it was confirmed with the reaction rate examined by an alkali decomposition gas generation method that the reaction had been completed. The reaction liquid was maintained at 150 to 160° C. and under reduced pressure of 1 to 2 mmHg for 2.5 hours, the low-boiling portion containing the remaining AGE was completely distilled away, whereby an epoxy modified silicone intermediate represented by the average composition formula $MD_{44.5}D^{R*21}_{2.1}M$ was obtained as a light yellow, transparent liquid.

In the formula, $R^{*21}$ are as follows.

$R^{*21}=-C_3H_6OCH_2CH(O)CH_2$

Step 2: Inventive Synthesis (Secondary Amino Alcohol Added) and Removal of Low-Boiling Portion After the liquid inside the flask was cooled and the pressure was recovered, while stirring under a nitrogen stream, a solution containing 19.6 g of diisopropanolamine (DIPA), 3.6 g of ion exchanged water, and 40 g of IPA was added, and aging at 75 to 85° C. was performed for 4 hours. Next, the flask was heated to 130° C. under normal pressure to completely distill IPA and water, and the resultant distillate in a receptor was removed thereafter.

Step 3: Removal of High-Boiling Portion (Reinforced Stripping)

In the same manner as in Step 3 of Example 1, the ribbon heater was set to 130° C. and the oil bath was set to 170° C., and while stirring under a nitrogen stream, the pressure inside the flask was reduced to 3 to 6 mmHg. The liquid inside the flask was maintained in a state in which the temperature reached 150 to 160° C. and reached 130° C. at the head portion for 3.5 hours, from the flask top to the end of the distillation head were completely dried, and no additional distillation occurred. After cooling to 110° C., the pressure was recovered, and 186.9 g of tertiary-amine structure-containing polyhydric alcohol modified silicone represented by the average composition formula $MD_{44.5}D^{R*41}{}_{2.1}M$ was obtained as a light yellow brown, semitransparent liquid.

In the formula, $R^{*41}$ is as follows.

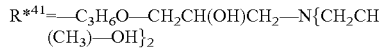

$R^{*41}=\!\!-\!C_3H_6O\!\!-\!\!CH_2CH(OH)CH_2\!\!-\!\!N\{CH_2CH(CH_3)\!\!-\!\!OH\}_2$

Step 4: Filtration

Since contamination due to silicone grease used for the ground glass joint of the separable flask was thought to cause cloudiness in the appearance of the reaction product, filtration was performed using an activated-carbon-carrying depth filter. As a result, 157 g of a colorless, completely transparent liquid was obtained.

(Example 6) <Production of Silicone Compound No. 6>

Step 1: Synthesis (Hydro Silylation) of Intermediate and Purification (General Stripping)

First, 167.1 g of a methyl hydrogen polysiloxane represented by the average composition formula $MD_{44.5}D^{H}{}_{2.1}M$ and 14.1 g of AGE were placed in a 500-ml separable flask, and were soaked in an oil bath and heated to 40° C. while stirring under a nitrogen stream. Then, 0.05 ml of a platinum-1,3-divinyl-1,1,3,3-tetramethyl disiloxane complex catalyst solution (Pt concentration: 4.4 wt %) was added, the resultant mixture was heated to 70 to 85° C., and a reaction was performed for 6.5 hours. Next, a small amount of the reaction liquid was sampled, and it was confirmed with the reaction rate examined by an alkali decomposition gas generation method that the reaction had been completed. The reaction liquid was maintained at 150 to 165° C. and under reduced pressure of 1 mmHg for about 1 hour, the low-boiling portion containing the remaining AGE was completely distilled away, whereby an epoxy modified silicone intermediate represented by the average composition formula $MD_{44.5}D^{R*21}{}_{2.1}M$ was obtained as a light yellow, transparent liquid.

In the formula, $R^{*21}$ are as follows.

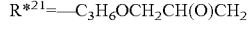

$R^{*21}=\!\!-\!C_3H_6OCH_2CH(O)CH_2$

Step 2: Inventive Synthesis (Secondary Amino Alcohol Added) and Removal of Low-Boiling Portion After the liquid inside the flask was cooled and the pressure was recovered, while stirring under a nitrogen stream, a solution containing 6.5 g of diisopropanolamine (DIPA), 1.6 g of ion exchanged water, and 40 g of IPA was added, and aging at 70 to 85° C. was performed for 4 hours. Furthermore, 6.4 g of N-methyl ethanolamine (MEA) was added and aging was continued for 3 hours. Next, the flask was heated to 130° C. under normal pressure to completely distill IPA and water, and the resultant distillate in a receptor was removed thereafter.

Step 3: Removal of High-Boiling Portion (Reinforced Stripping)

In the same manner as in Step 3 of Example 1, the ribbon heater was set to 130° C. and the oil bath was set to 170° C., and while stirring under a nitrogen stream, the pressure inside the flask was reduced to 3 to 6 mmHg. The liquid inside the flask was maintained in a state in which the temperature reached 160° C. and reached 130° C. at the head portion for 4.5 hours, from the flask top to the end of the distillation head were completely dried, and no additional distillation occurred. After cooling to 90° C., the pressure was recovered, and 182.5 g of tertiary-amine structure-containing polyhydric alcohol modified silicone represented by the average composition formula $MD_{44.5}D^{R*41}{}_{1.0}D^{R*42}{}_{1.1}M$ was obtained as a brown, semitransparent liquid.

In the formula, $R^{*41}$ and $R^{*42}$ are as follows.

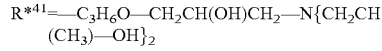

$R^{*41}=\!\!-\!C_3H_6O\!\!-\!\!CH_2CH(OH)CH_2\!\!-\!\!N\{CH_2CH(CH_3)\!\!-\!\!OH\}_2$

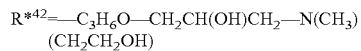

$R^{*42}=\!\!-\!C_3H_6O\!\!-\!\!CH_2CH(OH)CH_2\!\!-\!\!N(CH_3)(CH_2CH_2OH)$

Step 4: Filtration

Since contamination due to silicone grease used for the ground glass joint of the separable flask was thought to cause cloudiness in the appearance of the reaction product, filtration was performed using an activated-carbon-carrying depth filter. As a result, 157 g of a light brown, completely transparent liquid was obtained.

(Example 7) <Production of Silicone Compound No. 7>

Step 1: Synthesis (Hydro Silylation) of Intermediate and Purification (General Stripping)

First, 171.2 g of a methyl hydrogen polysiloxane represented by the average composition formula $MD_{44.5}D^{H}{}_{2.1}M$, 20.4 g of vinyl[tris(trimethylsiloxy)]silane represented by the average composition formula $CH_2\!\!=\!\!CH\!\!-\!\!Si(OSiMe_3)_3$, and 6.5 g of AGE were placed in a 500-ml separable flask, and were soaked in an oil bath and heated to 50° C. while stirring under a nitrogen stream. Then, 0.06 ml of a platinum-1,3-divinyl-1,1,3,3-tetramethyl disiloxane complex catalyst solution (Pt concentration: 4.4 wt %) was added, the resultant mixture was heated to 70 to 85° C., and a reaction was performed for 6 hours. Next, a small amount of the reaction liquid was sampled, and it was confirmed with the reaction rate examined by an alkali decomposition gas generation method that the reaction had been substantially completed. The reaction liquid was maintained at 150 to 160° C. and under reduced pressure of 1 mmHg for 1.5 hours, the low-boiling portion containing the remaining AGE was completely distilled away, whereby an epoxy modified silicone intermediate represented by the average composition formula $MD_{44.5}D^{R*31}{}_{1.1}D^{R*21}{}_{1.0}M$ was obtained as a substantially colorless, transparent liquid. In the formula, $R^{*21}$ and $R^{*31}$ are as follows.

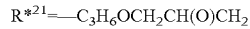

$R^{*21}=\!\!-\!C_3H_6OCH_2CH(O)CH_2$

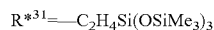

$R^{*31}=\!\!-\!C_2H_4Si(OSiMe_3)_3$

Step 2: Inventive Synthesis (Secondary Amino Alcohol Added) and Removal of Low-Boiling Portion After the liquid inside the flask was cooled and the pressure was recovered, while stirring under a nitrogen stream, 5.7 g of N-methyl ethanolamine (MEA) and 20 g of IPA were added, and aging at 75 to 85° C. was performed for 3 hours. Next, the flask was heated to 130° C. under normal pressure to completely distill IPA, and the resultant distillate in a receptor was removed thereafter.

Step 3: Removal of High-Boiling Portion (Reinforced Stripping)

In the same manner as in Step 3 of Example 1, the ribbon heater was set to 125° C. and the oil bath was set to 170° C., and while stirring under a nitrogen stream, the pressure inside the flask was reduced to 1 to 3 mmHg. The liquid inside the flask was maintained in a state in which the temperature reached 155 to 160° C. and reached 120° C. at the head portion for 3.5 hours, from the flask top to the end of the distillation head were completely dried, and no additional distillation occurred. After cooling to 80° C., the pressure was recovered, and 192.0 g of tertiary-amine structure-containing polyhydric alcohol modified silicone represented by the average composition formula $MD_{44.5}D^{R*31}{}_{1.0}D^{R*42}{}_{1.1}M$ was obtained as a brown, substantially transparent liquid.

In the formula, $R^{*42}$ and $R^{*31}$ are as follows.

$R^{*31}$=—$C_2H_4Si(OSiMe_3)_3$

Step 4: Filtration

Since contamination due to silicone grease used for the ground glass joint of the separable flask was thought to cause some cloudiness in the appearance of the reaction product, filtration was performed using an activated-carbon-carrying depth filter. As a result, 166 g of a light brown, completely transparent liquid was obtained.

(Example 8) <Production of Silicone Compound No. 8>

Step 1: Synthesis (Hydro Silylation) of Intermediate and Purification (General Stripping)

First, 117.5 g of a methyl hydrogen polysiloxane represented by the average composition formula $MD_{6.6}D^{H}{}_{2.8}M$ and 5.2 g of AGE were placed in a 500-ml separable flask, and were soaked in a 50° C. oil bath and heated to 42° C. while stirring under a nitrogen stream. Then, 0.015 ml of a platinum-1,3-divinyl-1,1,3,3-tetramethyl disiloxane complex catalyst solution (Pt concentration: 4.4 wt %) was added, and the temperature rose to 57° C. due to heat generation in the reaction. In this manner, about 5 g each of AGE was added four times (21.3 g in total) to the reaction system, such that the reaction gradually proceeded while the liquid temperature was maintained at or below 80° C. Next, 0.065 ml of the catalyst solution and 16.6 g of AGE were added 2 times, and aging at 70 to 80° C. was performed for 5 hours. A small amount of the reaction liquid was sampled, and it was confirmed with the reaction rate examined by an alkali decomposition gas generation method that the reaction had been substantially completed. The reaction liquid was maintained at 120 to 140° C. and under reduced pressure of 3 mmHg for about 1.5 hours, the low-boiling portion containing the remaining AGE was substantially completely distilled away, whereby an epoxy modified silicone intermediate represented by the average composition formula $MD_{6.6}D^{R*21}{}_{2.8}M$ was obtained as a yellow brown, substantially transparent liquid.

In the formula, $R^{*21}$ are as follows.

$R^{*21}$=—$C_3H_6OCH_2CH(O)CH_2$

Step 2: Inventive Synthesis (Secondary Amino Alcohol Added) and Removal of Low-Boiling Portion After the liquid inside the flask was cooled to 35° C. and the pressure was recovered, while stirring under a nitrogen stream, a solution containing 0.12 g of natural vitamin E, 63.2 g of diethanolamine (DEA), 47.5 g of IPA was added to the reaction system, and aging at 75 to 85° C. was performed for 4 hours. Next, the flask was heated to 130° C. under normal pressure to completely distill IPA, and the resultant distillate in a receptor was removed thereafter.

Step 3: Removal of High-Boiling Portion (Reinforced Stripping)

In the same manner as in Step 3 of Example 1, the ribbon heater was set to 130° C. and the oil bath was set to 170° C., and while stirring under a nitrogen stream, the pressure inside the flask was reduced to 1 mmHg. When the temperature of the liquid inside the flask reached 135° C. and the temperature at the head portion reached 110° C., distillation of DEA started. Furthermore, the internal liquid temperature was maintained at 150 to 160° C. and the temperature at the head portion was maintained at 125° C. for 3.5 hours, from the flask top to the end of the distillation head were completely dried, and no additional distillation occurred. After cooling to 70° C., the pressure was recovered, and 190.2 g of tertiary-amine structure-containing polyhydric alcohol modified silicone represented by the average composition formula $MD_{6.6}D^{R*43}{}_{2.8}M$ was obtained as a brown, semi-transparent viscous liquid.

In the formula, $R^{*43}$ is as follows.

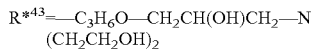

Step 4: Filtration

Since contamination due to silicone grease used for the ground glass joint of the separable flask was thought to cause cloudiness in the appearance of the reaction product, filtration was performed using an activated-carbon-carrying depth filter. As a result, 159 g of a colorless, completely transparent viscous liquid was obtained.

(Example 9) <Production of Silicone Compound No. 9>

Step 1: Synthesis (Hydro Silylation) of Intermediate and Purification (General Stripping)

First, 99.1 g of a methyl hydrogen polysiloxane represented by the average composition formula $MD_{6.6}D^{H}{}_{2.8}M$ and 23.4 g of vinyl[tris(trimethylsiloxy)]silane represented by the average composition formula $CH_2=CH—Si(OSiMe_3)_3$ were placed in a 500-ml separable flask, and were soaked in an oil bath and heated to 50° C. while stirring under a nitrogen stream. Then, 0.02 ml of a platinum-1,3-divinyl-1,1,3,3-tetramethyl disiloxane complex catalyst solution (Pt concentration: 4.4 wt %) was added, and a reaction was performed at 65 to 70° C. for about 50 minutes. Next, AGE was added twice (36.1 g in total), such that the reaction gradually proceeded while the reaction liquid temperature was maintained at or below 90° C. After 0.02 ml of the catalyst was added and aging was performed for 3 hours, a small amount of the reaction liquid was sampled, and it was confirmed by an alkali decomposition gas generation method that the target reaction rate had been achieved. The reaction liquid was maintained at 130 to 140° C. and under reduced pressure of 3 mmHg for about 2 hours, the low-boiling portion containing the remaining AGE was substantially completely distilled away, whereby an epoxy modified silicone intermediate represented by the average composition formula $MD_{6.6}D^{R*31}{}_{0.6}D^{R*21}{}_{2.2}M$ was obtained as a light yellow transparent liquid.

In the formula, $R^{*21}$ and $R^{*31}$ are as follows.

$R^{*21}$=—$C_3H_6OCH_2CH(O)CH_2$ $R^{*31}$=—$C_2H_4Si(OSiMe_3)_3$

Step 2: Inventive Synthesis (Secondary Amino Alcohol Added) and Removal of Low-Boiling Portion After the liquid inside the flask was cooled and the pressure was recovered, while stirring under a nitrogen stream, a solution containing 0.14 g of natural vitamin E, 42.6 g of diethanolamine (DEA), and 40 g of IPA was added to the reaction system, and aging at 70 to 85° C. was performed for 4 hours. Next, the flask was heated to 130° C. under normal pressure to completely distill IPA, and the resultant distillate in a receptor was removed thereafter.

Step 3: Removal of High-Boiling Portion (Reinforced Stripping)

In the same manner as in Step 3 of Example 1, the ribbon heater was set to 130° C. and the oil bath was set to 180° C., and while stirring under a nitrogen stream, the pressure inside the flask was reduced to 1 mmHg. When the temperature of the liquid inside the flask reached 155° C. and the temperature at the head portion reached 100° C., distillation of DEA started. Furthermore, the internal liquid temperature was maintained at 160 to 185° C. and the temperature at the head portion was maintained at 120° C. for 3.5 hours, from the flask top to the end of the distillation head were completely dried, and no additional distillation occurred. The pressure was recovered, and 165.3 g of tertiary-amine structure-containing polyhydric alcohol modified silicone represented by the average composition formula $MD_{6.6}D^{R*31}{}_{0.6}D^{R*43}{}_{2.2}MM$ was obtained as a light brown, substantially transparent viscous liquid.

In the formula, $R^{*43}$ and $R^{*31}$ are as follows.

$R^{*43}$=—$C_3H_6O$—$CH_2CH(OH)CH_2$—$N(CH_2CH_2OH)_2$ $R^{*31}$=—$C_2H_4Si(OSiMe_3)_3$

Step 4: Filtration

Since contamination due to silicone grease used for the ground glass joint of the separable flask was thought to cause some cloudiness in the appearance of the reaction product, filtration was performed using an activated-carbon-carrying depth filter. As a result, 135 g of a colorless, substantially transparent viscous liquid was obtained.

(Example 10) <Production of Silicone Compound No. 10>

Step 1: Synthesis (Hydro Silylation) of Intermediate and Purification (General Stripping)

First, 106.2 g of a methyl hydrogen polysiloxane represented by the average composition formula $MD_{6.6}D^H{}_{2.8}MM$ and 25.1 g of vinyl[tris(trimethylsiloxy)]silane represented by the average composition formula $CH_2$=CH—Si$(OSiMe_3)_3$ were placed in a 500-ml separable flask, and were soaked in an oil bath and heated to 50° C. while stirring under a nitrogen stream. Then, 0.02 ml of a platinum-1,3-divinyl-1,1,3,3-tetramethyl disiloxane complex catalyst solution (Pt concentration: 4.4 wt %) was added, and a reaction was performed at 55 to 75° C. for 4.5 hours. Next, AGE was added 2 times (38.6 g in total), such that the reaction gradually proceeded while the temperature of the reaction liquid was maintained at or below 95° C. After 0.02 ml of the catalyst was added and aging was performed for 2 hours, a small amount of the reaction liquid was sampled, and it was confirmed by an alkali decomposition gas generation method that the target reaction rate had been achieved. The reaction liquid was maintained at 120 to 140° C. and under reduced pressure of 5 to 6 mmHg for about 1 hour, the low-boiling portion containing the remaining AGE was substantially completely distilled away, whereby an epoxy modified silicone intermediate represented by the average composition formula $MD_{6.6}D^{R*31}{}_{0.6}D^{R*21}{}_{2.2}M$ was obtained as a light yellow, transparent liquid.

In the formula, $R^{*21}$ and $R^{*31}$ are as follows.

$R^{*21}$=—$C_3H_6OCH_2CH(O)CH_2$ $R^{*31}$=—$C_2H_4Si(OSiMe_3)_3$

Step 2: Inventive Synthesis (Secondary Amino Alcohol Added) and Removal of Low-Boiling Portion After the liquid inside the flask was cooled and the pressure was recovered, while stirring under a nitrogen stream, a solution containing 0.12 g of natural vitamin E, 23.0 g of diethanolamine (DEA), and 40 g of IPA was added to the reaction system, and aging at 65 to 85° C. was performed for about 3.5 hours. Furthermore, 7.4 g of N-methyl ethanolamine (MEA) was added and aging was continued for 5 hours. Next, the flask was heated to 130° C. under normal pressure to completely distill IPA, and the resultant distillate in a receptor was removed thereafter.

Step 3: Removal of High-Boiling Portion (Reinforced Stripping)

In the same manner as in Step 3 of Example 1, the ribbon heater was set to 130° C. and the oil bath was set to 170° C., and while stirring under a nitrogen stream, the pressure inside the flask was reduced to 9 mmHg. The temperature of the liquid inside the flask was maintained at 150 to 160° C. and the temperature at the head portion was maintained at 125 to 130° C. for about 3 hours, from the flask top to the end of the distillation head were completely dried, and no additional distillation occurred. The pressure was recovered, and 173.0 g of tertiary-amine structure-containing polyhydric alcohol modified silicone represented by the average composition formula $MD_{6.6}D^{R*31}{}_{0.6}\ D^{R*43}{}_{1.7}D^{R*42}{}_{0.5}M$ was obtained as a light yellow brown, substantially transparent viscous liquid.

In the formula, $R^{*43}$, $R^{*42}$, and $R^{*31}$ are as follows.

$R^{*43}$=—$C_3H_6O$—$CH_2CH(OH)CH_2$—$N(CH_2CH_2OH)_2$ $R^{*42}$=—$C_3H_6O$—$CH_2CH(OH)CH_2$—$N(CH_3)(CH_2CH_2OH)$ $R^{*31}$=—$C_2H_4Si(OSiMe_3)_3$

Step 4: Filtration

Since contamination due to silicone grease used for the ground glass joint of the separable flask was thought to cause some cloudiness in the appearance of the reaction product, filtration was performed using an activated-carbon-carrying depth filter. As a result, 145 g of a light brown, substantially transparent viscous liquid was obtained.

(Example 11) <Production of Silicone Compound No. 11>

Step 1: Synthesis (Hydro Silylation) of Intermediate and Purification (General Stripping)

First, 188.6 g of a methyl hydrogen polysiloxane represented by the average composition formula $MD_{390}D^H{}_{10.1}M$, 97 g of toluene, and 4.0 g of AGE were placed in a 500-ml separable flask, and were soaked in an oil bath and heated to 50° C. while stirring under a nitrogen stream. Then, 0.02 ml of a platinum-1,3-divinyl-1,1,3,3-tetramethyl disiloxane complex catalyst solution (Pt concentration: 4.4 wt %) was added, and a reaction was performed at 60 to 65° C. for 3.5 hours. Next, after 3.6 g of 1-hexene was added and a reaction was performed for 2 hours, a small amount of the reaction liquid was sampled, and it was confirmed by an alkali decomposition gas generation method that the target reaction rate had been achieved. The reaction liquid was maintained at 120 to 150° C. and under reduced pressure of 2 to 3 mmHg for about 70 minutes, the low-boiling portion containing the remaining AGE was completely distilled away, whereby an epoxy modified silicone intermediate represented by the average composition formula $MD_{390}D^{R*21}{}_{5.5}D^{R*11}{}_{4.5}M$ was obtained as a slightly yellow, transparent viscous liquid.

In the formula, $R^{*21}$ and $R^{*11}$ are as follows.

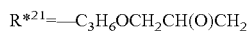

$R^{*21}=$—$C_3H_6OCH_2CH(O)CH_2$

$R^{*11}=$—$C_6H_{13}$

Step 2: Inventive Synthesis (Secondary Amino Alcohol Added) and Removal of Low-Boiling Portion After the liquid inside the flask was cooled and the pressure was recovered, while stirring under a nitrogen stream, a solution containing 0.11 g of natural vitamin E, 2.1 g of diisopropanolamine (DIPA), 0.7 g of ion exchanged water, 87 g of IPA was added to the reaction system, and aging at 65 to 85° C. was performed for 5.5 hours. Furthermore, 2.3 g of N-methyl ethanolamine (MEA) was added and aging was continued for 3.5 hours. Next, the flask was heated to 150° C. under normal pressure to completely distill IPA and water, and the resultant distillate in a receptor was removed thereafter.

Step 3: Removal of High-Boiling Portion (Reinforced Stripping)

In the same manner as in Step 3 of Example 1, the ribbon heater was set to 130° C. and the oil bath was set to 170° C., and while stirring under a nitrogen stream, the pressure inside the flask was reduced to 3 to 5 mmHg. The temperature of the liquid inside the flask was maintained at 155 to 170° C. and the temperature at the head portion was maintained at 125 to 130° C. for about 3 hours, from the flask top to the end of the distillation head were completely dried, and no additional distillation occurred. After cooling to 70° C. and then the pressure was recovered, 196.7 g of tertiary-amine structure-containing polyhydric alcohol modified silicone represented by the average composition formula $MD_{390}D^{R*41}{}_{2.5}D^{R*42}{}_{3.0}D^{R*11}{}_{4.5}M$ was obtained as a slightly yellow, completely transparent viscous liquid.

In the formula, $R^{*41}$, $R^{*42}$, $R^{*11}$ are as follows.

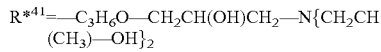

$R^{*41}=$—$C_3H_6O$—$CH_2CH(OH)CH_2$—$N\{CH_2CH(CH_3)$—$OH\}_2$

$R^{*42}=$—$C_3H_6O$—$CH_2CH(OH)CH_2$—$N(CH_3)(CH_2CH_2OH)$

$R^{*11}=$—$C_6H_{13}$

Step 4: Dilution in Oil Agent

Then, 37.5 g of the thus-obtained tertiary-amine structure-containing polyhydric alcohol modified silicone and 62.5 g of dimethyl polysiloxane (viscosity 2 cs) were measured and placed in a 200-ml glass bottle, which was in turn capped and underwent a process of shaking and heating in a 50° C. thermostatic bath 2 to 3 times, whereby a colorless, transparent solution was obtained.

(Example 12) <Production of Silicone Compound No. 12>

Step 1: Synthesis (Hydro Silylation) of Intermediate and Purification (General Stripping)

First, 187.6 g of a methyl hydrogen polysiloxane represented by the average composition formula $MD_{390}D^H{}_{10.1}M$, 97 g of toluene, and 8.7 g of AGE were placed in a 500-ml separable flask, and were soaked in an oil bath and heated to 60° C. while stirring under a nitrogen stream. Then, 0.02 ml of a platinum-1,3-divinyl-1,1,3,3-tetramethyl disiloxane complex catalyst solution (Pt concentration: 4.4 wt %) was added, and a reaction was performed at 65 to 85° C. for 2 hours. A small amount of the reaction liquid was sampled, and it was confirmed by an alkali decomposition gas generation method that the target reaction rate had been achieved. The reaction liquid was maintained at 150 to 155° C. and under reduced pressure of 2 mmHg for 1.5 hours, the low-boiling portion containing the remaining AGE was completely distilled away, whereby an epoxy modified silicone intermediate represented by the average composition formula $MD_{390}D^{R*21}{}_{10.1}M$ was obtained as a slightly yellow, transparent viscous liquid.

In the formula, $R^{*21}$ are as follows.

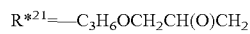

$R^{*21}=$—$C_3H_6OCH_2CH(O)CH_2$

Step 2: Inventive Synthesis (Secondary Amino Alcohol Added) and Removal of Low-Boiling Portion After the liquid inside the flask was cooled and the pressure was recovered, while stirring under a nitrogen stream, a solution containing 0.10 g of natural vitamin E, 12.9 g of diisopropanolamine (DIPA), 2.6 g of ion exchanged water, and 90 g of IPA was added to the reaction system, and aging at 75 to 85° C. was performed for 4.5 hours. Next, the flask was heated to 120° C. under normal pressure to completely distill IPA and water, and the resultant distillate in a receptor was removed thereafter.

Step 3: Removal of High-Boiling Portion (Reinforced Stripping)

In the same manner as in Step 3 of Example 1, the ribbon heater was set to 130° C. and the oil bath was set to 170° C., and while stirring under a nitrogen stream, the pressure inside the flask was reduced to 1 to 3 mmHg. The temperature of the liquid inside the flask was maintained at 150 to 170° C. and the temperature at the head portion was maintained at 125 to 130° C. for about 4 hours, from the flask top to the end of the distillation head were completely dried, and no additional distillation occurred. After cooling to 60° C. and then the pressure was recovered, 202.8 g of tertiary-amine structure-containing polyhydric alcohol modified silicone represented by the average composition formula $MD_{390}D^{R*41}{}_{10.1}M$ was obtained as a light yellow, completely transparent viscous liquid.

In the formula, $R^{*41}$ is as follows.

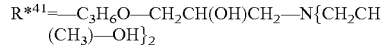

$R^{*41}=$—$C_3H_6O$—$CH_2CH(OH)CH_2$—$N\{CH_2CH(CH_3)$—$OH\}_2$

Step 4: Dilution in Oil Agent

Then, 37.5 g of the thus-obtained tertiary-amine structure-containing polyhydric alcohol modified silicone and 62.5 g of dimethyl polysiloxane (viscosity 2 cs) were measured and placed in a 200-ml glass bottle, which was in turn capped and underwent a process of shaking and heating in a 50° C. thermostatic bath 2 to 3 times, whereby a colorless, transparent solution was obtained.

(Example 13) <Production of Silicone Compound No. 13>

Step 1: Synthesis (Hydro Silylation) of Intermediate and Purification (General Stripping)

First, 187.6 g of a methyl hydrogen polysiloxane represented by the average composition formula $MD_{390}D^H{}_{10.1}M$, 97 g of toluene, and 6.1 g of AGE were placed in a 500-ml separable flask, and were soaked in an oil bath and heated to 50° C. while stirring under a nitrogen stream. Then, 0.03 ml of a platinum-1,3-divinyl-1,1,3,3-tetramethyl disiloxane complex catalyst solution (Pt concentration: 4.4 wt %) was added, and a reaction was performed at 50 to 80° C. for 7 hours. A small amount of the reaction liquid was sampled, and it was confirmed by an alkali decomposition gas generation method that the target reaction rate had been achieved. Next, after 2.0 g of 1-hexene was added and a reaction was performed for 2 hours, it was confirmed with the reaction rate examined by the same method that the reaction had been substantially completed. The reaction liquid was maintained at 140 to 150° C. and under reduced pressure of 2 to 3 mmHg for 2 hours, the low-boiling portion containing the remaining AGE was completely distilled away, whereby an epoxy modified silicone intermediate represented by the average composition formula $MD_{390}D^{R*21}{}_{7.0}D^{R*11}{}_{3.1}M$ was obtained as a slightly yellow, transparent viscous liquid.

In the formula, $R^{*21}$ and $R^{*11}$ are as follows.

$R^{*21}$=—$C_3H_6OCH_2CH(O)CH_2$ $R^{*11}$=—$C_6H_{13}$

Step 2: Inventive Synthesis (Secondary Amino Alcohol Added) and Removal of Low-Boiling Portion After the liquid inside the flask was cooled and the pressure was recovered, while stirring under a nitrogen stream, a solution containing 0.10 g of natural vitamin E, 8.9 g of diisopropanolamine (DIPA), 1.6 g of ion exchanged water, and 90 g of IPA was added to the reaction system, and aging at 75 to 85° C. was performed for 4 hours. Next, the flask was heated to 120° C. under normal pressure to completely distill IPA and water, and the resultant distillate in a receptor was removed thereafter.

Step 3: Removal of High-Boiling Portion (Reinforced Stripping)

In the same manner as in Step 3 of Example 1, the ribbon heater was set to 130° C. and the oil bath was set to 170° C., and while stirring under a nitrogen stream, the pressure inside the flask was reduced to 7 to 9 mmHg. The temperature of the liquid inside the flask was maintained at 150 to 170° C. and the temperature at the head portion was maintained at 125-130° C. for 4 hours, from the flask top to the end of the distillation head were completely dried, and no additional distillation occurred. After cooling to 80° C. and then the pressure was recovered, 196.9 g of tertiary-amine structure-containing polyhydric alcohol modified silicone represented by the average composition formula $MD_{390}D^{R*41}{}_{7.0}D^{R*11}{}_{3.1}M$ was obtained as a light brown, completely transparent viscous liquid.

In the formula, $R^{*41}$, $R^{*11}$ are as follows.

$R^{*41}$=—$C_3H_6O$—$CH_2CH(OH)CH_2$—$N\{CH_2CH(CH_3)$—$OH\}_2$ $R^{*11}$=—$C_6H_{13}$

Step 4: Dilution in Oil Agent

Then, 37.5 g of the thus-obtained tertiary-amine structure-containing polyhydric alcohol modified silicone and 62.5 g of dimethyl polysiloxane (viscosity 2 cs) were measured and placed in a 200-ml glass bottle, which was in turn capped and underwent a process of shaking and heating in a 50° C. thermostatic bath 2 to 3 times, whereby a colorless, transparent solution was obtained.

(Comparative Example 1) <Production of Silicone Compound RE-1>

Step 1: Synthesis (Hydro Silylation) of Intermediate and Purification (General Stripping)

First, 69.9 g of AGE and 0.02 ml of a platinum-1,3-divinyl-1,1,3,3-tetramethyl disiloxane complex catalyst solution (Pt concentration: 4.4 wt %) were placed in a 500-ml separable flask, and were soaked in an oil bath and heated to 50° C. while stirring under a nitrogen stream. Then, about 3 g each of a 1,1,3,3-tetramethyl disiloxane represented by the chemical structural formula $^HMM^H$ was put in the flask 12 times (34.5 g in total) (it took a total of 45 minutes to put the disiloxane in the flask), and the liquid temperature was controlled at or below 65° C. such that the reaction generally proceeded while avoiding bumping due to reaction heat. In this process, 0.055 ml of the catalyst solution was added when heat generation became slower. After the disiloxane was put in the flask, aging at 65 to 70° C. was performed for 2 hours, a small amount of the reaction liquid was sampled, and it was confirmed by an alkali decomposition gas generation method that the target reaction rate had been achieved. The reaction liquid was maintained at 110 to 140° C. and under reduced pressure of 3 to 4 mmHg for 45 minutes, the low-boiling portion containing the remaining AGE was completely distilled away, whereby an epoxy modified silicone intermediate represented by the chemical structural formula $^{R*21}MM^{R*21}$ was obtained as a light yellow, transparent liquid.

In the formula, $R^{*21}$ are as follows.

$R^{*21}$=—$C_3H_6OCH_2CH(O)CH_2$

Step 2: Comparative Synthesis (Secondary Amino Alcohol Added) and Purification (General Stripping)

After the liquid inside the flask was cooled and the pressure was recovered, while stirring under a nitrogen stream, 102.6 g of diisopropanolamine (DIPA), 18.3 g of ion exchanged water, and 21 g of IPA were sequentially put in the reaction system at room temperature. The oil bath was heated with its temperature set to 80 to 90° C., and as a result, the temperature of the reaction liquid rose to 94° C., partly influenced by heat generation in the reaction. Subsequently, aging at 80 to 90° C. was performed for 4 hours, and then the flask was heated to 130° C. under normal pressure to substantially distill IPA and water, and the resultant distillate in a receptor was removed thereafter. The pressure of the liquid inside the flask was reduced to 1 to 7 mmHg at 110 to 130° C., and this state was maintained for 1.5 hours. In this process, while no liquid was distilled over the distillation head (distillation had stopped), a large number of droplets, which was presumably of the remaining DIPA, adhered on the upper part of the inner walls and the cap of the flask. After the pressure was recovered, 181.0 g of a coarse composition containing modified silicone having tertiary-amine structure-containing polyhydric alcohol group, on both terminals, represented by the chemical structural formula $^{R*41}MM^{R*41}$ was obtained as a brown, semi-transparent viscous liquid.

In the formula, $R^{*41}$ is as follows.

$R^{*41}$=—$C_3H_6O$—$CH_2CH(OH)CH_2$—$N\{CH_2CH(CH_3)$—$OH\}_2$ (Comparative Example 2) <Production of Silicone Compound RE-2>

Step 1: Synthesis (Hydro Silylation) of Intermediate and Purification (General Stripping)

First, 88.0 g of a heptamethyl trisiloxane represented by the chemical structural formula $MDH1M$ and 10.5 g of AGE were placed in a 500-ml separable flask, and were soaked in an oil bath and heated to 47° C. while stirring under a nitrogen stream. Then, 0.016 ml of a platinum-1,3-divinyl-1,1,3,3-tetramethyl disiloxane complex catalyst solution (Pt concentration: 4.4 wt %) was added, and the internal liquid temperature rose to 61° C. due to reaction heat. While the liquid temperature was controlled at or below 70° C. so as to avoid bumping due to reaction heat, the remaining 46.1 g in total of AGE was gradually put in 6 times. In this process, 0.032 ml of the catalyst solution was added when heat generation became slower. In this manner, after aging at 70 to 90° C. was performed for a total of 8 hours, a small amount of the reaction liquid was sampled, and it was confirmed by an alkali decomposition gas generation method that the target reaction rate had been achieved. The reaction liquid was maintained at 75 to 135° C. and under reduced pressure of 2 to 6 mmHg for 1.7 hours, the low-boiling portion containing the remaining AGE was completely distilled away, whereby an epoxy modified silicone intermediate represented by the chemical structural formula $MD^{R*21}1M$ was obtained as a slightly yellow, transparent liquid.

In the formula, $R^{*21}$ are as follows.

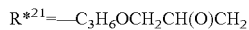

$R^{*21}$=—$C_3H_6OCH_2CH(O)CH_2$

Step 2: Comparative Synthesis (Secondary Amino Alcohol Added) and Purification (General Stripping)

After the liquid inside the flask was cooled to 90° C. and the pressure was recovered, while stirring under a nitrogen stream, 62.5 g of diethanolamine (DEA) and 11.8 g of IPA were sequentially put in the reaction system. Heat generation was observed as IPA was put in, and the temperature of the liquid inside the flask rose from 85° C. (before IPA was put in) to 131° C. in 2 minutes, although it was being cooled. Fortunately, no bumping phenomenon was observed. When the internal liquid temperature was dropped to 110° C., an oil bath was provided to perform aging at 75 to 110° C. for 5 hours. Next, the flask was heated to 130° C. under normal pressure to substantially distill IPA, and the resultant distillate in a receptor was removed thereafter. The pressure of the liquid inside the flask was reduced to 1 to 6 mmHg at 110 to 130° C., and this state was maintained for 70 minutes. In this process, while no liquid was distilled over the distillation head (distillation had stopped), a large number of droplets, which was presumably of the remaining DEA, adhered on the upper part of the inner walls and the cap of the flask. After the pressure was recovered, 180.8 g of a coarse composition containing a modified trisiloxane having tertiary-amine structure-containing polyhydric alcohol group represented by the chemical structural formula $MD^{R*43}_1M$ was obtained as a light yellow brown, substantially transparent liquid.

In the formula, $R^{*43}$ is as follows.

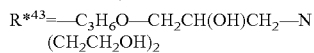

$R^{*43}$=—$C_3H_6O$—$CH_2CH(OH)CH_2$—N
  $(CH_2CH_2OH)_2$ (Comparative Example 3) <Production of Silicone Compound RE-3>

Step 1: Synthesis (Hydro Silylation) of Intermediate and Purification (General Stripping)

First, 138.6 g of a methyl hydrogen polysiloxane represented by the average composition formula $^HMD_{15.5}M^H$ and 13.8 g of AGE were placed in a 500-ml separable flask, and were soaked in an oil bath and heated to 56° C. while stirring under a nitrogen stream. Then, 0.02 ml of a platinum-1,3-divinyl-1,1,3,3-tetramethyl disiloxane complex catalyst solution (Pt concentration: 4.4 wt %) was added, and the internal liquid temperature rose to 84° C. due to reaction heat. While the liquid temperature was controlled at or below 90° C. so as to avoid bumping due to reaction heat, the remaining 17.5 g in total of AGE was gradually put in 3 times. In this process, 0.02 ml of the catalyst solution was added when heat generation became slower. In this manner, after aging at 75 to 90° C. was performed for a total of 6 hours, a small amount of the reaction liquid was sampled, and it was confirmed by an alkali decomposition gas generation method that the target reaction rate had been achieved. The reaction liquid was maintained at 80 to 160° C. and under reduced pressure of 2 to 5 mmHg for 80 minutes, the low-boiling portion containing the remaining AGE was substantially completely distilled away, whereby an epoxy modified silicone intermediate represented by the average composition formula $^{R*21}MD_{15.5}M^{R*21}$ was obtained as a slightly brown, transparent liquid.

In the formula, $R^{*21}$ are as follows.

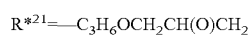

$R^{*21}$=—$C_3H_6OCH_2CH(O)CH_2$

Step 2: Comparative Synthesis (Secondary Amino Alcohol Added) and Purification (General Stripping)

After the liquid inside the flask was cooled to 90° C. and the pressure was recovered, 34.6 g of diethanolamine (DEA) was added while stirring under a nitrogen stream. After 31.5 g of IPA was further added to the 70° C. internal liquid, heating in the oil bath was resumed. Then, aging at 85 to 100° C. was performed for 4.5 hours, the flask was then heated to 130° C. under normal pressure to substantially distill IPA, and the resultant distillate in a receptor was removed thereafter. The pressure of the liquid inside the flask was reduced to 8 to 21 mmHg at 110 to 130° C., and this state was maintained for 50 minutes. In this process, while no liquid was distilled over the distillation head (distillation had stopped), a large number of droplets, which was presumably of the remaining DEA, adhered on the upper part of the inner walls and the cap of the flask. After the pressure was recovered, 184.4 g of a coarse composition containing modified silicone having tertiary-amine structure-containing polyhydric alcohol group, on both terminals, represented by the average composition formula $^{R*43}MD_{15.5}M^{R*43}$ was obtained as a light yellow brown, substantially transparent liquid.

In the formula, $R^{*43}$ is as follows.

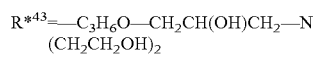

$R^{*43}$=—$C_3H_6O$—$CH_2CH(OH)CH_2$—N
  $(CH_2CH_2OH)_2$ (Comparative Example 4) <Production of Silicone Compound RE-4>

Step 1: Synthesis (Hydro Silylation) of Intermediate and Purification (General Stripping)

First, 951.4 g of a methyl hydrogen polysiloxane represented by the average composition formula $^HMD_{187}M^H$ and 19.8 g of AGE were placed in a 1 L-separable flask and heated to 65° C. while stirring under a nitrogen stream. Then, 0.07 ml of an IPA solution (Pt concentration: 4.5 wt %) of a platinum-1,3-divinyl-1,1,3,3-tetramethyl disiloxane complex was added, and a reaction was performed at 65 to 85° C. for 3 hours. Then, 2 g of the reaction liquid was sampled, and it was confirmed by an alkali decomposition gas generation method that the reaction had been completed. The reaction liquid was further heated to 160° C. under reduced pressure, the low-boiling portion containing the remaining AGE was substantially completely distilled away, whereby an epoxy modified silicone intermediate represented by the average composition formula $R^{*21}MD_{187}M^{R*2}_1$ was obtained as a light yellow, transparent liquid.

Step 2: Comparative Synthesis (Secondary Amino Alcohol Added) and Purification (General Stripping)

Next, after the content in the flask was cooled to 100° C. or below, 33.9 g of an 85-wt % diisopropanolamine (DIPA) aqueous solution was added, and the resultant mixture was dehydrated at 100 to 110° C. and under reduced pressure of 10 mmHg or less, and a reaction was performed for 4.5 hours. As a result, 991 g of a coarse composition containing modified silicone having tertiary-amine structure-containing polyhydric alcohol group, on both terminals, represented by the average composition formula $R^{*41}MD_{187}M^{R*41}$ was obtained as a slightly yellow, substantially transparent liquid.

In the formula, $R^{*41}$ is as follows.

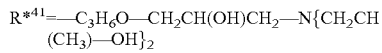
$R^{*41}$=—$C_3H_6O$—$CH_2CH(OH)CH_2$—$N\{CH_2CH(CH_3)$—$OH\}_2$ (Comparative Example 5) <Production of Polyether Modified Silicone RE-5>

Step 1: Hydrosilylation Reaction and General Stripping

First, 1531.5 g of a methyl hydrogen polysiloxane represented by the average composition formula $MD_{45}D^H_2M$, 569 g of allylpolyether represented by the average composition formula $CH_2$=$CHCH_2O(C_2H_4O)_{10}H$, 1.05 g of natural vitamin E, and 210 g of IPA were placed in a 3 L-separable flask, and heated to 40 to 50° C. while stirring under a nitrogen stream. Then, 2.1 g of an IPA solution (Pt concentration: 0.45 wt %) of a platinum-1,3-divinyl-1,1,3,3-tetramethyl disiloxane complex was added, and a reaction was performed at 75 to 85° C. for 2 hours. A small amount of the reaction liquid was sampled, and it was confirmed by an alkali decomposition gas generation method that the reaction had been completed. Furthermore, the pressure of the reaction liquid was reduced to 40 mmHg at 70 to 80° C. to substantially distill away, this state was maintained for 1 hour for drying, whereby a coarse composition containing polyether modified silicone represented by the average composition formula $MD_{45}D^{R*51}_2M$.

In the formula, $R^{*51}$ is as follows.

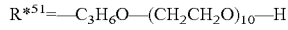
$R^{*51}$=—$C_3H_6O$—$(CH_2CH_2O)_{10}$—H

Step 2: Acid Treatment for Lower Odor (3 Times in Total) and General Stripping

After the pressure inside of the flask was recovered, 31.6 g of a 0.33 mass % sodium hydrogensulfate aqueous solution was added while stirring under a nitrogen stream, and the resultant mixture was heated at 70 to 80° C. for 1 hour while stirring, whereby hydrolysis of the remaining polyether was performed. Thereafter, the pressure was reduced to 40 mmHg slowly in about 1.5 hours so as not to cause foaming and bumping, whereby the low-boiling portion including water and odor components was distilled. The pressure was recovered once it reached the target pressure, 31.5 g of ion exchanged water was added to the flask, the resulting mixture was heated and stirred for 30 minutes, and the pressure was reduced again to 40 mmHg slowly in about 1.5 hours so as not to cause foaming and bumping, and the low-boiling portion including water and odor components was distilled. This process was repeated one more time, and in the last stage, when the system reached a state at 70 to 80° C. and under 30 to 40 mmHg, this state was maintained for 3 hours to dry and eliminate all the droplets in the system. After the resultant product was cooled to or below 50° C. and the pressure was recovered, the liquid inside the flask was a brown, semitransparent liquid.

Step 3: Filtration

To reduce cloudiness in the appearance, pressure filtration was performed using a zeta potential absorption filter. As a result, about 2030 g of a light brown, substantially transparent liquid was obtained.

(Comparative Example 6) <Production of Polyether Modified Silicone RE-6>

Step 1: Hydrosilylation Reaction and General Stripping

First, 1053.4 g of a methyl hydrogen polysiloxane represented by the average composition formula $MD_{37}D^H_{13}M$, 95.6 g of vinyl[tris(trimethylsiloxy)]silane represented by the average composition formula $CH_2$=$CH$—$Si(OSiMe_3)_3$, and 2.2 g of an IPA solution (Pt concentration: 0.45 wt %) of a platinum-1,3-divinyl-1,1,3,3-tetramethyl disiloxane complex were placed in a 3 L-separable flask, and heated while stirring under a nitrogen stream. After aging at 70 to 80° C. was performed for 2.5 hours, a small amount of the reaction liquid was sampled, and it was confirmed by an alkali decomposition gas generation method that the target reaction rate had been achieved. After the liquid inside the flask was cooled to 50° C., about 89 g each of 1-dodecen was put in the flask 3 times (267 g in total), such that the reaction gradually proceeded while the increasing liquid temperature due to reaction heat was controlled not to exceed 75° C. After aging was performed for 1 hour, it was confirmed with the sampled reaction liquid that the target reaction rate had been achieved. Then, 318 g of allylpolyether represented by the average composition formula $CH_2$=$CHCH_2O(C_2H_4O)_{10}H$, 0.20 g of natural vitamin E, and 2.2 g of the catalyst solution were added, aging at 60 to 70° C. was performed for 1.5 hours, and it was confirmed with the same method that the target reaction rate had been achieved. Finally, again, about 89 g each of 1-dodecen was put in the flask 3 times (267 g in total), such that the reaction gradually proceeded while the increasing liquid temperature due to reaction heat was controlled not to exceed 75° C. After aging was performed for 3 hours, it was confirmed that the reaction had been completed. The reaction liquid was further heated under reduced pressure to be maintained at 135 to 145° C. and under 5 to 10 mmHg for 5 hours, and the low-boiling portion including dodecen was distilled away. Subsequently, after cooling to 75° C. or lower and then the pressure was recovered, a composition containing polyether modified silicone represented by the average composition formula $MD_{37}D^{R*31}_1D^{R*51}_2D^{R**12}_{10}M$ was obtained as a light brown, transparent liquid.

In the formula, $R^{*51}$, $R^{*12}$, and $R^{*31}$ are as follows.

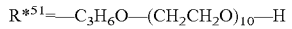
$R^{*51}$=—$C_3H_6O$—$(CH_2CH_2O)_{10}$—H

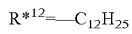
$R^{*12}$=—$C_{12}H_{25}$

$R^{*31}$=—$C_2H_4Si(OSiMe_3)_3$

Step 2: Acid Treatment for Lower Odor (3 Times in Total) and General Stripping

To the content of the flask, an aqueous solution in which 0.30 g of sodium hydrogensulfate monohydrate was dissolved in 30 g of ion exchanged water was added, and the resultant mixture was heated at 60 to 70° C. for 1 hour while stirring, whereby hydrolysis of the remaining polyether was performed. Thereafter, the pressure was reduced to 30 mmHg slowly in about 1.5 hours so as not to cause foaming and bumping, whereby the low-boiling portion including water and odor components was distilled. The pressure was recovered once it reached the target pressure, 30 g of ion exchanged water was added to the flask, the resulting mixture was heated and stirred for 30 minutes, and the pressure was reduced again to 40 mmHg slowly in about 1.5 hours so as not to cause foaming and bumping, and the low-boiling portion including water and odor components was distilled. This process was repeated one more time, and in the last stage, when the system reached a state at 60 to 70° C. and under 30 to 40 mmHg, this state was maintained for 3 hours to dry and eliminate all the droplets in the system. After the resultant product was cooled to or below 50° C. and the pressure was recovered, the liquid inside the flask was a brown, semitransparent liquid.

Step 3: Filtration

To reduce cloudiness in the appearance, pressure filtration was performed using a zeta potential absorption filter. As a result, about 1820 g of a light brown, substantially transparent liquid was obtained.

(Comparative Example 7) <Production of Polyether Modified Silicone RE-7>

Step 1: Hydrosilylation Reaction

First, 290 g of a methyl hydrogen polysiloxane represented by the average composition formula $MD_{6.6}D^{H}{}_{2.8}M$ and 710 g of allylpolyether represented by the average composition formula $CH_2=CHCH_2O(C_2H_4O)_{12}H$ were placed in a 1 L-separable flask, and heated to 75° C. while stirring under a nitrogen stream. Then, 9.1 g of a catalyst solution in which an IPA solution (Pt concentration: 4.1 wt %) of a platinum-1,3-divinyl-1,1,3,3-tetramethyl disiloxane complex was diluted 50 times in the allylpolyether was added, and aging was performed for 2 hours such that the reaction liquid did not exceed 115° C. while the flask was further heated. A small amount of the reaction liquid was sampled, and it was confirmed that the reaction had been substantially completed. As a result, a coarse composition containing polyether modified silicone represented by the average composition formula $MD_{6.6}DR*^{52}{}_{2.8}M$ was obtained as a light brown, transparent liquid.

In the formula, $R*^{52}$ is as follows.

$$R*^{52}=-C_3H_6O-(CH_2CH_2O)_{12}-H$$

(Comparative Example 8) <Production of Polyether Modified Silicone RE-8>

Step 1: Hydrosilylation Reaction

First, 251.0 g of a methyl hydrogen polysiloxane represented by the average composition formula $MD_{396}D^{H}{}_{4}M$, 91.8 g of allylpolyether represented by the average composition formula $CH_2=CHCH_2O(C_2H_4O)_{18}(C_3H_6O)_{18}H$, 0.16 g of sodium acetate, and 85.7 g of IPA were placed in a 1 L-separable flask, and heated to 70° C. while stirring under a nitrogen stream. Then, 0.015 ml of a platinum-1,3-divinyl-1,1,3,3-tetramethyl disiloxane complex solution (Pt concentration: 22 wt %) was added, which triggered a reaction, whereby the internal liquid temperature rose to 85° C. due to heat generation and reflux of the IPA was observed. Thereafter, aging at 80 to 85° C. was performed for 2 hours, a small amount of the reaction liquid was sampled, and it was confirmed that the reaction had been substantially completed.

Step 2: Dilution in Oil Agent and Removal of Solvent (General Stripping)

Next, while stirring, 380 g of dimethyl polysiloxane (viscosity 2 cs) was added to the flask, and the resultant mixture was heated to 100° C. and then the pressure was gradually reduced to 50 mmHg, whereby IPA was distilled. The pressure was recovered once distillation of IPA stopped, and 191.3 g of dimethyl polysiloxane (viscosity 2 cs) was additionally blended. As a result, a coarse composition containing polyether modified silicone represented by the average composition formula $MD_{396}D^{R*53}{}_{4}M$ and dimethyl polysiloxane (viscosity 2 cs) serving as a diluted oil agent was obtained as a milky white viscous liquid.

In the formula, $R*^{53}$ is as follows.

$$R*^{53}=-C_3H_6O-(C_2H_4O)_{18}(C_3H_6O)_{18}-H$$

The average composition formulae of the "silicone compound No. 1" to the "silicone compound No. 13" according to the present invention synthesized as described above, and the average composition formulae of the "silicone compound RE1" to the "silicone compound RE4" and the "polyether modified silicone RE-5" to the "polyether modified silicone RE-8" in Comparative Examples are as follows.

TABLE 1

| Design structures, contents, and the like of samples obtained in the Examples | | |
|---|---|---|
| Silicone compound | Average composition formula | Property |
| Silicone compound No. 1 | $MD_{43.7}D^{R*41}{}_{2.1}D^{R*11}{}_{5.3}M$ | Completely transparent light tan liquid |
| Silicone compound No. 2 | $MD_{43.7}D^{R*41}{}_{1.0}D^{R*42}{}_{1.1}D^{R*11}{}_{5.3}M$ | Completely transparent pale yellow liquid |
| Silicone compound No. 3 | $MD_{37}D^{R*31}{}_{1.0}D^{R*41}{}_{2.1}D^{R*12}{}_{2.1}D^{R*12}{}_{9.6}M$ | Completely transparent light tan liquid |
| Silicone compound No. 4 | $MD_{37}D^{R*31}{}_{1.0}D^{R*41}{}_{1.6}D^{R*42}{}_{0.5}D^{R*12}{}_{9.6}M$ | Completely transparent light tan liquid |
| Silicone compound No. 5 | $MD_{44.5}D^{R*41}{}_{2.1}M$ | Completely transparent colorless liquid |
| Silicone compound No. 6 | $MD_{44.5}D^{R*41}{}_{1.0}D^{R*42}{}_{1.1}M$ | Completely transparent light tan liquid |

TABLE 1-continued

Design structures, contents, and the like of samples obtained in the Examples

| Silicone compound | Average composition formula | Property |
|---|---|---|
| Silicone compound No. 7 | $MD_{44.5}D^{R*31}{}_{1.0}D^{R*42}{}_{1.1}M$ | Completely transparent light tan liquid |
| Silicone compound No. 8 | $MD_{6.6}D^{R*43}{}_{2.8}M$ | Completely transparent colorless viscous liquid |
| Silicone compound No. 9 | $MD_{6.6}D^{R*31}{}_{0.6}R^{*43}{}_{2.2}M$ | Nearly transparent colorless viscous liquid |
| Silicone compound No. 10 | $MD_{6.6}D^{R*31}{}_{0.6}D^{R*43}{}_{1.7}MD^{R*42}{}_{0.5}M$ | Nearly transparent light tan viscous liquid |
| Silicone compound No. 11 | $MD_{390}D^{R*41}{}_{2.5}D^{R*42}{}_{3.0}D^{R*11}{}_{4.5}M$ | Completely transparent pale yellow viscous liquid |
| Silicone compound Mixture containing No. 11 | Same as above *Diluted to a concentration of 37.5% with dimethylpolysiloxane | Completely transparent colorless liquid |
| Silicone compound No. 12 | $MD_{390}D^{R*41}{}_{10.1}M$ | Completely transparent light yellow viscous liquid |
| Silicone compound Mixture containing No. 12 | Same as above *Diluted to a concentration of 37.5% with dimethylpolysiloxane | Completely transparent colorless liquid |
| Silicone compound No. 13 | $MD_{390}D^{R*41}{}_{7.0}D^{R*11}{}_{3.1}M$ | Completely transparent light tan viscous liquid |
| Silicone compound Mixture containing No. 13 | Same as above *Diluted to a concentration of 37.5% with dimethylpolysiloxane | Completely transparent colorless liquid |

TABLE 2

Design structures, contents, and the like of samples obtained in the Examples

| For comparison Silicone compound RE-1 | $R^{*41}MM^{R*41}$ | Semitransparent tan viscous liquid |
|---|---|---|
| For comparison Silicone compound RE-2 | $MD^{R*43}{}_{1}M$ | Nearly transparent light brownish yellow liquid |
| For comparison Silicone compound RE-3 | $R^{*43}MD_{15.5}M^{R*43}$ | Nearly transparent light brownish yellow liquid |
| For comparison Silicone compound RE-4 | $R^{*41}MD_{187}M^{R*41}$ | Nearly transparent pale yellow liquid |
| Polyether-modified silicone RE-5 for comparison | $MD_{45}D^{R*51}{}_{2}M$ | Nearly transparent light tan liquid |
| Polyether-modified silicone RE-6 for comparison | $MD_{37}D^{R*31}{}_{1}D^{R*51}{}_{2}D^{R*12}{}_{10}M$ | Nearly transparent light tan liquid |
| Polyether-modified silicone RE-7 for comparison | $MD_{6.6}D^{R*52}{}_{2.8}M$ | Transparent light tan liquid |
| Mixture containing polyether-modified silicone RE-8 for comparison | $MD_{396}D^{R*53}{}_{4}M$ *Diluted to a concentration of 37.5% with dimethylpolysiloxane | Milky white viscous liquid (In the form of gum when not diluted) |

In this table, the structures and categories of the functional groups are as follows.

<Mid- to Long-Chain Alkyl Group: $R^{*1}$>

$R^{*11}$=—$C_6H_{13}$ $R^{*12}$=—$C_{12}H_{25}$

<Alkyl Group Substituted with Glycidyloxy Group: $R^{*2}$>

$R^{*21}$=—$C_3H_6OCH_2CH(O)CH_2$

<Siloxane Dendron Structure-Containing Group: $R^{*3}$>

$R^{*31}$=—$C_2H_4Si(OSiMe_3)$

<Tertiary Amine Structure-Containing Polyhydric Alcohol Modified Group: $R^{*4}$>

$R^{*41}$=—$C_3H_6O$—$CH_2CH(OH)CH_2$—$N\{CH_2CH(CH_3)$—$OH\}_2$ $R^{*42}$=—$C_3H_6O$—$CH_2CH(OH)CH_2$—$N(CH_3)(CH_2CH_2OH)$ $R^{*43}$=—$C_3H_6O$—$CH_2CH(OH)CH_2$—$N(CH_2CH_2OH)_2$

<Polyoxyethylene Structure-Containing Polyether Group: $R^{*5}$>

$R^{*51}$=—$C_3H_6O$—$(CH_2CH_2O)_{10}$—H $R^{*52}$=—$C_3H_6O$—$(CH_2CH_2O)_{12}$—H $R^{*53}$=—$C_3H_6O$—$(C_2H_4O)_{18}(C_3H_6O)_{18}$—H

These groups that have similar structures of their hydrophobic portions, such as the length of polysiloxane main chains, were categorized into the same group, and the viscosity (25° C.) of the silicone compounds in Examples and that of polyether modified silicone in Comparative Examples were compared. The results, as well as data on the number of repetitions (polymerization degree) of siloxane units except for those on terminals and data on the number of hydrophilic modified groups (average value) bonded to the main chain, were listed in Table 3 to Table 6 below.

Group 1: Has a middle polymerization degree, and has good affinity with silicone oil.

Group 2: Has a middle polymerization degree, and has good affinity with silicone oil to organic oil.

Group 3: Has a small polymerization degree, and has good affinity with polar solvents.

Group 4: Has a large polymerization degree, and has good affinity with silicone oil.

TABLE 3

Comparison of viscosity (Group 1)

| Silicone compound | Polymerization degree | Number of hydrophilic modified groups | Viscosity [mPas] |
|---|---|---|---|
| Polyether-modified silicone RE-5 for comparison | 47 | 2 | 950 |
| Silicone compound No. 1 | 51.1 | 2.1 | 698 |
| Silicone compound No. 2 | 51.1 | 2.1 | 403 |
| Silicone compound No. 5 | 46.6 | 2.1 | 685 |
| Silicone compound No. 6 | 46.6 | 2.1 | 340 |

TABLE 4

Comparison of viscosity (Group 2)

| Silicone compound | Polymerization degree | Number of hydrophilic modified groups | Viscosity [mPas] |
|---|---|---|---|
| Polyether-modified silicone RE-6 for comparison | 50 | 2 | 1800 |
| Silicone compound No. 3 | 49.7 | 2.1 | 1590 |
| Silicone compound No. 4 | 49.7 | 2.1 | 993 |

TABLE 5

Comparison of viscosity (Group 3)

| Silicone compound | Polymerization degree | Number of hydrophilic modified groups | Viscosity [mPas] |
|---|---|---|---|
| Polyether-modified silicone RE-7 for comparison | 9.4 | 2.8 | 310 |
| Silicone compound No. 8 | 9.4 | 2.8 | 10200 |
| Silicone compound No. 9 | 9.4 | 2.2 | 7400 |
| Silicone compound No. 10 | 9.4 | 2.2 | 4880 |

TABLE 6

Comparison of viscosity (Group 4)

| Silicone compound | Polymerization degree | Number of hydrophilic modified groups | Viscosity [mPas] |
|---|---|---|---|
| Polyether-modified silicone RE-8 for comparison | 400 | 4 | Unmeasurable (in the form of gum) |
| Silicone compound No. 11 | 400.1 | 5.5 | 13400 |
| Silicone compound No. 12 | 400.1 | 10.1 | 68000 |
| Silicone compound No. 13 | 400.1 | 7.0 | 75500 |
| Mixture containing polyether-modified silicone RE-8 for comparison | 400 | 4 | 5000 |
| Mixture containing silicone compound No. 11 | 400.1 | 5.5 | 143 |
| Mixture containing silicone compound No. 12 | 400.1 | 10.1 | 493 |
| Mixture containing silicone compound No. 13 | 400.1 | 7.0 | 525 |

As can be seen in the results described above, the tertiary-amine structure-containing polyhydric alcohol modified silicone according to the present invention exhibited lower viscosity than polyether modified silicone with the corresponding structure in all cases except for the group 3 with a structural design for achieving a higher affinity with polar solvent, and thus is found to be advantageous in terms of handling and production efficiency in these cases. We believe that this is an astonishing founding. Conventionally, it has been a common sense of the industry that the polyhydric alcohol modified silicone involves a larger increase in viscosity than the corresponding polyether modified silicone due to a large number of hydroxyl groups in the hydrophilic portion, and that there is nothing that can be done for that. The behavior of the viscosity in the groups 1, 2 and 4 has overturned the conventional belief regarding the polyhydric alcohol modified silicone.

Material Compatibility

Next, compatibility with various hydrophobic oil agents or polar solvents described below is test for each group at three levels of temperature (room temperature, 50° C., and 3° C.). The weight ratio between modified silicone and oil agent (solvent) was set to be 1:9.

Examples of Hydrophobic Oil Agent (Abbreviated with Chemical Name or INCI)

20 cs: dimethylpolysiloxane 20 cst
10 cs: dimethylpolysiloxane 10 cst
6 cs: dimethylpolysiloxane 6 cst
2 cs: dimethylpolysiloxane 2 cst
D5: decamethylcyclopentasiloxane
556: phenyltrimethicone
3196: aprylyl methicone
ID: isododecane
IP: light liquid isoparaffin
IOTG: tri (2-ethylhexanoic acid) glyceryl
CEH: Cetyl 2-ethylhexanoate
LP: liquid paraffin (mineral oil)
JB: jojoba oil
SF: sunflower oil Examples of Polar Solvent (Abbreviated with Chemical Name or INCI)

IPA: isopropyl alcohol
EtOH: ethanol
DPG: Dipropylene glycol
BG: 1,3-Butylene glycol
PG: Propylene glycol
GL: glycerin
SO: 70% sorbitol aqueous solution
H2O: ion exchanged water The results of the compatibility test for each group is described below (Table 7 to Table 11). (Table 7 to Table 11) The test is also conducted for appropriately selected ones of Comparative silicone compounds RE-1 to RE-4 not included in the four groups described above. The outer appearance of the mixture was ranked based on the following five reference levels.

Evaluation point 5: crystal clear colorless transparent solution
Evaluation point 4: substantially transparent to slightly translucent uniform liquid (colorless to slightly bluish outer appearance)
Evaluation point 3: translucent uniform liquid, slightly whitish outer appearance
Evaluation point 2: dispersion with haze involving diffused reflection of light
Evaluation point 1: completely opaque liquid (extremely hazy to white turbidity) or phase separation

TABLE 7

Compatibility with hydrophobic oil agent (group 1)

|  | 10 cs | 6 cs | 2 cs | D5 | 556 | 3196 | ID | IP | 3196/CEH | 3196/LP | IOTG | CEH |
|---|---|---|---|---|---|---|---|---|---|---|---|---|
| RT |  |  |  |  |  |  |  |  |  |  |  |  |
| No. 1 | 5 | 5 | 5 | 5 | 5 | 5 | 5 | 5 | 5 | 5 | 5 | 2 |
| No. 2 | 5 | 5 | 5 | 5 | 5 | 5 | 5 | 5 | 5 | 5 | 5 | 3 |
| No. 5 | 2 | 5 | 5 | 5 | 5 | 5 | 5 | 4 | 5 | 1 | 4 | 1 |
| RE-5 | 1 | 3 | 3 | 3 | 4 | 3 | 3 | 3 | 1 | 1 | 3 | 1 |
| RE-2 | 1 | 1 | 5 | 5 | 3 | 5 | 1 | 2 | 1 | 2 | 1 | 1 |
| RE-3 | 1 | 1 | 1 | 1 | 1 | 1 | 2 | 2 | 1 | 1 | 2 | 1 |
| 50 C. |  |  |  |  |  |  |  |  |  |  |  |  |
| No. 1 | 5 | 5 | 5 | 5 | 5 | 5 | 5 | 5 | 5 | 5 | 5 | 2 |
| No. 2 | 5 | 5 | 5 | 5 | 5 | 5 | 5 | 5 | 5 | 5 | 5 | 5 |
| No. 5 | 1 | 5 | 5 | 5 | 5 | 5 | 4 | 5 | 1 | 5 | 1 |
| RE-5 | 1 | 3 | 1 | 1 | 4 | 3 | 3 | 4 | 4 | 1 | 3 | 1 |
| RE-2 | 1 | 1 | 5 | 5 | 3 | 5 | 2 | 2 | 3 | 1 | 1 | 1 |
| RE-3 | 1 | 1 | 1 | 1 | 1 | 1 | 1 | 1 | 1 | 1 | 1 | 1 |
| 3 C. |  |  |  |  |  |  |  |  |  |  |  |  |
| No. 1 | 5 | 5 | 5 | 5 | 5 | 5 | 5 | 5 | 5 | 3 | 1 |
| No. 2 | 5 | 5 | 5 | 5 | 5 | 5 | 5 | 5 | 5 | 5 | 3 |
| No. 5 | 1 | 5 | 5 | 5 | 5 | 5 | 5 | 5 | 1 | 1 | 1 |
| RE-5 | 1 | 1 | 1 | 1 | 1 | 1 | 1 | 1 | 1 | 4 | 1 |
| RE-2 | 1 | 1 | 5 | 5 | 3 | 5 | 5 | 5 | 3 | 5 | 1 | 1 |

Note)
3196/CEH, 3196/LP is 1:1 mixed oil of caprylyl methicone and corresponding organic oil

TABLE 8

Compatibility with hydrophobic oil agent (Group 2)

|  | 6 cs | 2 cs | D5 | 556 | 3196 | ID | IP | IOTG | CEH | LP | LP/JB | LP/SF |
|---|---|---|---|---|---|---|---|---|---|---|---|---|
| RT |  |  |  |  |  |  |  |  |  |  |  |  |
| No. 3 | 5 | 5 | 5 | 5 | 5 | 5 | 5 | 5 | 5 | 5 | 5 | 2 |
| No. 4 | 5 | 5 | 5 | 5 | 5 | 5 | 5 | 5 | 5 | 5 | 5 | 3 |
| RE-6 | 1 | 4 | 4 | 5 | 4 | 4 | 5 | 5 | 5 | 5 | 4 | 3 |
| RE-1 | 1 | 1 | 1 | 2 | 1 | 1 | 1 | 1 | 1 | 1 | 1 | 1 |
| 50 C. |  |  |  |  |  |  |  |  |  |  |  |  |
| No. 3 | 5 | 5 | 5 | 5 | 5 | 5 | 5 | 5 | 5 | 5 | 5 | 2 |
| No. 4 | 5 | 5 | 5 | 5 | 5 | 5 | 5 | 5 | 5 | 5 | 5 | 3 |
| RE-6 | 1 | 4 | 3 | 5 | 4 | 3 | 4 | 5 | 3 | 5 | 3 | 3 |
| RE-1 | 1 | 1 | 1 | 1 | 1 | 1 | 1 | 1 | 1 | 1 | 1 | 1 |
| 3 C. |  |  |  |  |  |  |  |  |  |  |  |  |
| No. 3 | 3 | 5 | 5 | 5 | 5 | 5 | 5 | 5 | 5 | 5 | 2 | 2 |
| No. 4 | 3 | 5 | 5 | 5 | 5 | 5 | 5 | 5 | 5 | 5 | 3 | 3 |
| RE-6 | 1 | 3 | 3 | 5 | 3 | 3 | 5 | 5 | 4 | 5 | 2 | 2 |

Note)
LP/JB, LP/SF are 1:1 mixed oil of liquid paraffin and corresponding vegetable oil Group 4 features extremely high viscosity of the modified silicone in an undiluted state, and thus should be practically handled or sold in a diluted state. Thus, compatibility of a blend product, diluted with dimethyl polysiloxane (2 cs) in advance to achieve the concentration of 37.5 for the modified silicone, with various oil agents was investigated. Note that the concentration of the modified silicone in a mixed solution including an oil agent is 10%, as in the test corresponding to Tables 7 and 8. The results are listed below.

TABLE 9

Compatibility with hydrophobic oil agent (Group 4)

|  | 20 cs | 10 cs | 6 cs | 2 cs | D5 | 556 | 3196 | ID | IP | 2 cs/ IOTG | 2 cs/ CEH | 2 cs/ LP |
|---|---|---|---|---|---|---|---|---|---|---|---|---|
| RT |  |  |  |  |  |  |  |  |  |  |  |  |
| No. 11 | 5 | 5 | 5 | 5 | 5 | 5 | 5 | 5 | 5 | 5 | 5 | 5 |
| No. 12 | 1 | 4 | 5 | 5 | 5 | 5 | 5 | 5 | 5 | 5 | 5 | 2 |

TABLE 9-continued

| Compatibility with hydrophobic oil agent (Group 4) | | | | | | | | | | | |
|---|---|---|---|---|---|---|---|---|---|---|---|
| 20 cs | 10 cs | 6 cs | 2 cs | D5 | 556 | 3196 | ID | IP | 2 cs/ IOTG | 2 cs/ CEH | 2 cs/ LP |
| No. 13 | | | | | | | | | | | |
| 5 | 5 | 5 | 5 | 5 | 5 | 5 | 5 | 5 | 5 | 5 | 5 |
| RE-8 | | | | | | | | | | | |
| 1 | 1 | 1 | 1 | 1 | 1 | 1 | 1 | 1 | 1 | 1 | 1 |
| 50 C. | | | | | | | | | | | |
| No. 11 | | | | | | | | | | | |
| 5 | 5 | 5 | 5 | 5 | 5 | 5 | 5 | 5 | 5 | 5 | 5 |
| No. 12 | | | | | | | | | | | |
| 1 | 5 | 5 | 5 | 5 | 5 | 5 | 5 | 5 | 5 | 5 | 5 |
| No. 13 | | | | | | | | | | | |
| 5 | 5 | 5 | 5 | 5 | 5 | 5 | 5 | 5 | 5 | 5 | 5 |
| RE-8 | | | | | | | | | | | |
| 1 | 1 | 1 | 1 | 1 | 1 | 1 | 1 | 1 | 1 | 1 | 1 |
| 3 C. | | | | | | | | | | | |
| No. 11 | | | | | | | | | | | |
| 5 | 5 | 5 | 5 | 5 | 5 | 5 | 5 | 5 | 5 | 5 | 5 |
| No. 12 | | | | | | | | | | | |
| 1 | 1 | 5 | 5 | 5 | 5 | 5 | 5 | 5 | 5 | 5 | 1 |
| No. 13 | | | | | | | | | | | |
| 5 | 5 | 5 | 5 | 5 | 5 | 5 | 5 | 5 | 5 | 5 | 5 |
| RE-8 | | | | | | | | | | | |
| 1 | 1 | 1 | 1 | 1 | 1 | 1 | 1 | 1 | 1 | 1 | 1 |

Note)
2 cs/IOTG, 2 cs/CEH, 2 cs/LP are mixed oil of dimethyl polysiloxane (2 cs) and the corresponding organic oil in a weight ratio of 2.25:4. The blend product obtained by diluting the modified silicone with 2 cs (weight ratio: 3.75) was mixed into the mixed oil, and the compatibility of the resultant oil was measured.

As described above, in all of the cases with the groups 1, 2, and 4, the tertiary-amine structure-containing polyhydric alcohol modified silicone according to the present invention has exhibited excellent compatibility with various types of hydrophobic oil agent, that is, adaptivity for wide variety of oil agents. Specifically, the silicone according to the present invention can transparently dissolve into various oil agents, and thus can diluted for reducing viscosity for improving productivity and usability, or enables the diluent to be selected from wide variety of diluents based on the client's preference. On the other hand, the polyether modified silicone and the other Comparative Example compounds involve the following drawback due to the hydrophilic modifier included as an impurity and their structural nature. Specifically, even if they have a transparent outer appearance, the dilution using an oil agent results in the outer appearance turns muddy due to precipitation of the hydrophilic modifier dissolved in the system or poor affinity with the oil agent. The muddiness is affected by temperature, moisture, and the like, and results in separation and sedimentation within a relatively short period of time because the viscosity of the diluent is low. In view of this, many conventional hydrophilic silicones can only be productized with high viscosity, and has low adaptivity to oil agents. Thus, the diluent cannot be easily selected. All things considered, both the degree of freedom for improving productivity, and a satisfaction level of the user side in terms of usability and performance are low.

One of the purposes for designing the Example compound group in the group 3 was to address the insufficient waterproofness of the comparative polyether modified silicone RE-7. This polyether modified silicone has feature of being water soluble to be easily compounded into a water system, while being a type of silicone which is generally regarded as hydrophobic. When water-based cosmetics (with water serving as the external phase) is formulated, in many cases, the designer would want to compound the oil agent component for the purpose of changing the feeling or the like. Of various oil agents, silicone oil features a light touch and excellent spreading performance, as well as excellent water repellency and safety. However, the silicon chain is hydrophobic in nature, and thus there has been a cumbersomeness that to compound the silicone into an aqueous phase, emulsification in water using a dedicated emulsifier with surfactant used in combination needs to be performed as preparation. Comparative polyether modified silicone RE-7 was a material made to solve this problem. The advantage of being easily compounded into water due to the water-soluble property involves a disadvantage of insufficient waterproofness. This is found to be the trade off in the structure design for the polyether modified silicone material.

The inventors of the present invention have figured out an approach based on the technical idea and chemistry of the present invention to obtain a material that is not water soluble, features excellent orientation and affinity with the skin surface to exhibit higher waterproofness, but still can also be easily compounded compounding in a case of formulating a water system. Specifically, the following processes have been found: 1) in the molecular design for the modified silicone according to the present invention, the amount of hydrophilic groups bonded to the silicone chain is designed to be smaller than the amount for making the modified silicone water-soluble, but is designed to be large enough for the modified silicone to dissolve into polyhydric alcohol such as PG, BG, and DPG. Thus, even when the mixed system including the modified silicone, water, and polyhydric alcohol in non-uniform, 2) the water-solubility of the modified silicone is extremely improved through the neutralization process including adding an acid substance, whereby the mixed system becomes transparent (the modified silicone can be easily compounded on side). 3) The hydrophobic part of the modified silicone is directed outward due to the orientation of the tertiary amine part relative to the skin surface, and thus effective waterproofness is obtained. The amount of the hydrophilic portion in a molecule is designed to be small as much as possible to prevent the material from being easily removed by a water flow. Data in the following Tables 10 to 14 indicates the effectiveness of the processes 1) and 2).

TABLE 10

| Compatibility with polar solvent (Group 3) Modified silicone concentration 10% | | | | | | | | |
|---|---|---|---|---|---|---|---|---|
| | H2O | SO | GL | PG | BG | DPG | EtOH | IPA |
| RT | | | | | | | | |
| No. 8 | 1 | 1 | 1 | 5 | 5 | 5 | 5 | 5 |
| No. 9 | 1 | 1 | 1 | 5 | 4 | 4 | 5 | 5 |
| No. 10 | 1 | 1 | 1 | 3 | 4 | 4 | 5 | 5 |
| RE-7 | 5 | 1 | 1 | 5 | 5 | 5 | 5 | 5 |
| RE-1 | 1 | 1 | 1 | 5 | 5 | 5 | 5 | 5 |
| RE-2 | 1 | 1 | 1 | 5 | 5 | 5 | 5 | 5 |
| 50 C. | | | | | | | | |
| No. 8 | 1 | 1 | 1 | 5 | 5 | 5 | 5 | 5 |
| No. 9 | 1 | 1 | 1 | 5 | 4 | 5 | 5 | 5 |
| No. 10 | 1 | 1 | 1 | 5 | 5 | 4 | 5 | 5 |
| RE-7 | 5 | 1 | 1 | 5 | 5 | 5 | 5 | 5 |
| RE-1 | 1 | 1 | 1 | 5 | 5 | 5 | 5 | 5 |
| RE-2 | 1 | 1 | 1 | 5 | 5 | 5 | 5 | 5 |

The results in Table 10 indicates that the example compound group itself is not soluble to solvents with extremely high polarity (such as water, 70% sorbitol aqueous solution, glycerin), but can substantially transparently dissolve into PG, BG, DPG, and EtOH used as water-based solubilizer/stabilizer and the like, resulting in a stable solution. Thus, Example compound in the group 3 is highly viscous in nature and thus is difficult to handle, but can be dissolved in polyhydric alcohol and ethanol as described above to be used/sold.

Next, the mixture solution obtained as described above is further diluted with water until the ratio 1:1 is achieved, and the outer appearance of the diluent is observed to evaluate the stability (compatibility) of the modified silicone in an alcohol/water mixed system. Here, the weight ratio among modified silicone:polar solvent:water is 1:9:10. The results are listed in the following Table 11.

TABLE 11

Compatibility with polar solvent/water mixture system
(Group 3) Modified silicone concentration 5%

|  | PG | BG | DPG | EtOH | IPA |
|---|---|---|---|---|---|
| RT |  |  |  |  |  |
| No. 8 | 1 | 1 | 1 | 5 | 5 |
| No. 9 | 1 | 1 | 1 | 2 | 5 |
| No. 10 | 1 | 1 | 1 | 1 | 5 |
| RE-7 | 5 | 5 | 5 | 4 | 5 |
| RE-1 | 3 | 4 | 3 | 5 | 5 |
| RE-2 | 1 | 1 | 1 | 5 | 5 |
| 50 C. |  |  |  |  |  |
| No. 8 | 1 | 1 | 1 | 5 | 5 |
| No. 9 | 1 | 1 | 1 | 5 | 5 |
| No. 10 | 1 | 1 | 1 | 1 | 5 |
| RE-7 | 5 | 5 | 5 | 5 | 5 |
| RE-1 | 3 | 3 | 3 | 5 | 5 |
| RE-2 | 1 | 1 | 5 | 5 | 5 |

The results indicate a distinct behavior of the insolubility of the example compound group against water compared with the Comparative Example sample group. This feature is advantageous in terms of duration of the effect and waterproofness after the diluent including the example compound group is applied to the skin, hair, or the like.

Next, of the mixture liquid obtained through the compatibility test so far, ones with non-transparent outer appearance was selected. Then, lactic acid of an equimolar amount or of a lightly excessive amount was added to the tertiary amino group in the modified silicon molecule used. The resultant liquid was mixed thoroughly to be homogenized, and then the outer appearance thereof was observed at 50° C. and at a room temperature. The results are listed in the following Tables 12 to 14. The evaluation points based on the same determination criteria as the one described above were used.

Table 12 indicates the outer appearances of liquid obtained by adding the above-described calculated amount of lactic acid to a sample, of the mixed liquid in Table 10, using water, 70% sorbitol aqueous solution, and glycerin as the polar solvent, and mixing the resultant liquid.

TABLE 12

Compatibility with polar solvent after neutralization
of modified silicone: Silicone concentration 10%

|  | H2O | SO | GL |
|---|---|---|---|
| RT |  |  |  |
| No. 8 | 3 | 5 | 3 |
| No. 9 | 3 | 5 | 3 |
| No. 10 | 3 | 3 | 3 |
| RE-1 | 4 | 2 | 3 |
| RE-2 | 3 | 1 | 1 |
| 50 C. |  |  |  |
| No. 8 | 1 | 4 | 5 |
| No. 9 | 1 | 4 | 3 |
| No. 10 | 1 | 3 | 3 |

TABLE 12-continued

Compatibility with polar solvent after neutralization
of modified silicone: Silicone concentration 10%

|  | H2O | SO | GL |
|---|---|---|---|
| RE-1 | 4 | 2 | 3 |
| RE-2 | 2 | 1 | 1 |

Table 13 includes a) a list indicating the outer appearance of liquid obtained by further diluting the mixed liquid in Table 12 with water until the ratio of 1:1 is achieved, and b) a list indicating the outer appearance of liquid obtained by adding the above-described calculated amount of lactic acid to the mixed liquid in Table 11, and then mixing the resultant liquid. By observing the outer appearances of these diluents, the stability (compatibility) of the modified silicone cationized (neutralized) in the alcohol/water mixed system can be understood.

TABLE 13

Compatibility with polar solvent/water mixture system after
neutralization of modified silicone: Silicone concentration 5%

|  | H2O | SO | GL | PG | BG | DPG | EtOH | IPA |
|---|---|---|---|---|---|---|---|---|
| RT |  |  |  |  |  |  |  |  |
| No. 8 | — | 5 | 5 | 5 | 5 | 5 | 5 | 5 |
| No. 9 | — | 4 | 4 | 4 | 4 | 5 | 5 | 4 |
| No. 10 | — | 3 | 3 | 4 | 5 | 5 | 5 | 3 |
| RE-1 | 5 | 1 | 1 | 3 | 3 | 4 | 5 | 5 |
| RE-2 | 1 | — | — | 5 | 5 | 5 | 4 | 5 |
| 50 C. |  |  |  |  |  |  |  |  |
| No. 8 | — | 5 | 5 | 5 | 5 | 5 | 5 | 5 |
| No. 9 | — | 5 | 5 | 4 | 5 | 5 | 5 | 4 |
| No. 10 | — | 4 | 2 | 4 | 5 | 5 | 4 | 4 |
| RE-1 | 1 | 1 | 1 | 3 | 3 | 3 | 5 | 5 |
| RE-2 | 1 | — | — | 5 | 5 | 5 | 4 | 5 |

The following Table 14 is a list indicating the outer appearances of samples obtained by selecting appropriate ones from the mixed liquid in Table 13 described above, further diluting the liquid with water until the concentration of the modified silicone drops to 1%. Note that a sample (with the components other than lactic acid added in an amount that is the same as that in other samples) including comparative polyether modified silicone RE-7 without the neutralization process is also illustrated for comparison. Here, the weight ratio among modified silicone:polar solvent:water is 1:9:90. The silicone concentration of around 1% is equivalent to a standard added among of a water-soluble silicone in a transparent cosmetic with a large compounded amount of water, such as skin toner, serum, hair styling lotion, hair restoring hair water. Thus, whether the transparent compounding is achieved with this concentration is practically most important.

TABLE 14

Compatibility with polar solvent/water mixture system after neutralization
of modified silicone: Silicone concentration 1%

|  | PG | BG | DPG | EtOH | IPA |
|---|---|---|---|---|---|
| RT |  |  |  |  |  |
| No. 8 | 5 | 5 | 5 | 5 | 5 |
| No. 9 | 5 | 5 | 5 | 5 | 5 |
| No. 10 | 5 | 5 | 5 | 5 | 4 |
| RE-7 | 5 | 5 | 5 | 5 | 5 |

TABLE 14-continued

Compatibility with polar solvent/water mixture system after neutralization of modified silicone: Silicone concentration 1%

|       | PG | BG | DPG | EtOH | IPA |
|-------|----|----|-----|------|-----|
| RE-1  | 1  | 3  | 3   | 2    | 3   |
| RE-2  | 3  | 3  | 4   | 3    | 5   |
| 50 C. |    |    |     |      |     |
| No. 8 | 5  | 5  | 5   | 5    | 5   |
| No. 9 | 5  | 5  | 5   | 5    | 5   |
| No. 10| 5  | 5  | 5   | 5    | 5   |
| RE-7  | 5  | 5  | 5   | 5    | 5   |
| RE-1  | 1  | 1  | 1   | 1    | 2   |
| RE-2  | 3  | 3  | 4   | 3    | 5   |

Specifically, the compound itself is water-insoluble, but can be transparently compounded into the system easily, through neutralization using an acid substance in a situation where the compound is to be compounded into a formulation including water and a polar solvent. The dilute solution (the weight ratio among modified silicone:polar solvent:water being 1:9:90) with a stable solubilized system maintained is extremely useful, and this should represent a dramatic improvement from the conventional techniques. Furthermore, the solution including the example compound in Table 14 stood for two month at a room temperature without changing its appearance and emitting almost no odor due to aging.

Emulsifying Ability for Forming Water-in-Oil Emulsion

A test for checking the emulsifying ability for forming the water-in-oil emulsion was conducted using comparative polyether modified silicone and Example compound as emulsifier (surfactant), and with the type of combined oil agent changed for each of the group described above (1, 2, and 4). Specifically, the water-in-oil emulsion compositions as illustrated in Tables 15 to 19 were prepared through the following procedure, and the viscosity stability, the stability of the diameter of the emulsified particle, odorization over time, and the like were evaluated based on the following evaluation criteria. Tables 15 to 19 further illustrate the results. In the tables, "parts" represents parts by weight (mass).

[Procedure for Preparing Water-in-Oil Emulsion Composition]

1. The oil agent and a silicone compound serving as an emulsifier were placed in a vessel with a volume of 1,200 ml.
2. The modified silicone was uniformly dispersed or dissolved in the oil agent by stirring (Oil Phase A).
3. Sodium chloride and ion-exchanged water were placed in another vessel and mixed to dissolve. In addition, BG was mixed therein and dissolved (Aqueous Phase B).
4. Saw teeth of a homodisper were immersed in the aforementioned Oil Phase A. Subsequently, while the aforementioned Oil Phase A was stirred at 1,000 rpm, the aforementioned Aqueous Phase B was poured into the aforementioned Oil Phase A at an approximately specified rate over about 45 seconds.
5. The mixture was further stirred for one minute after the revolutions per minute of the homodisper was increased to 3,000 rpm. The content was stirred for two minutes with this RPM to be homogeneously emulsified.
6. The homodisper was temporarily stopped, and oil attached to the inner wall of the vessel was scraped off using a spatula, to be mixed with the emulsion being produced.
7. The mixture was stirred again for three minutes with revolutions per minute of the homodisper set to be 3000 rpm, so that the content homogeneously emulsified.

[Evaluation of Outer Appearance]

28 g of each of the water-in-oil emulsion compositions was weighted into a 35 ml glass bottle. The bottle was sealed tightly and allowed to stand in a thermostatic chamber at 50° C. The stability of the outer appearance of the emulsion thereafter was evaluated in accordance with the evaluation criteria described below.

○: The emulsion had a uniform outer appearance

Δ: The surface of the emulsion was slightly nonuniform, or the emulsion surface had few water drops as a result of evaporation.

x: A large water drop or separation of the aqueous phase, the oil phase, and the like was clearly observed (x also provided for a failure to emulsify).

[Evaluation of Viscosity Stability]

The viscosity of the emulsion before and after the standing was measured with the temperature reset to 25° C. Then, the rate of change from the initial value was calculated.

[Evaluation of Odorization Over Time]

The odorization over time of the emulsion after being stood was checked with the temperature reset to 25° C., and was evaluated based on the following criteria.

⊚: No odor at all

○: Slight sweet specific odor

Δ: Somewhat strong sweet specific odor x: Strong sweet specific odor

[Measurement and Stability Evaluation for Emulsified Particle Diameter]

Observation using an optical microscope (×1,000) and image capturing were performed on emulsified particle as a result of the emulsion described above, before and after the standing. Then, the stability of the emulsified particle diameter in the initial state and after an elapse of time was evaluated.

⊚: Small change in emulsified particle diameter, and no sign of coalescence.

○: The emulsified particle diameter may be slightly increasing but not clear coalescence is observed, or the emulsified particle diameter increases but no large change in the particle size as a whole and thus the emulsification system is maintained.

Δ: Partial particle coalescence is found, and the increase in the emulsified particle diameter notable as a whole.

x: Coalescence of many particles occurring to almost ruin the emulsification (x also provided for a failure to emulsify).

Table 15 illustrates performance evaluation for a silicone compound in the group 1 described above, regarded as an emulsifier suitable for forming W/Si: water-in-"silicone oil" emulsion to W/(Si+O) water-in-"mixture oil of silicone oil and organic oil" emulsion.

TABLE 15

Results of formulation and evaluation for water-in-oil
(Example 14 to 19, Comparative Example 9 to 10), Standing period: 13 days

| Material name | Example | | | | | | Comparative Example | |
|---|---|---|---|---|---|---|---|---|
| | 14 | 15 | 16 | 17 | 18 | 19 | 9 | 10 |
| Silicone compound No. 1 | 2 | 2 | — | — | — | — | — | — |
| Silicone compound No. 2 | — | — | 2 | 2 | — | — | — | — |
| Silicone compound No. 5 | — | — | — | — | 2 | 2 | — | — |
| Polyether modified silicone RE-5 for comparison | — | — | — | — | — | — | 2 | 2 |
| Dimethylpolysiloxane (6 cst) | 23 | 11.5 | 23 | 11.5 | 23 | 11.5 | 23 | 11.5 |
| Mineral oil 50 SUS (37.8° C.) | — | 11.5 | — | 11.5 | — | 11.5 | — | 11.5 |
| Sodium chloride | 0.5 | 0.5 | 0.5 | 0.5 | 0.5 | 0.5 | 0.5 | 0.5 |
| Purified water | 68.5 | 68.5 | 68.5 | 68.5 | 68.5 | 68.5 | 68.5 | 68.5 |
| 1,3-butylene glycol | 6 | 6 | 6 | 6 | 6 | 6 | 6 | 6 |
| Stability of appearance | ○ | ○ | ○ | ○ | ○ | ○ | ○ | ○ |
| Initial viscosity value [mPas] | 18000 | 17000 | 18000 | 17000 | 21000 | 26000 | 9800 | 18000 |
| Viscosity change rate % | −25 | −5 | −21 | −22 | −38 | −35 | −54 | −4 |
| Odorization over time | ◎ to ○ | ◎ to ○ | ◎ to ○ | ◎ to ○ | ◎ to ○ | ◎ to ○ | ○ | ○ |
| Initial particle size (μm) | 1 to 5.2 | 1 to 5 | 1 to 5 | 1.5 to 5.5 | 1 to 4.5 | 1 to 5.3 | 0.5 to 5.2 | 0.5 to 4.5 |
| Particle size after aging (μm) | 3.5 to 7 | 2.5 to 6.7 | 2.5 to 6.7 | 2.5 to 6.7 | 2.5 to 7 | 3 to 10 | 1 to 4.8 | 0.5 to 6.7 |
| Stability of emulsified particles | ○ | ○ | ○ | ○ | ○ | △ | ◎ | ○ |

With a comprehensive determination based on the results described above, the example silicone compounds No. 1 and No. 2 can be regarded as having an emulsification ability comparable to that of the comparative polyether modified silicone RE-5. The emulsified particle diameter after the aging is larger than that of a comparative product, but a value of the emulsion viscosity is close between the formulation with the silicone oil only and the formulation with the oil mixed and is in a low viscosity range. This is an advantageous feature for designing an emulsified cosmetic based on the compounds. The rate of change in the viscosity after the aging is not as extreme as that of the comparative product. This is also an advantageous feature. The odorization over time was similar to or lower than that of the comparative product. The example silicone compound No. 5 can be regarded as having an emulsification ability substantially equal to that of the comparative product, in the case of the formulation with the silicone oil only, but was inferior to the comparative product in stability, in the case of the mixed oil system.

Table 16 and Table 17 illustrate performance evaluation for a silicone compound in the group 2, which is regarded as an emulsifier suitable for forming emulsion corresponding to wide variety of oil agents from W/Si: water-in-"silicone oil" emulsion to W/O: water-in-"organic oil" emulsion.

TABLE 16

Formulation and result of evaluation of water-in-oil
(Example 20 to 27), Standing period: 11 days

| Material name | Example | | | | | | | |
|---|---|---|---|---|---|---|---|---|
| | 20 | 21 | 22 | 23 | 24 | 25 | 26 | 27 |
| Silicone compound No. 3 | 2 | 2 | 2 | 2 | — | — | — | — |
| Silicone compound No. 4 | — | — | — | — | 2 | 2 | 2 | 2 |
| Dimethylpolysiloxane (6 cst) | 23 | 11.5 | — | — | 23 | 11.5 | — | — |
| Mineral oil 50 SUS (37.8° C.) | — | 11.5 | 23 | 11.5 | — | 11.5 | 23 | 11.5 |
| Sunflower oil | — | — | — | 11.5 | — | — | — | 11.5 |
| Sodium chloride | 0.5 | 0.5 | 0.5 | 0.5 | 0.5 | 0.5 | 0.5 | 0.5 |
| Purified water | 68.5 | 68.5 | 68.5 | 68.5 | 68.5 | 68.5 | 68.5 | 68.5 |
| 1,3-butylene glycol | 6 | 6 | 6 | 6 | 6 | 6 | 6 | 6 |
| Stability of appearance | ○ | ○ | ○ | ○ | ○ | ○ | ○ | ○ |
| Initial viscosity value [mPas] | 18000 | 11000 | 11000 | 67500 | 19000 | 11000 | 11000 | 64500 |
| Viscosity change rate % | +13 | +7 | +48 | −35 | +13 | +31 | +47 | −48 |
| Odorization over time | ◎ to ○ | ◎ to ○ | ◎ to ○ | ◎ | ◎ to ○ | ◎ to ○ | ◎ to ○ | ◎ |
| Initial particle size (μm) | 2.5 to 6 | 2 to 6 | 2 to 6 | 1.5 to 3.6 | 2 to 6.7 | 2 to 7 | 2 to 6.4 | 1.5 to 4.2 |
| Particle size after aging (μm) | 2.5 to 6.7 | 3 to 8 | 2 to 8 | 2 to 5.5 | 2 to 10 | 2 to 10 | 2 to 8 | 2.5 to 6 |
| Stability of emulsified particles | ◎ | ○ | △ | ○ | ○ | △ | ○ | ○ |

TABLE 17

Formulation and evaluation result of water-in-oil emulsion composition (Comparative Example 11 to 14), Standing period: 11 days

| Material name | Comparative Example | | | |
|---|---|---|---|---|
| | 11 | 12 | 13 | 14 |
| Polyether modified silicone RE-6 for comparison | 2 | 2 | 2 | 2 |
| Dimethylpolysiloxane (6 cst) | 23 | 11.5 | — | — |
| Mineral oil 50SUS (37.8° C.) | — | 11.5 | 23 | 11.5 |
| Sunflower oil | — | — | — | 11.5 |
| Sodium chloride | 0.5 | 0.5 | 0.5 | 0.5 |
| Purified water | 68.5 | 68.5 | 68.5 | 68.5 |
| 1,3-butylene glycol | 6 | 6 | 6 | 6 |
| Stability of appearance | ◯ | Δ through X | X Separated | ◯ |
| Initial viscosity value [mPas] | 17000 | 8000 | 8300 | 38500 |
| Viscosity change rate % | −14 | −44 | NA | −3 |
| Odorization over time | ◯ | ◯ | ◯ | ◎ |
| Initial particle size (μm) | 2 to 4.8 | 1 to 7.9 | 2 to 5.8 | 1 to 3 |
| Particle size after aging (μm) | 1 to 6.1 | 3.5 to 10 | NA | 0.5 to 4 |
| Stability of emulsified particles | ◎ | Δ | X Separated | ◎ |

The results described above indicates that a comparative polyether modified silicone RE-6 exhibited excellent initial emulsifiability, but was poor in aging stability in the case where the oil phase includes the non-polarity hydrocarbon oil (liquid paraffin) only and the case where the oil phase is a mixed oil including the silicone oil and liquid paraffin. Thus, the silicone resulted in emulsion involving separation and poor outer appearance. All things considered, this silicone is far from achieving stable emulsion for a wide variety of oil agent, under this test condition. On the other hand, the example silicone compounds No. 3 and No. 4 had the initial emulsifiability comparable to that of the comparative product, and achieved favorable emulsion involving stable outer appearance for all of the types of oils solutions. Some cases had the enlargement of the emulsified particle due to aging, in the case where the oil phase includes non-polarity hydrocarbon oil (liquid paraffin) only and in the case where the oil phase is the mixed oil of the silicone oil and liquid paraffin. Still, the emulsifiability can be regarded as being superior to that of the comparative product. In particular, both of these formulations achieved emulsion having an extremely low viscosity 11000 mPas and still also having an outer appearance stable (not ruined) after the aging. Thus, the emulsion has extremely high usability considering the fact that it is a low viscosity product that can provide a unique and excellent feeling in use. The oderization over time was equal to or smaller than that of the comparative product.

Considering the molecular structure of the emulsifier, the example silicone compounds No. 3 and No. 4 have an average chemical structure that is substantially the same as that of the comparative polyether modified silicone RE-6, except for the part of the hydrophilic group. Thus, based on the emulsification test, the tertiary-amine structure-containing polyhydric alcohol group according to the present invention can be expected to have the surface activity ability comparable to that of polyether groups, if the conditions regarding the silicone/organic ratio in the hydrophobic part, the balance and the size of the particle as a whole including the hydrophobic part and the hydrophilic part, and the compatibility with other materials are satisfied.

Table 18 and Table 19 illustrates results of performance evaluation of the silicone compound in the group 4, which is a viscosity increasing emulsifier that can form a stable water-in-oil emulsion for an oil phase including volatile oil with low viscosity and silicone oil with relatively high viscosity. Generally, emulsion with a high rate of volatile oil in the oil phase is likely to involve low viscosity and also a low specific gravity of the oil phase, and thus is likely to result in separation over time, due to a large difference between the oil phase and the aqueous phase emulsified and dispersed inside in the specific gravity. The risk of the separation increases as the temperature rises. Stabilization of such a formulation to a practically usable level is difficult with typical mid to low molecular hydrophilic silicone emulsifier, and requires the viscosity of the oil phase to be increased with an emulsifier of a high polymerization degree type. Meanwhile, a special formulation with silicone oil having high viscosity mainly compounded is available for the oil phase used for the water-in-oil emulsion, such as 10 to 100 cs. The stable emulsion and dispersion of the aqueous phase into a silicone oil with high viscosity is also difficult with a typical mid to low molecular hydrophilic silicone emulsifier, and is implemented with the emulsifer of a high polymerization degree type. The expected unique feature of the silicone compound in the group 4 is as described above.

In Table 18 and Table 19, the measurement of the viscosity and the emulsified particle diameter after the aging is omitted because all the emulsions had extremely stable outer appearance, and only the initial values of these are illustrated. The increase in the viscosity of the emulsion is an important factor for the emulsifier in the group. Thus, the rate of increase in the viscosity was calculated ("viscosity of emulsion"/"viscosity of oil agent used") and displayed.

TABLE 18

Formulation and result of evaluation of water-in-oil emulsion composition (Example 28 to 35) Standing period: One month

| Material name | Example | | | | | | | |
|---|---|---|---|---|---|---|---|---|
| | 28 | 29 | 30 | 31 | 32 | 33 | 34 | 35 |
| Mixture with 2 cs containing 37.5% silicone compound No. 12 | 5.33 | 5.33 | 5.33 | 5.33 | — | — | — | — |
| Mixture with 2 cs containing 37.5% silicone compound No. 13 | — | — | — | — | 5.33 | 5.33 | 5.33 | 5.33 |

TABLE 18-continued

Formulation and result of evaluation of water-in-oil emulsion composition
(Example 28 to 35) Standing period: One month

| Material name | Example | | | | | | | |
|---|---|---|---|---|---|---|---|---|
| | 28 | 29 | 30 | 31 | 32 | 33 | 34 | 35 |
| Dimethylpolysiloxane (2 cs) | 17.67 | — | — | — | 17.67 | — | — | — |
| Caprylyl methicone (2.8 cs) | — | 17.67 | — | — | — | 17.67 | — | — |
| Light liquid isoparaffin (4.2 cs) | — | — | 17.67 | — | — | — | 17.67 | — |
| Dimethylpolysiloxane (20 cs) | — | — | — | 17.67 | — | — | — | 17.67 |
| Sodium chloride | 0.5 | 0.5 | 0.5 | 0.5 | 0.5 | 0.5 | 0.5 | 0.5 |
| Purified water | 68.5 | 68.5 | 68.5 | 68.5 | 68.5 | 68.5 | 68.5 | 68.5 |
| 1,3-butylene glycol | 6 | 6 | 6 | 6 | 6 | 6 | 6 | 6 |
| Stability of appearance: After one month | ◎ | ◎ | ◎ | ◎ | ◎ | ◎ | ◎ | ◎ |
| Initial viscosity value [mPas] | 24500 | 28800 | 25000 | 200800 | 26800 | 27800 | 26800 | 200300 |
| Thickening factor | 12250 | 9931 | 5952 | 10040 | 13400 | 9586 | 6381 | 10015 |
| Initial particle size (μm) | 3 to 9.7 | 3 to 8.5 | 3.6 to 10 | 0.5 to 2.4 | 2.5 to 7.6 | 3 to 8.8 | 3 to 7.3 | 0.5 to 3 |
| Stability of emulsified particles (Initial) | ◎ to ○ | ○ | ○ | ◎ | ◎ to ○ | ○ | ◎ to ○ | ◎ |

TABLE 19

Formulation and result of evaluation of water-in-oil emulsion composition
(Comparative Example 15 to 18) Standing period: One month

| Material name | Comparative Example | | | |
|---|---|---|---|---|
| | 15 | 16 | 17 | 18 |
| Mixture with 2 cs containing 37.5% polyether modified silicone RE-8 for comparison | 5.33 | 5.33 | 5.33 | 5.33 |
| Dimethylpolysiloxane (2 cs) | 17.67 | — | — | — |
| Caprylyl methicone (2.8 cs) | — | 17.67 | — | — |
| Light liquid isoparaffin (4.2 cs) | — | — | 17.67 | — |
| Dimethylpolysiloxane (20 cs) | — | — | — | 17.67 |
| Sodium chloride | 0.5 | 0.5 | 0.5 | 0.5 |
| Purified water | 68.5 | 68.5 | 68.5 | 68.5 |
| 1,3-butylene glycol | 6 | 6 | 6 | 6 |
| Stability of appearance: After one month | ◎ | ◎ | ◎ | ◎ |
| Initial viscosity value [mPas] | 17500 | 14500 | 11500 | 95000 |
| Thickening factor | 8750 | 5000 | 2738 | 4750 |
| Initial particle size (μm) | 3 to 11 | 3 to 10 | 3 to 8 | 2 to 4.2 |
| Stability of emulsified particles (Initial) | Δ | Δ | Δ | ◎ |

As described above, the example silicone compounds No. 12 and No. 13 clearly achieved higher viscosity increasing and stabilizing performances, particularly for emulsion with a high rate of volatile oil, compared with the comparative polyether modified silicone RE-8. Specifically, the example sample group achieved an emulsion viscosity value that is approximately twice as high as that of the comparative example sample group, for all types of oil agents tested. The comparative polyether modified silicone RE-8 was capable of increasing the viscosity of the emulsion with an oil phase mainly including silicone oil, but had a disadvantage of not being capable of effectively increasing the viscosity of the emulsion with the oil phase mainly including the volatile hydrocarbon oil. Both of the example compounds have overcome this disadvantage. Furthermore, the example compound group can be determined to be superior to the comparative product in terms of pure emulsifiability, based on the resultant emulsified particle diameter and its condition.

It can be found that these example compound groups exhibit behavior that is unique and advantageous for viscosity management of the oil phase, by comparing the capability to increase the viscosity of the water-in-oil emulsion and data on the viscosity of the oil agent or compound illustrated in Table 6 described above, with those in the case of the comparative polyether modified silicone RE-8. Specifically, an easy-to-manufacture/handle solution mode with a low viscosity that is one tenth of that of the polyether modified silicone is obtained for a simple mixed system including oil agent and not including water. When added in the emulsion formulation to be used, the material can achieve the object of providing stability by increasing the viscosity of the system to be twice as high as that in the case of the polyether modified silicone. All things considered, the example compound group can be regarded as having an essential molecular feature of achieving viscosity behavior according to need or enabling management of oil phase viscosity, advantageous for both the manufacturer and the user. We believe that the silicone material with such a feature has not been heretofore known.

Sensation During Use Test Using Basic Formulation

Base on the performance evaluation described above, the silicone compounds No. 1, the silicone compound No. 3, the silicone compound No. 8 or No. 9, and the silicone compound No. 13 are determined to be most advantageous respectively in groups 1 to 4. Thus, the each of the example compounds described above was directly compared with the comparative polyether modified silicone in the same group, in terms of feeling on touch using a simple base formulation system.

[Evaluation on Feeling on Touch and Sensation During Use]: Group 1 and Group 2 (Applied Part: Skin)

Evaluation was made on the sensation during use and the waterproofness of the water-in-oil emulsion described above, applied on the skin as a cosmetic, at the time of application (including while the application is in progress) and after the application. The 1:1 relative comparison described above was performed on the emulsions with the same oil agent. Specifically, distinctive characteristics of the emulsion in terms of feeling on touch were recorded for each stage, and determined to be favorable or unfavorable. Then, the applied part was brought into contact with tap water flowing, and water repellency was monitored. The purpose of the tests was to investigate the essence of the characteristics of the component (modified silicone compound in this case) providing the feeling on touch, which is eminent with a simple formulation. The formulation needs to be usable as the base of the cosmetic (because if it is not, there is no point in investigating the feeling on touch in the first place).

[Procedure]
1. Using a finger, 0.20 ml of the water-in-oil emulsion composition was applied and spread on the back of the hand.
2. Characteristic feeling on touch at the time of application and during the application as well as a result of determining whether the feeling was good or bad were recorded.
3. Five minutes after the application, the characteristic feeling on the skin and a result of the determining where the feeling is good or bad was recorded.
4. 15 minutes after the application, the applied part (back of the hand) was brought into contact with the tap water flowing for approximately 30 seconds. The water repelling effect, represented by how the water hits the skin and roll down as droplets (roundness of the droplets, adhesion to the back of the hand, and the like), was determined and recorded.

[Criteria for Determining Whether Feeling on Touch is Good or Band] [Criteria for Determining Waterproofness]
◉: very comfortable ◎: extremely high water repellency
○: good ○: good water repellency
Δ: not good or bad, no characteristic Δ: some water repelling effect was observed
x: bad or uncomfortable x: almost no water repellency In the table below, a result of comparison between two types of W/Si emulsions in which only dimethyl polysiloxane (6 cs) was used as for oil agent, in feeling on touch and waterproofness.

TABLE 20

Results of evaluating feeling on touch of compound in grou1 in water-in-oil emulsion

| Oil phase: | Silicone compound No. 1 | | Example 9 (Polyether modified silicone RE-5) | |
|---|---|---|---|---|
| 6 cs Step | Determination | Characteristics | Determination | Characteristics |
| sensation during use at time of application | ◉ | Very fresh watery feeling on touch | ○ | Watery feeling on touch |
| sensation during use after application (after 5 minutes) | ◉ | Good moisture feel and skin protection feel maintained. Only little feeling of oil remaining | X | Dried feeling on skin. Uncomfortable feeling of thin oil film remaining. |

TABLE 20-continued

Results of evaluating feeling on touch of compound in grou1 in water-in-oil emulsion

| Oil phase: | Silicone compound No. 1 | | Example 9 (Polyether modified silicone RE-5) | |
|---|---|---|---|---|
| 6 cs Step | Determination | Characteristics | Determination | Characteristics |
| waterproofness (after 15 minutes) | ◎ | | Δ through X | |

The following table illustrates results of comparison between two types of W/(Si+O) emulsions, each using mixture of equal amounts of dimethyl polysiloxane (6 cs) and liquid paraffin as oil agent, in sensation during use and waterproofness

TABLE 21

Results of evaluation on feeling on touch of group 2 compound in water-in-oil emulsion

| Oil phase: | Example 21 (Silicone compound No. 3) | | Example 12 (Polyether modified silicone RE-6) | |
|---|---|---|---|---|
| 6 cs/LP Step | Determination | Characteristics | Determination | Characteristics |
| sensation during use at time of application | ○ | Richer watery feeling on touch than comparative product | Δ | — |
| sensation during use after application (after 5 minutes) | ◎ | Can feel good moisturizing effect and skin protection remaining, comfortable feeling on the skin | X | Dried feeling on skin, uncomfortable feel due to a large amount of remaining oil. |
| waterproofness (after 15 minutes) | ◎ | | ○ | |

Based on the evaluation result described above, it has been confirmed that the silicone compound No. 1 and the silicone compound No. 3 according to the present invention achieved a water-in-oil emulsion cosmetic with a great sensation during use at the time of application with rich watery feeling, as well as moisture feel and skin protection feel remaining for a while after the application. In particular, the product according to the present invention after the application had this great sensation during use in contrast to the uncomfortable oil remaining feeling of the polyether modified silicone according to Comparative Example.

Furthermore, the waterproof (water repellency) effect of the water-in-oil emulsion cosmetic base according to the present invention was an outstanding level. This is expected to be due to the fact that the tertiary-amine structure-containing polyhydric alcohol modified silicone according to the present invention has a molecular property to be effectively oriented on the skin surface, and has high purity with almost no impurity such as hydrophilic modifier included. This advantage should be a largely contributing factor, for a longer duration of effect and performance, in designing and manufacturing of makeup cosmetic, a sun care cosmetic, and a skin care cosmetic by compounding cosmetic powder, pigment, film forming agent, ultraviolet absorber, various chemicals, and the like with the water-in-oil emulsion cosmetic according to the present invention serving as the base.

[Evaluation on Feeling on Touch and Sensation During Use]: Group 3 (Applied Part: Skin)

The cationized silicone solution including the silicone compound No. 9 (or No. 8) in the group 3 (illustrated in Table 14 described above) at a concentration of 1% (the weight ratio among modified silicone:PG:water=1:9:90) was used as a cosmetic applied to the skin. The sensation during use at the time of (including during) the application and after the application, as well as duration against washing in running water were evaluated. A sample including the comparative polyether modified silicone RE-7 without the neutralization process (with the added amounts of components other than lactic acid being the same as those in other samples) was used as the comparative product for 1:1 relative comparison. Specifically, distinctive characteristics regarding the feeling on touch of each solution was recorded and whether the characteristic is good or bad was determined. Then, the applied part was washed with the other hand while being in contact with the running tap water, to evaluate the duration of the smoothness in the wet state.

[Procedure]

1. 0.3 ml of the silicone solution was sampled, placed on one of the hands, and spread by the other one of the hands.
2. Characteristic feeling on touch at the time of application and during the application as well as a result of determining whether the feeling was good or bad were recorded.
3. Five minutes after the application, the characteristic feeling on the skin and a result of the determining where the feeling is good or bad was recorded.
4. 15 minutes after the application, the applied part (back of the hand) was washed by the other hand while being in contact with running tap water, and the duration of the smooth feeling on touch during then was determined and recorded.

[Determination Criteria for Determining Whether Feeling on Touch is Good or Bad] [Duration Determination Criteria]
◎ very comfortable ◎: extremely favorable
○: good ○: favorable
Δ: not good or bad, or no characteristic Δ: normal level
x: bad or uncomfortable x: almost no duration Results of comparison between the two types of cationized silicone solutions and a polyether modified silicone solution in feeling on touch and duration are described below.

TABLE 22

Results of evaluating feeling on touch of group 3 compound in cationized silicone solution (1)

| Sample of Table 14 Polar solvent PG Step | Example (Silicone compound No. 9) | | Comparative Example (Polyether modified silicone RE-7) | |
|---|---|---|---|---|
| | Determination | Characteristics | Determination | Characteristics |
| sensation during use at time of application | ◎ | Very smooth and light application feel. Very fresh watery feeling on touch | Δ | No characteristics. Cannot identify what is applied. |
| sensation during use after application (after 5 minutes) | ○ | Smooth on the skin surface. Comfortable coating feel. A little sticky. | Δ | No characteristics. Small stickiness. |

TABLE 22-continued

Results of evaluating feeling on touch of group 3 compound in cationized silicone solution (1)

| Sample of Table 14 Polar solvent PG Step | Example (Silicone compound No. 9) | | Comparative Example (Polyether modified silicone RE-7) | |
|---|---|---|---|---|
| | Determination | Characteristics | Determination | Characteristics |
| duration in running water (after 15 minutes) | ○ | | X | |

TABLE 23

Results of evaluation on feeling on touch of group 3 compound in cationized silicone solution (2)

| Sample of Table 14 Polar solvent PG Step | Example (Silicone compound No. 8) | | Comparative Example (Polyether modified silicone RE-7) | |
|---|---|---|---|---|
| | Determination | Characteristics | Determination | Characteristics |
| sensation during use at time of application | X | Feel strong friction, very sticky | Δ | No characteristics. Cannot identify what is applied. |
| sensation during use after application (after 5 minutes) | X | Too much coating feel Strong friction and stickiness | Δ | No characteristics Small stickiness |
| duration in running water (after 15 minutes) | ◎ | | X | |

Based on a comprehensive determination on the results described above, of the group of compounds in the group 3, the silicone compound No. 9 should have a property that is most attractive to the market. As described above, we have found a type of silicone that has an excellent advantage of being capable of easily transparently compounded into a water base formulation through a neutralization operation, and has a characteristic of providing an excellent feeling on touch that is clearly different from existing water-soluble polyether modified silicone. Furthermore, we have confirmed the excellent duration of this effect. This means that the technical idea and its operation principle we found can be introduced to make the combination of a plurality of combinations of trade off and stereotypes according to the conventional technique completely obsolete.

The silicone solution containing the silicone compound No. 8 is highly favorable for achieving smooth sensation during use and its duration in running water (that is, an environment with an excessive amount of water). However, the solution provides no smoothness at all when applied to the skin in a normal state (an environment with an extremely small amount of water coexisting), and thus loses smoothness and lightness unique to silicones. We believe that this is attributable to an excessively high ratio of the hydrophilic group in molecules, resulting in a polarity of the hydrophilic group and increase in viscosity due to interference between the hydrophilic group and water affecting the characteristics of the feeling on touch of the surface.

Thus, the silicone compound No. 8 is recommended to be used as follows. Specifically, a small amount of compound may be added as a special oil agent for improving the feeling on touch, a cosmetics such as a hair conditioner and hair treatment requiring smoothness at the time of rinsing and duration of the smoothness. Such cosmetics generally use high polymerization dimethicone and high polymerization dimethiconol as a base oil agent (mainly for providing slipperiness to the hair in a dry state). Thus, with the compound described above used in combination with these, perfection of the cosmetic can be increased in terms of feeling on touch.

[Evaluation of Feeling on Touch and Sensation During Use]: Group 3 (Applied Part: Hair)

The cationized silicone solution including the silicone compound No. 9 in the group 3 (see Table 14 described above) at a concentration of 1% (the weight ratio among modified silicone:PG:water=1:9:90) was used as a cosmetic applied to the hair. The feeling on touch at the time of (including during) the application, during natural drying, and after the drying were evaluated. A sample including the comparative polyether modified silicone RE-7 without the neutralization process (with the added amounts of components other than lactic acid being the same as those in other samples) was used as the comparative product for 1:1 relative comparison. Specifically, distinctive characteristics regarding the feeling on touch of each solution was recorded and whether the characteristic is good or bad was determined.

[Procedure]

1. 1.5 ml of the silicone solution was sampled, placed on one of the hands, and applied to spread entirely over the hair on the same side as the hand (the right half or the left half).
2. The characteristic sensation during use at the time of application and during the application was recorded.
3. The characteristic feeling on touch during natural drying (5 to 25 minutes after the application) was recorded.
4. The characteristic feeling on touch in a state where the hair is complete dried (an hour after the application) was recorded.

The following table illustrates the results.

TABLE 24

Results of evaluating feeling on touch of group 3 compound in cationized silicone solution (3)

| Sample of Table 14 Polar solvent PG | Example (Silicone compound No. 9) | Comparative Example (Polyether modified silicone RE-7) |
|---|---|---|
| At time of application | No difference from Comparative Example in feeling on touch | Standard feeling on touch at time of application |
| Drying after application (5 to 25 minutes after) | Very smooth in wet state Good coating feel | Inferior smoothness (friction feel) in wet state. No good characteristic in terms of feeling on touch |
| After drying | Much higher slipperiness than Conventional Example | Good slipperiness |

It is clear from the results described above that the silicone solution including the silicone compound No. 9 can achieve excellent feeling on touch characteristics, different from that in the case where the polyether modified silicone is used, not only for the skin but also for the hair. In particular, the fact that this single pure compound can provide excellent slipperiness in both of the case where the hair is wet and the case where the hair is dry should be regarded as a large improvement from the conventional technique.

[Evaluation on Feeling on Touch and Sensation During Use]: Group 4 (Applied Part: Skin)

The compound of the group 4 can be expected to provide an effect unique to a modified silicone polymer with a high polymerization degree as described above. Furthermore, a solution and dispersion including a gum silicone with a high polymerization degree is known to serve as an oil agent base generally used for cosmetic purposes, to provide unique and excellent feeling on touch (the smoothness and the duration thereof not achievable by other materials). In view of the above, it is important to truly understand how the compound according to the present invention in the group 4 is different from the polyether modified silicone in the same group, in terms of the feeling on touch. Thus, the "mixture containing the silicone compound No. 13 and dimethyl polysiloxane (2 cs)" obtained in Example 13 described above, and the "mixture including the comparative polyether modified silicone RE-8 and dimethyl polysiloxane (2 cs)" obtained in Comparative Example 8 described above were used as oil blend cosmetics applied to the skin. Both mixtures containing the modified silicone at a concentration of 37.5%. The distinctive characteristics at the time of application (advantages and potential point of notes) were checked through comparison to be recorded.

[Procedure]

1. 0.13 g of the oil blend composition was extracted using a finger, and was applied on the back of the hand to be spread.
2. Characteristic sensory feature (smell and sensation during use) at the time of application and after the application was recorded.
3. After the application, the back of the hand was washed using a hand soap (foam type) and tap water. The duration, influence on the feeling on touch in a wet state, and the like of the coating film was checked and recorded.

The following table illustrates the results.

TABLE 25

Results of evaluation on sensation during use for group 4 compound in oil blend (1)

| Item | Example 13 (Silicone compound No. 13) | Comparative Example 8 (Polyether modified silicone RE-8) |
|---|---|---|
| Odor | Almost odorless | Strong remaining specific odor |
| Advantage in use | Skin protection effect and oil film with small greasiness, with good absorbability into skin and with small stickiness of oil film. | No distinctive characteristics but acceptable feel is obtained. Oil film can be washed off with hand soap |
| Potential point to be noted in use | Oil film difficult to wipe off even when hand soap is used, stickiness increases in wet state | Greasiness of oil film. No duration of oil film against hand soap |

[Evaluation of Feeling on Touch and Sensation During Use]: Group 4 (Applied Part: Hair)

Next, a sample using 2 cs/LP blend oil was selected as the hydrophobic oil agent to be used as a cosmetic applied to the hair, from oil blends containing the silicone compound in the group 4 (see Table 9 described above) at a concentration of 10%. Specifically, the distinct characteristic feeling on touch at the time of application was compared between the silicone compound No. 13 and the comparative polyether modified silicone RE-8 to be checked and recorded.

[Procedure]

1. 0.5 ml of the oil blend was sampled, placed on one of the hands, and applied to spread entirely over the hair on the same side as the hand (the right half or the left half).
2. The characteristic sensation during use at the time of application to after the application was recorded.

The following table illustrates the results.

TABLE 26

Results of evaluation on sensation during use for group 4 compound in oil blend (2)

| Sample of Table 9 Oil agent: 2 cs/LP | Example (Silicone compound No. 13) | Comparative Example (Polyether modified silicone RE-8) |
| --- | --- | --- |
| Advantage in feeling on touch | Better moisturizing effect | Better slipperiness |

The results illustrated in Table 25 and Table 26 described above clearly indicate the essential difference between the two types of silicone compounds in terms of feeling on touch characteristics. This can serve as an indication for a cosmetic designer designing the cosmetic in accordance with the form, application, and purpose of each cosmetic. Specifically, the indication indicates the effective way of introducing this new material into an actual highly complex cosmetic formulation (a combination with another oil agent for achieving synergy for better feeling on touch, the compounded amount, how the emulsification treatment is used, and a combination with agents and various types of powder).

For example, when a material is compounded into a cosmetic formulation at a high concentration, it is easier for the end consumer to directly feel the message and the concept of the designer providing the material with the characteristic feeling on touch and effects of the material. However, at the same time, this may result in a cosmetic with a simple function and expression, which is likely to be less interesting to the consumers soon or to be interesting to a specific group of consumers only. This is because the framework of the formulation is limited by the physico-chemical properties of the main material. On the other hand, the compounded amount of a characteristic material can be set to be in a low concentration region. In such a case, the unique feeling on touch and effect of the material are low. This is likely to result in a risk that identification of the product from other numerous general cosmetics (recognition of the distinctive value) is possible by only a highly sensitive consumer. Still, with this method, it may be easier to obtain a formulation achieving a synergic effect with which features of the other materials used in combination can make a large contribution. Furthermore, the method also has an advantage that the framework of the formulation would not be largely affected by a specific material.

All things considered, there is an advantage of enabling formulation to be implemented to achieve cosmetics with a higher level of perfection as a whole that can provide various functions and expressions and be in wide range of forms.

Cases where the feeling on touch was evaluated for an emulsion form with the concentration of the silicone compound in the group 4 lowered to 2%.

[Evaluation on Feeling on Touch and Sensation During Use]: Group 4 (Applied Part: Skin)

The water-in-oil emulsion according to Example 33 (Table 18 described above) and Comparative Example 16 (Table 19 described above) obtained by using the silicone compound in the group 4 were used as a cosmetic applied to the skin. The silicone compound No. 13 was compounded into the sample according to Example, and the comparative polyether modified silicone RE-8 was compounded in the sample according to Comparative Example. The weight ratios of the compounds in the emulsion were the same. The distinctive characteristics at the time of application (advantages and potential point of notes) were checked through comparison to be recorded.

[Procedure]

1. Using a finger, 0.20 ml of the water-in-oil emulsion composition was applied and spread on the back of the hand.
2. The characteristic sensation during use at the time of application to after the application was recorded.

TABLE 27

Results of evaluation on sensation during use of group 4 compound in water-in-oil emulsion (3)

| Oil agent system 3196/2 cs | Example 33 (Silicone compound No. 13) | Comparative Example 16 (Polyether modified silicone RE-8) |
| --- | --- | --- |
| Characteristic in terms of feeling on touch | duration of moisturizing effect, skin protection effect, comfortable coating feel | None |
| Potential point to be noted in use regarding feeling on touch | None | Dry feel, uncomfortable feel due to remaining thin oil film with low absorbability into skin |

As described above, Example 33 includes a) lowering the concentration of the silicone compound, b) increasing the compounded amount of the low viscosity oil agent for dilution, and c) water-in-oil emulsification was performed to effectively provide a watery feeling on touch. This formulation is simple enough to be regarded as the base of the cosmetic. Still, with only three little improvements, the formulation can emphasize many advantages of the silicone compound No. 13 of the present invention in terms of feeling on touch, without making the user feel disadvantages.

Applied Test (Group 3)

[Surface Tension]

The surface tension of the 1% cationized silicone solution that has been obtained (modified silicone:BG:water=1:9:90, see Table 14) for the silicone compounds No. 8 to No. 10 in the group 3. The surface tension of the sample (with the added amounts of the components other than lactic acid being the same as those in the sample described above) containing the comparative polyether modified silicone RE-7 at the same concentration not subjected to the neutralization (cationization) process was also measured for comparison. A mixed solution of BG:water=1:10 was used as a control sample.

The following device and measurement condition were employed.

Temperature: 18° C.

Device: Automatic surface tension meter, Digiomatic ESB-IV (KYOWA SCIENTIFIC CO.)

The following table illustrates the measurement results

TABLE 28

Surface tension value of 1% silicone solution

| Sample name or type of silicone | Surface tension value (mN/m) |
|---|---|
| Control | 31.7 |
| Polyether-modified silicone RE-7 for comparison | 29.1 |
| Silicone compound No. 8 (cationized) | 22.0 |
| Silicone compound No. 9 (cationized) | 21.0 |
| Silicone compound No. 10 (cationized) | 21.0 |

[Foaming Power]

Each 50 g of the above-described samples was put into a clean 100 ml glass bottle. The bottle was capped and shook vigorously for the mixing, and then was left standing. Then, 30 seconds later, the height of foam (the distance between the liquid surface and the topmost portion reached by the foam) was measured and recorded. The following table illustrates the measurement results

TABLE 29

Foaming power of 1% silicone solution

| Sample name or type of silicone | Height of foam (cm) |
|---|---|
| Control | 0 |
| Polyether-modified silicone RE-7 for comparison | 3.2 |
| Silicone compound No. 8 (cationized) | >4.2 |
| Silicone compound No. 9 (cationized) | 3.6 |
| Silicone compound No. 10 (cationized) | 2.0 |

It is clear from the results illustrated in Table 28 and Table 29 that the cationized silicone compounds No. 8 and No. 9 feature higher surface activity effect than the comparative polyether modified silicone RE-7. Thus, these compounds can be suitably compounded into a foam type cosmetic and the like with a non-ionic or cationic property, to be usable as an additive/foaming agent/surfactant with excellent feeling on touch improvement effect. On the other hand, the cationized silicone compound No. 10 features a high surface tension reduction effect and low foaming power, and thus is suitably used in a case where the main priority is rinsing without generating a large amount of foam, and for an application where the wetness and uniformity are important.

[Compatibility with Transparent Anionic Shampoo]

With no neutralization process, the silicone compounds No. 8 to No. 10 in the group 3 can be expected to behave as non-ionic molecules, depending on a formulation environment in which the compounds are compounded. Thus, transparency of the outer appearance and foaming property were evaluated for a hair cleaning cosmetic prepared by compounding a PG solution (no neutralization) with the modified silicone illustrated in Table 10 at a concentration of 10%, into a transparent shampoo base with a main component including anionic surfactant and amphoteric surfactant. A solution containing the comparative polyether modified silicone RE-7 was used as Comparative Example, and PG was directly use as the control. The following table illustrates a formulation of the hair cleaning cosmetic.

TABLE 30

Formulation of hair cleaning cosmetic (transparent type)

| Component | Wt % |
|---|---|
| Sodium POE(2) laurylether sulfate (27% aqueous solution) | 46.3 |
| Cocamidopropyl betaine (30% aqueous solution) | 8.3 |
| Ion-exchanged water | 35.4 |
| 10% modified silicone solution (not neutralized) | 10.0 |

Procedures for preparation and evaluation on outer appearance/foamability and the like are described below in detail

[Procedure Etc.]

1. The material was prepared at a total scale of 10.0 g by using a glass bottle with a volume of 20 ml.
2. The three components other than the modified silicone solution were put into the glass bottle. Then, the bottle was capped and shook so that the components are mixed and dissolved.
(Transparent Shampoo Base)
3. The 10% modified silicone solution was added to the transparent shampoo base thus obtained. Then, the bottle was capped and further shook to homogenize the content.
4. The resultant sample was allowed to stand in a thermostatic chamber at 50° C. for one night. Then, the outer appearance of the sample was recorded.
5. The sample was put back to the room temperature, and then the outer appearance was recorded.
6. The sample was vigorously shook for 20 times, and then was allowed to stand for 60 seconds. Then, the height of the foam (the distance between the liquid surface and the topmost portion reached by the foam) was measured and recorded.

The following table illustrates the results.

TABLE 31

Stability and foaming property of hair cleaning cosmetic (transparent type)

| Sample name or type of silicone | Appearance (50° C./RT) | Height of foam (cm) |
|---|---|---|
| Control | Transparent solution/ Transparent solution | 34.5 |
| Polyether-modified silicone RE-7 for comparison | Transparent solution/ Transparent solution | 35.0 |
| Silicone compound No. 8 | Transparent solution/ Transparent solution | 38.5 |
| Silicone compound No. 9 | Transparent solution/ Transparent solution | 34.5 |
| Silicone compound No. 10 | Transparent solution/ Transparent solution | 33.5 |

As described above, the silicone compounds No. 8 to No. 10 in the group 3 subjected to the neutralization process were confirmed to dissolve into the anionic transparent shampoo base, and thus was confirmed to be capable of being stably transparently compounded. Among the compounds, the silicone compounds No. 8 and No. 9 can be regarded as a feeling on touch improving agent that almost does not compromise the foaming power of the base surfactant component or can even increase the foaming power. Thus, the compounds can be expected to improve the feeling on touch as well as the cleaning effect of the shampoo during use. Furthermore, a hair cleaning cosmetic containing such example compound maintained its outer appearance as transparent liquid after storage for two month at a room temperature, and was completely odorless.

The above describe results of the applied test for the silicone compound in the group 3 demonstrate the essence of the dual ionicity of the novel tertiary-amine structure-containing polyhydric alcohol modified silicone according to the present invention, and how it can be used. Thus, the silicone enables ionic management so that its various properties such as performance and solubility can meet various demands on the user side, not only at the time of designing the structure or the time of manufacturing, but also on site (compounding to a formulation or even at the time of use).

Applied Test (Group 4)

A polar solvent type emulsion composition in oil with a structure illustrated in Table 32 was prepared through the following procedure. Then, the stability of the composition over time (outer appearance and odorization over time) was evaluated based on the following evaluation criteria. Table 32 further illustrates the results. In the tables, "parts" represents parts by weight (mass).

[Procedure for Preparing Polar Solvent-in-Oil Type Emulsion Emulsion]

1. The oil agent and a silicone compound serving as an emulsifier were placed in a vessel with a volume of 1,200 ml.
2. The modified silicone was dissolved in the oil agent by stirring (Oil Phase A).
3. The polar solvent and various additives were placed in another vessel, and mixed (further heated to approximately 50° C. if necessary) to dissolve (Polar Solvent Phase B).
4. Saw teeth of a homodisper were immersed in the aforementioned Oil Phase A. Subsequently, while the aforementioned Oil Phase A was stirred at 1,000 rpm, the aforementioned Polar Solvent Phase B was poured into the aforementioned Oil Phase A at an approximately specified rate over about 45 seconds.
5. The mixture was further stirred for one minute after the revolutions per minute of the homodisper was increased to 3,000 rpm. The content was stirred for two minutes with this RPM to be homogeneously emulsified.
6. The homodisper was temporarily stopped, and oil attached to the inner wall of the vessel was scraped off using a spatula, to be mixed with the emulsion being produced.
7. The mixture was stirred again for three minutes with revolutions per minute of the homodisper set to be 3000 rpm, so that the content homogeneously emulsified.

[Measurement of Viscosity]

The viscosity of the water-in-oil emulsion composition thus obtained at 25° C. was measured and recorded.

[Measurement of Stability of Appearance]

28 g of the water-in-oil emulsion composition was weighted into a 35 ml glass bottle. The bottle was sealed tightly and allowed to stand in a thermostatic chamber at 50° C. The stability of the outer appearance of the emulsion thereafter was evaluated in accordance with the evaluation criteria described below.

○: The emulsion had a uniform outer appearance
Δ: The surface of the emulsion was slightly nonuniform, or the emulsion surface had few water drops as a result of evaporation.
x: A large water drop or separation of the aqueous phase, the oil phase, and the like was clearly observed (x also provided for a failure to emulsify).

[Evaluation of Odorization Over Time]

The odorization over time of the emulsion after being stood was checked with the temperature reset to 25° C., and was evaluated based on the following criteria.
◉: No odor at all
○: Slight sweet specific odor
Δ: Somewhat strong sweet specific odor
x: Strong sweet specific odor The evaluation results are listed below.

TABLE 32

Formulation and evaluation result of polar solvent-in-oil type emulsion

| | Material name | Example 37 | Example 38 | Example 39 |
|---|---|---|---|---|
| Oil phase A | Silicone compound No. 13 (stock solution) | 2 | — | — |
| | Mixture with 2 cs containing 37.5% silicone compound No. 11 | — | 5.33 | 5.33 |
| | Dimethylpolysiloxane (6 cs) | 23 | — | — |
| | Caprylyl methicone (2.8 cs) | — | 17.67 | 17.67 |
| Polar solvent phase B | Sodium acetate | 0.5 | — | — |
| | 1,3-propylene glycol | 74.5 | — | — |
| | Ion-exchanged water | — | 68.5 | 68.5 |
| | Salt | — | 0.5 | 0.5 |
| | 1,3-butylene glycol (BG) | — | 6.0 | 6.0 |
| | 90% Lactic acid | — | 0.04 | — |
| Initial viscosity value [mPas] | | 48000 | 56800 | 17000 |
| Stability of appearance | | ○ | ○ | ○ |
| Odorization over time | | ◉ | Δ through X | ○ |
| 50° C. Standing period | | 1 week | 1 month | 1 month |

With the test in Example 37, the stable polyol-in-silicone oil (Polyol/Si) type emulsion was obtained. Using the framework of this formulation, agent that is unstable and likely to dissolve in an aqueous phase, such as vitamin C, may be dissolved in a polyol phase to be protected, to obtain an emulsion type cosmetic or preparation for external use that can effectively maintain and provide the efficacy of the agent. For example, this may be applied to a skin care cosmetic/preparation for external use for lightening and aging care. To further improve stability and achieve varying sensation during use, it is effective to add a paste form composition, obtained by uniformly dispersing cross-linked silicone particle such as a silicone elastomer blend into a silicone oil and the like, to the oil phase.

The emulsion obtained in Example 38 may be in a form of a water-in-oil cationic emulsion. Example 39 is a formulation that is the same as that of Example 38, except for the fact that the aqueous phase includes no lactic acid for notarization, and the composition to be obtained is a water-in-oil emulsion (non-ionic). The modified silicone compound of a high polymerization degree type according to Example, including a large hydrophobic part and a small number of hydrophilic parts seems to be covering the oil water interface so that the aqueous phase can be stably dissolved into the oil phase. It is expected that with this property of the polymer surfactant, a simple emulsification process on an acidic aqueous phase results in water-in-oil emulsion (with oil serving as the external phase), as in the case of the emulsification process on a neutral aqueous phase, and then a tertiary amine part of the surfactant molecule is gradually neutralized and cationized through reaction with acid. Both emulsions exhibited excellent stability of the outer appearance, but only the formulation with acid added exhibited oderization over time (sweet solvent odor). The effect of the cationization is extremely eminent in a formulation with water in the external phase, as in the application example of the group of compounds in the group 3. A method of cationizing the hydrophilic part of the emulsifier molecule for the formulation with oil serving as the external phase, leads to a sudden and large change in the hydrophilic/lipophilicity balance of the balance, which is expected to result in an emulsion system that is likely to be stable. Example 38 was described herein because the concept of cationic W/O emulsion seemed to be peculiar, and because it resulted in a material with a stable outer appearance. However, in principle, this example may be a technical method that is difficult to practically use.

The emulsion of Example 39 exhibited excellent stability over time. Thus, using the framework of this formulation, an oil-in-polyol aqueous solution type emulsion with transparent outer appearance may be obtained through an emulsification process performed in a state where a refractive index of the aqueous phase and the oil phase matched by adding an appropriate amount of glycerin and the like to the aqueous phase.

Example 40 to 45: Example of Synthesis of Silicone Compound According to Present Invention In addition to the silicone compounds No. 1 to 13 described above, an epoxy modified silicones with different polymerization degrees (DP) were synthesized, the silicone compound according to the present invention was synthesized through ring-opening reaction between the epoxy modified silicone and a secondary amine compound having a hydroxyl group (diethanolamine (DEA) or diisopropanolamine (DIPA)). Note that "Me" represents a methyl group, "M" represents a Me$_3$SiO group (or an Me$_3$Si group), "D" represents an Me$_2$SiO group, "M$^H$" represents an HMe$_2$SiO group (or an HMe$_2$Si group), "D$^H$" represents an HMe$_2$SiO group, and "M$^{AGE}$" or "D$^{AGE}$" represents an epoxy modified unit obtained by reacting allyl glycidyl ether with silicon atom-bonded hydrogen atom of M$^H$ or D$^H$.
[Synthesis of Terminal Epoxy Modified Siloxane (MAGED98MAGE) with Polymerization Degree of 100]

96.42 g of poly dimethyl siloxane with a molecular chain terminal having a dimethyl hydrogen siloxy group (M$^H$), having a siloxane polymerization degree (dp) of 100, and 3.58 g of allyl glycidyl ether were placed in a 3 neck flask and were heated to 40° C. When 40° C. was reached, an IPA solution (hydrosilylation reaction catalyst) including a platinum complex of hexamethyldisiloxane at a concentration of 1.1% was added. As a result, the reaction solution was heated to 51.1° C. The reaction solution was further heated to 60° C., and the reaction was completed after one hour at 60° C. An excess amount of isomerized allyl glycidyl ether was removed from the solution through stripping performed for three hours with 5 mm of Hg at 90° C. Thus, pure terminal epoxy modified siloxane (M$^{AGE}$D$_{98}$M$^{AGE}$) with a polymerization degree of 100 was obtained.

Example 40: Ring-Opening Reaction with Diethanolamine (DEA)

52.53 g of the terminal epoxy modified siloxane (M$^{AGE}$D$_{98}$M$^{AGE}$) with a polymerization degree of 100, 1.2 g of diethanolamine. And 30 g of IPA were placed in the 3 neck flask, and were heated to 75° C. The reaction solution was held for 23 hours at 75° C., and the ring-opening reaction was performed. After the reaction, the IPA was removed from the solution using through a four hour operation of a rotary evaporator (water bath at 80° C., and reduced pressure of 3 mbar). As a result, tertiary-amine structure-containing polyhydric alcohol modified silicone (denoted by M*D$_{98}$M*) with a polymerization degree of 100, and with both siloxane chain terminals having a functional group described later. Only a trace amount of IPA was detected.

Note that "M" denotes a monosiloxy unit represented by SiO(CH$_3$)$_2${C$_3$H$_6$O—CH$_2$CH(OH)CH$_2$—N(CH$_2$CH$_2$OH)$_2$}.

Example 41: Ring-Opening Reaction with Diisopropanolamine (DIPA)

51.50 g of the terminal epoxy modified siloxane (M$^{AGE}$D$_{98}$M$^{AGE}$) with a polymerization degree of 100, 1.81 g of diisopropanolamine, and 35 g of IPA were placed in the 3 neck flask, and were heated to 75° C. The solution was held for 48 hours at 75° C., and the ring-opening reaction was performed. After the reaction, the IPA was removed from the solution through simple distillation (no pressure reduction) at 90° C. for three hours. As a result, tertiary-amine structure-containing polyhydric alcohol modified silicone (denoted by M**DM*$_{98}$*) with a polymerization degree of 100, and with both siloxane chain terminals having a functional group described later. Only a trace amount of IPA was detected. Note that "M**" denotes a monosiloxy unit represented by SiO(CH$_3$)$_2$ {C$_3$H$_6$O—CH$_2$CH(OH)CH$_2$—N{CH$_2$CH(CH$_3$)—OH}$_2$}.
[Synthesis of MD$_{381}$D$^{AGE}_{7.5}$M]

97.3 g of methyl hydrogen polysiloxane (denoted by MD$_{381}$D$^H_{7.5}$M) and 3.40 g of allyl glycidyl ether were placed in a 3 neck flask and were heated to 42° C. When 42° C. was reached, an IPA solution (hydrosilylation reaction catalyst) including a platinum complex of hexamethyldisiloxane at a concentration of 1.1% was added. As a result, the reaction solution was heated to 43.3° C. The reaction solution was further heated to 70° C. As a result, the solution has reached 79° C. due to the progress of the heating reaction, and was then cooled down to 75° C. The reaction was completed when the temperature dropped to 75° C. An excess amount of isomerized allyl glycidyl ether was removed from the solution through stripping performed for three hours with 5 mm of Hg at 90° C. Thus, epoxy modified siloxane (MD$_{381}$D$^{AGE}_{7.5}$M) was obtained.

Example 42: Ring-Opening Reaction with Diethanolamine (DEA)

62.99 g of the epoxy modified siloxane (MD$_{381}$D$^{AGE}_{7.5}$M), 1.6 g of diethanolamine, and 40 g of IPA were placed in a 3 neck flask, and were heated to 75° C. The solution was held for 24 hours at 75° C., and the ring-opening reaction was performed. After the reaction, the IPA was removed from the solution using through a four hour operation of a rotary evaporator (water bath at 80° C., and reduced pressure of 3 mbar). As a result, tertiary-amine structure-containing polyhydric alcohol modified silicone (denoted by MD$_{381}$D*$_{7.5}$M) was obtained as an end product, with 0.01% by mass of IPA remaining. Note that "D*" denotes a disiloxy unit represented by
SiO(CH$_3$) {C$_3$H$_6$O—CH$_2$CH(OH)CH$_2$—N(CH$_2$CH$_2$OH)$_2$}.

Example 43: Ring-Opening Reaction with Diisopropanolamine (DIPA)

57.03 g of the epoxy modified siloxane (MD$_{381}$D$^{AGE}_{7.5}$M), 1.84 g of diisopropanolamine, and 30 g of IPA were placed in a 3 neck flask and were heated to 75° C. The solution was held for 24 hours at 75° C., and the ring-opening reaction was performed. Then, 0.52 g of diisopropanolamine was further added, and the reaction was further performed for 24 hours. After the reaction, the IPA was removed from the solution through simple distillation (no pressure reduction) at 90° C. for three hours. As a result, tertiary-amine structure-containing polyhydric alcohol modified silicone (denoted by $MD_{381}D^*_{7.5}M$) was obtained as an end product. Only a trace amount of IPA was detected. Note that "D**" is
a disiloxy unit represented by $SiO(CH_3)$ {—$C_3H_6O$—$CH_2CH(OH)CH_2$—$N\{CH_2CH(CH_3)$—$OH\}_2\}$.

Example 44: Ring-Opening Reaction with Diethanolamine (DEA)

50.53 g of epoxy siloxane denoted by $MD_{298}D^{AGE}_2M$, synthesized in a manner that is the same as that for the epoxy modified siloxane described above, 0.47 g of diethanolamine, and 30 g of IPA were placed in a neck flask, and were heated to 75° C. The solution was held for 24 hours at 75° C., and the ring-opening reaction was performed. After the reaction, the IPA was removed from the solution through simple distillation (no pressure reduction) at 90° C. for three hours. As a result, tertiary-amine structure-containing polyhydric alcohol modified silicone (denoted by $MD_{298}D^*_2M$) was obtained as an end product. 0.02% my weight of IPA remained.
Note that "D*" denotes a disiloxy unit represented by is a disiloxy unit represented by $SiO(CH_3)$ {$C_3H_6O$—$CH_2CH(OH)CH_2$—$N(CH_2CH_2OH)_2\}$.

Example 45: Ring-Opening Reaction with Diisopropanolamine (DIPA)

55.17 g of epoxy siloxane denoted by $MD_{298}D^{AGE}_2M$, synthesized in a manner that is the same as that for the epoxy modified siloxane described above, 0.65 g of diisopropanolamine, and 25 g of IPA were placed in a neck flask, and were heated to 75° C. The solution was held for 48 hours at 75° C., and the ring-opening reaction was performed. After the reaction, the IPA was removed from the solution through simple distillation (no pressure reduction) at 90° C. for three hours. As a result, tertiary-amine structure-containing polyhydric alcohol modified silicone (denoted by $MD_{381}D^*_{7.5}M$) was obtained as an end product. Only a trace amount of IPA was detected. Note that "D**" is
a disiloxy unit represented by $SiO(CH_3)$ {—$C_3H_6O$—$CH_2CH(OH)CH_2$—$N\{CH_2CH(CH_3)$—$OH\}_2\}$.

Hereinafter, formulation examples of the cosmetic and the external use preparation according to the present invention are described, but it is understood that the cosmetic and the external use preparation according to the present invention are not limited to the types and compositions recited in these formulation examples.

The novel modified organopolysiloxane with a side chain having the specific tertiary-amine structure-containing hydrophilic functional group according to the present invention or a composition including the same can be used for various preparations for external use and cosmetics. Specific formulation examples include: a formulation obtained by replacing components corresponding to the "silicone compound No. 1 to No. 16" in formulation examples for various cosmetics and preparations for external use disclosed in Examples and the like in Patent Document 1 (WO2011/049248) with the silicone compounds No. 1 to No. 13 according to the present invention; a formulation obtained by replacing components corresponding to the "silicone compound No. 1 to No. 8" in Example and formulation examples for various cosmetics and preparations for external use described in Patent Document 2 (WO2012-015070) with the silicone compounds No. 1 to No. 13 according to the present invention; and a formulation obtained by replacing components corresponding to the "silicone compound No. 1 to No. 14" in formulation examples for various cosmetics and preparations for external use described in Patent Document 3 (WO2011-049247) with the silicone compounds No. 1 to No. 13 according to the present invention. When a polyether modified silicone is used in these formulation examples, the polyether modified silicone may be totally replaced as appropriate with the novel modified organopolysiloxane with a side chain having the specific tertiary-amine structure-containing hydrophilic functional group according to the present invention to design PEG-free formulations. Furthermore, the acid-neutralized product of the silicone compound according to the present invention can optionally be included in the formulation examples of the various cosmetics and preparation for external uses, based on some of the guide lines related to the ionic management described in Example described above or the specification.

Formulation examples of the cosmetic and the preparation for external use according to the present invention include the following. In the description below, "parts" represents parts by mass (weight).

Formulation Example 1: Hair Conditioner (Components)
1. Cetanol, 5.6 parts
2. Stearyl trimonium chloride (70%), IPA solution, 1.5 parts
3. Behentrimonium chloride (80%), IPA solution, 0.8 parts
4. Mineral oil, 1.0 part
5. Glycerin, 2.0 parts
6. Dipropylene glycol, 6.6 parts
7. Ion-exchanged water, 76.5 parts
8. Preservative, appropriate amount
9. Dimethicone 3000 cs, 1.0 part
10. Phenyl trimethicone, 2.0 parts
11. Caprylyl methicone, 2.0 parts
12. Dimethicone 2 cs solution containing 37.5% silicone compound No. 13, 1.0 part
13. 90% Lactic acid, 0.1 part
14. Perfume, appropriate amount
[Method of Production]
Step 1: Components 1 to 4 are placed in a vessel, heated to 80° C., and stirred and mixed to dissolve.
Step 2: Components 5 to 8 are mixed in another vessel, and are heated to 80° C.
Step 3: The solution obtained in Step 2 is slowly added to the solution obtained in Step 1 being stirred, the mixture is further stirred and mixed with the temperature maintained at 80° C.
Step 4: When the mixture is homogenized as a whole, the mixture is slowly cooled down to 40° C. while being stirred. (Preparation of conditioner base)
Step 5: Components 9 to 12 are mixed in another vessel to be homogenized.
Step 6: The mixture solution obtained in Step 5 is added to the conditioner base obtained in Step 4, and the resultant solution is thoroughly stirred and mixed to be homogenized.
Step 7: Component 13 is further added, and resultant solution is thoroughly stirred and mixed to be homogenized.

Step 8: Component 14 is further added, and resultant solution is thoroughly stirred and mixed to be homogenized.

Advantageous Effects

The hair can have a feeling on touch with extremely high smoothness, at every stages including: at the time when the conditioner is applied to the hair; when the hair is rinsed with hot water (rinsing); when the hair is wipe dried with a towel; during natural drying; and after the hair is dried. The conditioner also features excellent stability, and involved only a slight viscosity reduction and oderization over time.

Formulation Example 2: Hair Lotion (Bed Hair Cure)

(Components)
1. Stearyl trimonium chloride, 0.1 part
2. Lauryl glucoside, 0.1 part
3. Pentylene glycol, 4.0 parts
4. Olive leaf extract, 0.05 part
5. Ceramide 3 (or any desirable medicinal properties), 0.05 part
6. Ethanol, 10.0 parts
7. Silicone compound No. 9, 1.0 part
8. Propylene glycol, 9.0 parts
9. Phenoxyethanol, 0.2 part
10. Perfume, appropriate amount
11. Ion-exchanged water, 71.3 parts
12. Glycerin, 3.0 parts
13. D-pantothenyl alcohol, 1.0 part
14. Hydrolyzed silk, 0.1 part
15. 90% Lactic acid, 0.2 part
[Method of Production]
Step 1: The components 1 to 10 are mixed and stirred to dissolve.
Step 2: The components 11 to 15 are mixed and stirred to dissolved.
Step 3: The solution obtained in Step 2 is slowly added to the solution obtained in Step 1 being stirred, and the resultant solution is homogenized.

Advantageous Effects

The conditioner provides smooth feeling on touch to the hair, enables fingers to smoothly run through the hair at the time of application, and provides excellent moist sensation during use. The product exerts an excellent bed head fixing effect, and makes the hair easy to style. Furthermore, moisturizing effect and smoothness continues after the hair is dried. The product also features excellent transparency.

Formulation Example 3: Lotion (Components)
1. Sodium stearoylglutamate, 0.25 part
2. N-(hexadecyloxy hydroxypropyl)-N-hydroxyethylhexadecanamide, 0.5 part
3. Glycerin, 15.0 parts
4. Polyoxyethylenemethyl glucoside, 0.5 part
5. Polyethylene glycol 1540, 0.5 part
6. Phenoxyethanol, 0.3 part
7. Paraben, 0.2 part
8. Allantoin (or any desirable medicinal properties), 0.2 part
9. Butylene glycol, 5.0 parts
10. Silicone compound No. 9, 0.6 part
11. Glutamic acid, 0.3 part
12. Trimethylglycine, 3.0 parts
13. Citrus junos extract, 0.5 part
14. Eugenia caryophyllata extraction liquid, 0.1 part
15. Ion-exchanged water, 73.05 parts
[Method of Production]
Step 1: The components 1 to 7 and a part of the component 15 are mixed and then are heated at 80 to 90° C. to be dissolved.
Step 2: The component 8 is mixed with a part of the component 15 and are heated at 80 to 90° C. to be dissolved.
Step 3: The mixture solution obtained in Step 2, heated to 80° C. or higher, is added to the solution obtained in Step 1 under stirring, and the emulsification process is performed at 80° C. The resultant emulsion is cooled down to a room temperature.
Step 4: In a separate vessel, the components 9 and 10 are mixed to dissolve.
Step 5: In a separate vessel, the component 11 and the remainder of the component 15 are sufficiently mixed to dissolve.
Step 6: The solution obtained in Step 5 is added to the solution obtained in Step 4 being stirred, and the resultant solution is mixed to be homogenized.
Step 7: The solution obtained in Step 6 is added to the emulsion obtained in Step 3 being stirred, and the resultant solution is mixed to be homogenized.
Step 8: The components 12 to 14 are further added to the solution thus obtained, and the resultant solution is mixed to be homogenized.

Advantageous Effects

The product is expected to improve rough skin with anti-inflammatory effect of allantoin, for users with sensitive skin and the like. The product features good stability, smooth feeling during use (application), and low stickiness. Furthermore, the product is expected to provide moisturizing effect and skin protection effect for a long period of time after the application. The product also features excellent transparency.

Formulation Example 4: Beauty Essence (Components)
1. Sodium stearoylglutamate, 0.33 part
2. N-(hexadecyloxy hydroxypropyl)-N-hydroxyethylhexadecanamide, 1.0 part
3. Glycerin, 10.0 parts
4. Glyceryl behenate, 0.3 part
5. Dicapric acid neopentyl glycol, 0.3 part
6. Paraben, 0.2 part
7. Allantoin (or any desirable medicinal properties), 0.4 part
8. Dipropylene glycol, 5.0 parts
9. Silicone compound No. 7, 1.0 part
10. Acrylic acid-methacrylic acid alkyl copolymer, 0.1 part
11. Carbomer, 0.1 part
12. Sodium hyaluronate, 0.2 part
13. Carrageenan, 0.3 part
14. Perfume, appropriate amount
15. Ion-exchanged water, 80.77 parts
[Method of Production]
Step 1: The components 1 to 6 and a part of the component 15 are mixed and then are heated at 80 to 90° C. to be dissolved.
Step 2: The component 7 is mixed with a part of the component 15 and are heated at 80 to 90° C. to dissolved.

Step 3: The mixture solution obtained in Step 2, heated to 80° C. or higher, is added to the solution obtained in Step 1 under stirring, and the emulsification process is performed at 80° C. The resultant emulsion is cooled down to a room temperature.

Step 4: In a separate vessel, the component 10 to 13 are mixed with the remainder of the component 15 (approximately 70 parts) to be dissolved.

Step 5: In a separate vessel, the components 8 to 9 and the remainder of the component 14 are sufficiently mixed to dissolve.

Step 6: The emulsion obtained in Step 3 is added to the solution obtained in Step 4 being stirred, and the resultant solution is mixed to be homogenized.

Step 7: The solution obtained in Step 5 is further added to the resultant solution, and the solution is mixed to be homogenized.

Advantageous Effects

The produce is expected to provide beauty/skin beauty effect with an effect of the medicinal components. The product features good stability, smooth feeling during use (application), good skin absorption, and low stickiness. After the application, the product can be expected to provide moisturizing effect, skin protection effect, softening effect, and the like over a long period of time, in addition to the shininess of the skin. The product also features excellent transparency.

Formulation Example 5: Lotion (Components)
1. Polyoxyethylene (60) hardened castor oil, 0.2 part
2. Polyoxyethylene isostearate (50) hardened castor oil, 0.2 part
3. Tri(caprylic acid-capric acid) glycerin, 0.01 part
4. Isotridecyl isononanoate, 0.02 part
5. Propylene glycol dicaprate, 0.01 part
6. Ubiquinone (or any desirable medicinal properties), 0.03 part
7. Paraben, 0.2 part
8. Ethanol, 10.0 parts
9. Silicone compound No. 9, 1.0 part
10. Sodium monohydrogen phosphate, 0.1 part
11. Sodium dihydrogen phosphate, 0.05 part
12. Butylene glycol, 10.0 parts
13. Glycerin, 5.0 parts
14. 90% Lactic acid, 0.2 part
15. Ion-exchanged water, 72.98 parts
[Method of Production]
Step 1: The components 1 to 9 are mixed and heated to 50° C. to uniformly dissolve.
Step 2: The components 10 to 15 are uniformly dissolved.
Step 3: The solution obtained in Step 1 is added to the solution obtained in Step 2 under stirring, and the resultant solution is mixed and homogenized.

Advantageous Effects

The product features excellent transparency and stability. The product is also expected to provide a toner featuring a smooth feeling on touch and low stickiness during use, and providing a medical effect of ubiquinone. The product is further expected to provide moisturizing effect and skin protection effect over a long period of time after the application.

Formulation Example 6: Transparent Shampoo (Components)
1. Sodium polyoxyethylene(2)laurylether sulfate, 11.0 parts
2. Coconut oil fatty acid amidopropylbetaine, 2.5 parts
3. Dipropylene glycol, 0.5 part
4. Diethylene glycol laurate, 1.0 part
5. Isostearyl alcohol, 0.5 part
6. Silicone compound No. 9, 1.0 part
7. Propylene glycol, 5.0 parts
8. Cationized guar gum, 0.2 part
9. Cationized locust bean gum, 0.2 part
10. Salt, 1.0 part
11. Sodium benzoate, 0.3 part
12. Ion-exchanged water, 76.8 parts
[Manufacturing Process]
Step 1: The components 1 to 7 and an appropriate amount of the component 12 are mixed to uniformly dissolve.
Step 2: The components 8 to 11 and the remainder of the component 12 are mixed and stirred to uniformly dissolve.
Step 3: The solution obtained in Step 1 is added to the solution obtained in Step 2 under stirring, and the resultant solution is mixed to be homogenized.

Advantageous Effects

The product features many advantages including excellent transparency, great foaming at the time of use, fine quality of foam (creaminess), smoothness at the time of rinsing (fingers can smoothly run through the hair), and no stiffness of the hair after the use.

Formulation Example 7: Lotion (Components)
1. Butylene glycol, 0.5 part
2. DiPOE(8) (C12-15) alkylether phosphate, 0.3 part
3. POE(60) hardened castor oil, 0.1 part
4. Silicone compound No. 8, 0.05 part
5. N-methyl taurine sodium, 0.01 parts
6. α-olefin oligomer, 0.1 parts
7. Isostearic acid, 0.1 parts
8. Retinol palmitate (or any oil soluble medicinal component), 0.01 parts
9. Ion exchanged water, 0.2 parts
10. Perfume, 0.01 part
11. Glycerin, 2.0 parts
12. Trehalose 3.0 parts
13. L-ascorbic acid 2-glucoside (or any water-soluble medicinal component), 2.0 parts
14. Sodium metaphosphate, 0.05 parts
15. Citric acid, 0.02 parts
16. Sodium citrate, 0.08 parts
17. Potassium hydroxide, 0.39 parts
18. Ion exchanged water, 80.97 parts
19. Ethanol, 10.0 parts
20. Methylparaben, 0.1 parts
[Manufacturing Process]
Step 1: The components 1 to 10 are mixed thoroughly and heated to 40 to 50° C. to be homogenized.
Step 2: The components 11 to 18 are mixed thoroughly and stirred thoroughly to uniformly dissolve.
Step 3: The components 19 to 20 are mixed and stirred thoroughly to uniformly dissolve.
Step 4: The solution obtained in Step 3 is added to the solution obtained in Step 2 being stirred thoroughly, and the resultant solution is mixed to be homogenized.

Step 5: The mixed solution obtained in Step 1 is added to the solution obtained in Step 4 being stirred, and the resultant solution is homogenized.

Advantageous Effects

The product provides moisturizing effect and skin improvement effect for the skin, and is expected to achieve a moisturized state of the skin over a long period of time. The product features low stickiness, as well as smooth coating feeling/excellent penetration feel with good absorbing to the skin at the time of application. The product is also expected to achieve stability of transparency against vibrations during transportation and use, as well as stability against freezing in cold places.

Formulation Example 8: Skin Lotion (Components)
1. Butylene glycol, 0.8 parts
2. POE (15) POP (5) oleyl ether phosphate, 0.4 parts
3. POE (20) behenyl ether, 0.1 parts
4. Silicone compound No. 10, 0.20 parts
5. Isocetyl octanoate, 0.05 parts
6. Retinol (or any oil soluble medicinal component), 0.01 parts
7. Isostearic acid, 0.15 parts
8. Grapefruit oil, 0.01 parts
9. L-arginine, 0.03 parts
10. Ion exchanged water, 0.5 parts
11. Poly ethylene glycol 400, 5.0 parts
12. Methylparaben, 0.05 parts
13. Phenoxy ethanol, 0.4 parts
14. Ion exchanged water, 92.05 parts
15. Korean carrot extract, 0.1 parts
16. Dipotassium glycyrrhizinate (or any water-soluble medicinal component), 0.05 parts
17. Citric acid, 0.02 parts
18. Sodium citrate, 0.08 parts
[Manufacturing Process]
Step 1: The components 1 to 8 are mixed thoroughly and heated to 40 to 50° C. to be homogenized.
Step 2: The components 9 and 10 are mixed and well stirred to uniformly dissolve.
Step 3: The solution obtained in Step 2 is added to the mixture solution obtained in Step 1 heated to 40 to 50° C. and stirred, and the resultant solution was mixed to be homogenized.
Step 4: The components 11 to 13 are mixed, heated to 40 to 50° C., and stirred to uniformly dissolve.
Step 5: The components 14 to 18 are mixed and well stirred to uniformly dissolve.
Step 6: The solution obtained in Step 4 is added to the solution obtained in Step 5 being stirred, and the resultant solution was mixed to dissolve.
Step 7: The mixture solution obtained in Step 3 is added to the solution obtained in Step 6 being stirred, and the resultant solution is homogenized.

Advantageous Effects

The product is expected to provide skin improvement effect with anti-inflammatory effect and anti-allergic effect provided by the medicinal component. The product is expected to provide a wet state of the skin as well as moisturizing effect and skin protection effect over a long period of time. The product features low stickiness, as well as smooth coating feeling/excellent penetration feel with good absorbing to the skin at the time of application. The product is also expected to achieve stability of transparency against vibrations during transportation and use, as well as stability against freezing in cold places.

Formulation Example 9: Face Lotion (Components)
1. Tranexamic acid (or any water-soluble medicinal component), 1.0 parts
2. Potassium 4-methoxysalicylate (or any water-soluble medicinal component), 2.0 parts
3. Glycerin, 8.0 parts
4. Hyaluronic acid, 0.01 parts
5. Carboxymethyl cellulose, 0.05 parts
6. Citric acid, appropriate amount
7. Sodium citrate, appropriate amount
8. Sodium metaphosphate, appropriate amount
9. Sodium pyrosulfite, appropriate amount
10. Ion-exchanged water, balance
11. Silicone compound No. 9, 0.5 part
12. Dipropylene glycol, 5.0 parts
13. 90% Lactic acid, 0.1 part
14. Ion-exchanged water, 4.5 parts
15. PEG/PPG-17/4 dimethylether, 3.0 parts
16. PPG-13 decyl tetradeceth-24, 0.2 parts
17. Phenoxy ethanol, appropriate amount
18. Perfume, appropriate amount
[Method of Production]
Step 1: The components 11 to 14 are mixed and stirred thoroughly to uniformly dissolve.
Step 2: The components 15 to 18 are mixed and stirred thoroughly to uniformly dissolve.
Step 3: The components 1 to 10 are mixed and stirred thoroughly to uniformly dissolve.
Step 4: The solution obtained in Step 1 is added to the solution obtained in Step 3 being stirred, and the resultant solution is homogenized.
Step 5: The solution obtained in Step 2 is added to the solution obtained in Step 4 being stirred, and the resultant solution is homogenized.

Advantageous Effects

The product is expected to provide a rough skin improvement with the medicinal component and whitening effect. Stickiness and squeakiness attributable to the tranexamic acid compounded is suppressed. The product is further expected to provide rich and smooth coating feel with good skin absorption, as well as moisturizing effect, skin protection effect, softening effect maintained for a long period of time.

Formulation Example 10: Essence (Components)
1. Tranexamic acid methylamide hydrochloride (or any water-soluble medicinal component), 1.0 parts
2. Ascorbic acid glucoside (or any water-soluble medicinal component), 2.0 parts
3. Dipotassium glycyrrhizinate (or any water-soluble medicinal component), 0.05 parts
4. Glycerin, 10.0 parts
5. Maltitol, 3.0 parts
6. Xylitol, 2.0 parts
7. Acetylated hyaluronic acid, 0.03 parts 8. Carboxymethyl cellulose, 1.5 parts
9. Ion-exchanged water, balance
10. Citric acid, appropriate amount
11. Sodium citrate, appropriate amount
12. Edetate, appropriate amount
13. Silicone compound No. 8, 0.1 part
14. Propylene glycol, 5.0 parts
15. Aspartic acid, 0.03 parts
16. Ion-exchanged water, 5.0 parts
17. PEG/PPG-14/7 dimethylether, 1.5 parts
18. PEG-20 isostearate glyceryl, 0.1 parts
19. Perfume, appropriate amount
20. Phenoxyethanol, appropriate amount (Method of Production)

Step 1: The components 15 and 16 are mixed and heated to 60° C. to uniformly dissolve.
Step 2: The components 13 to 14 are mixed and stirred thoroughly to uniformly dissolve.
Step 3: The solution obtained in Step 1 and the solution obtained in Step 2 are mixed and stirred thoroughly to uniformly dissolve.
Step 4: The components 17 to 20 are mixed and stirred thoroughly to uniformly dissolve.
Step 5: The components 1 to 12 are mixed and stirred thoroughly to uniformly dissolve.
Step 6: The solution obtained in Step 3 is added to the solution obtained in Step 5 being stirred, and the resultant solution is homogenized.
Step 7: The solution obtained in Step 4 is added to the mixture solution obtained in Step 6 being stirred, the resultant solution is homogenized.

Advantageous Effects

The product is expected to provide rough skin improvement effect and anti-inflammatory effect with the medicinal component, as well as whitening effect. The product is further expected to provide smooth coating feel with good skin absorption, as well as moisturizing effect, skin protection effect, softening effect maintained for a long period of time, with stickiness and squeakiness reduced. The product is designed to be rather thick (within an acceptable range) as a toner, but is not slimy and thus can be suitable applied and spread on the skin.

Formulation Example 11: UV Protection Lotion (Components)
1. Glycerin, 3.0 parts
2. Citric acid, 0.05 parts
3. Sodium dihydrogen phosphate, 0.05 part
4. Ascorbyl sodium phosphate (or any water-soluble medicinal component), 2.0 parts
5. Cetyl tranexamate hydrochloride, 1.0 parts
6. Ethanol, 5.0 parts
7. Dipropylene glycol, 2.0 parts
8. Ion-exchanged water, 75.62 parts
9. Silicone compound No. 9, 0.2 part
10. Propylene glycol, 2.0 parts
11. Glutamic acid, 0.07 part
12. Ion-exchanged water, 7.0 parts
13. POE(14)POP(7) dimethylether, 1.0 part
14. POE (30) phytosterol, 0.4 parts
15. Phenoxyethanol, 0.5 part
16. Bis-ethylhexyloxyphenol methoxyphenyl triazine (or any UV protection component), 0.1 parts
17. Perfume, 0.01 part (Method of Production)

Step 1: The components 11 are 12 mixed and heated to 60° C. to uniformly dissolve.
Step 2: The components 9 and 10 are mixed and stirred thoroughly to uniformly dissolve.
Step 3: The solution obtained in Step 1 and the solution obtained in Step 2 are mixed and stirred thoroughly to uniformly dissolve.
Step 4: The components 13 to 16 are mixed, heated to 60° C. and stirred, to be homogenized. Then, the resultant solution is cooled down to 30° C., and the component 17 is added to the solution.
Step 5: The components 1 to 8 are mixed and stirred thoroughly to uniformly dissolve.
Step 6: The solution obtained in Step 3 is added to the solution obtained in Step 5 being stirred, and the resultant solution is homogenized.
Step 7: The solution obtained in Step 4 is added to the mixture solution obtained in Step 6 being stirred, the resultant solution is homogenized.

Advantageous Effects

The product is expected to provide UV protection effect as well as the rough skin improvement, the anti-inflammatory effect, the whitening effect, and the like due to the medicinal component. The product further features excellent stability and transparency. The product involves low stickiness, and provides smooth coating feel with good skin absorption, and moisturizing effect and skin protection effect over a long period of time. The product can also be used as hair lotion, and thus can be expected to provide these effects to the hair and the scallop.

Formulation Example 12: Whitening Cream (Components)
1. Stearic acid, 14.0 parts
2. Setanol, 3.0 parts
3. Sorbitan monostearate, 2.0 parts
4. Sorbitan monostearic acid POE (20), 1.5 parts
5. Squalane, 2.0 parts
6. Propyl paraben, 0.2 parts
7. Perfume, 0.01 parts
8. Glycerin, 2.0 parts
9. Potassium hydroxide, 0.2 parts
10. β-arbutin (or any water-soluble medicinal component), 1.0 parts
11. Acetylated hyaluronic acid, 2.0 parts
12. Ion-exchanged water, balance
13. Silicone compound No. 10, 0.8 part
14. Propylene glycol, 8.0 parts (Method of Production)

Step 1: The components 1 to 6 are mixed, heated to 70° C., and stirred to uniformly dissolve.
Step 2: The components 8 to 12 are mixed, heated to 70° C., and stirred to uniformly dissolve.
Step 3: The components 13 and 14 are mixed thoroughly to dissolve.
Step 4: The solution obtained in Step 1 and the solution obtained in Step 2 are mixed and emulsified by a homo mixer at 70° C.
Step 5: The solution obtained in Step 3 is added to the emulsion obtained in Step 4, and the emulsification is further performed at 70° C.

Step 6: The resultant solution is cooled down to a room temperature while being slowly stirred, and the component 7 is added to and mixed with the resultant solution to be homogenized.

Advantageous Effects

With the combination of arbutin and acetylated hyaluronic acid, the promotes percutaneous absorption and whitening effect of arubutin and the like can be expected to be obtained. Furthermore, the product can provide good skin absorption with small stickiness, as well as moisturizing effect, coating feel and skin protection effect maintained for a long period of time.

Formulation Example 13: Whitening Lotion (Components)
1. α-arbutin, 3.0 parts
2. Acetylated hyaluronic acid, 0.2 parts
3. Citric acid, 0.2 parts
4. Sodium citrate, 0.8 parts
5. Sodium diethylenetriaminepentaacetate, 0.2 parts
6. Hydroxypropyl β cyclodextrin, 1.0 parts
7. Glycerin, 5.0 parts
8. Dipropylene glycol, 5.0 parts
9. Ion exchanged water, balance
10. Ethanol, 10.0 parts
11. POE (60) hardened castor oil, 1.0 parts
12. Methylparaben, 0.15 parts
13. Silicone compound No. 9, 1.0 parts
14. 90% Lactic acid, 0.2 part
15. Perfume, 0.01 parts
(Method of Production)
Step 1: The components 1 to 9 are mixed thoroughly to uniformly dissolve.
Step 2: The components 10 to 15 are mixed to uniformly dissolve.
Step 3: The solution obtained in Step 2 is added to the solution obtained in Step 1, and the resultant solution was agitated thoroughly to be homogenized.

Advantageous Effects

With the combination of arbutin and acetylated hyaluronic acid, the promotes percutaneous absorption and whitening effect of arubutin and the like can be expected to be obtained. Furthermore, the product can provide good skin absorption with small stickiness, and slippery smooth coating feel, as well as moisturizing effect and skin protection effect maintained for a long period of time.

Formulation Example 14

(Components)
1. POE (40) sorbitan monostearate, 2.0 parts
2. Self-emulsifying glyceryl monostearate, 5.0 parts
3. Stearic acid, 5.0 parts
4. Behenyl alcohol, 0.5 parts
5. Squalane, 14.5 parts
6. Coenzyme Q, 10 0.5 parts
7. Cetyl 2-ethylhexanoate, 5.0 parts
8. Ocopherol acetate, 0.1 parts
9. Methylparaben, 0.1 parts
10. Kojic acid distearate (or any oil soluble medicinal component), 0.1 parts
11. *Hamamelis* extract, 0.1 parts
12. Licorice extract (or any water-soluble medicinal component), 1.0 parts
13. Xanthan gum (2% water solution), 7.0 parts
14. Sodium pyrrolidone carboxylate, 0.1 parts
15. Ion exchanged water, balance
16. Dipropylene glycol, 5.0 parts
17. Silicone compound No. 9, 0.5 parts
18. 90% lactic acid, 0.1 parts
19. Ion-exchanged water, 5.0 parts
20. Perfume, appropriate amount
(Method of production)
Step 1: The components 16 to 19 are mixed thoroughly to uniformly dissolve.
Step 2: The components 11 to 15 are mixed and heated to 70° C. to dissolve.
Step 3: The components 1 to 10 are thermally mixed and heated to 70° C. to dissolve.
Step 4: The solution obtained in Step 3 is mixed to the solution obtained in Step 2, and the resultant solution is uniformly emulsified at 70° C.
Step 5: The solution obtained in Step 1 is added to the emulsion obtained in Step 4 and the resultant solution is further emulsified.
Step 6: The emulsion is cooled down to a room temperature, the component 20 is mixed thereto, and the resultant emulsion is mixed to be homogenized.

Advantageous Effects

The product is expected to provide rough skin improvement effect and anti-inflammatory effect with the medicinal component, as well as whitening effect. This rich texture cream can be softly applied to the skin with no stickiness, and can be quickly absorbed in the skin to be comfortably used. The moisturizing effect, the skin protection effect, and the like can be expected for a long period of time after the application.

Formulation Example 15: Whitening Essence (Components)
1. Ion-exchanged water, balance
2. Glycerin, 5.0 parts
3. Butylene glycol, 6.0 parts
4. PPG-10 methyl glucose ether, 0.80 parts
5. PPG-120 methyl glucose dioleate, 0.10 parts
6. Methyl glucoses-10, 1.50 parts
7. EDTA disodium, 0.05 parts
8. Preservative, 0.60 parts
9. PEG-40 hydrogenated castor oil, 0.20 parts
10. Poly sorbate 80, 0.10 parts
11. PPG-8 Cetece-20, 0.10 parts
12. Natural vitamin E, 0.01 parts
13. Perfume, 0.05 parts
14. Ion-exchanged water, 10.0 parts
15. Sodium citrate, 0.10 parts
16. Citric acid, 0.13 parts
17. Kojic acid (or any water-soluble medicinal component), 0.50 parts
18. Triisopropanolamine, 0.46 parts
19. Phenylbenzimidazole sulfonic acid, 2.1 parts
20. Ethanol, 8.0 parts
21. Silicone compound No. 8, 0.1 parts
22. 90% lactic acid, 0.03 parts (Method of Production)
Step 1: The components 1 to 8 are mixed and heated to 80° C. to be homogenized, and then is held at 60° C.
Step 2: The components 9 to 13 are mixed and heated to 60° C. to be homogenized.
Step 3: The mixture solution obtained in Step 2 is added to the mixture solution obtained in Step 1, mixed thoroughly to be homogenized.
Step 4: The components 20 to 22 are mixed thoroughly to dissolve.
Step 5: The components 14 to 19 are mixed thoroughly to dissolve.
Step 6: The solution obtained in Step 4 is added to the mixture solution obtained in Step 3, mixed thoroughly to be homogenized.
Step 7: The solution obtained in Step 5 is added to the mixture solution obtained in Step 6 at a room temperature, mixed thoroughly to be homogenized.

Advantageous Effects

The product is expected to provide UV protection effect as well as the rough skin improvement, the anti-inflammatory effect, the whitening effect, and the like due to the medicinal component. The product further features excellent stability and transparency. The moisturizing effect, the skin protection effect, and the like can be expected for a long period of time after the application.

Formulation Example 16: Facial Mask (Components)
1. Polyvinyl alcohol, 12.0 parts
2. Methylcellulose, 0.1 parts
3. Glycerin, 3.0 parts
4. Dipropylene glycol, 5.0 parts
5. Glycosyl trehalose, 2.0 parts
6. Hydrolyzed hydrogenated starch, 1.0 parts
7. Grapefruit seed extract, 1.0 parts
8. *Portulaca oleracea* extract, 0.5 parts
9. Sodium pyrrolidone carboxylate, 0.3 parts
10. Ion exchanged, water balance
11. Perfume, appropriate amount
12. Preservative, appropriate amount
13. Glyceryl tri-2-ethylhexanoate, 0.1 parts
14. Monooleic acid POE (20) sorbitan, 1.0 parts
15. Ethyl alcohol 13.0 parts
16. Silicone compound No. 9, 1.0 parts
17. 90% lactic acid 0.2 parts
(Method of Production)
Step 1: The components 1 to 10 are mixed, heated to 80° C., and dissolved. The resultant solution is cooled down to a room temperature.
Step 2: The components 11 to 17 are mixed and stirred thoroughly to dissolve.
Step 3: The solution obtained in Step 2 is added to the solution obtained in Step 1, and the resultant solution is homogenized.

Advantageous Effects

The facial mask thus obtained can provide an appropriate amount of tension when applied to the skin. The skin after the pack is peeled is expected to have no stickiness, and effectively give an impression of fresh and rich moisturizing feeling. The product further features excellent whitening effect as well as stability.

Formulation Example 17: Whitening Essence (Components)
1. Neopentyl glycol dicaprate, 6.0 parts
2. Cetanol, 0.3 parts
3. Stearyl alcohol, 0.2 parts
4. N-stearoylglutamic acid, 5.0 parts
5. Chamomile extract (squalane solution, chamomile extract (solid content) 0.4%), 2.0 parts
6. Perfume, 0.035 parts
7. Glycerin, 5.0 parts
8. Ion-exchanged water, balance
9. Acrylic acid/methacrylic acid alkyl copolymer, 0.35 parts
10. Polyoxyethylene hydrogenated castor oil, 0.3 parts
11. Thickening polysaccharide, 2.0 parts
12. Tranexamic acid (or any water-soluble medicinal component), 2.0 parts
13. Ethanol, 6.0 parts
14. Silicone compound No. 10, 0.6 parts
15. Methylparaben, 0.3 parts
16. Ion exchanged water, 4.0 parts
17. Potassium hydroxide, 0.175 parts
18. Ion-exchanged water, 3.5 parts
(Method of Production)
Step 1: The components 1 to 6 are mixed and heated to 80° C. to dissolve.
Step 2: The components 7 to 12 are mixed and heated to 80° C. to dissolve.
Step 3: The components 17 to 18 are mixed to dissolve. The resultant solution is added to the solution obtained in Step 2, mixed at 80° C., and the resultant solution is homogenized.
Step 4: The solution obtained in Step 1 is added to the solution obtained in Step 3 and mixed thoroughly. The resultant solution is homogeneously emulsified with a homo mixer. The resultant emulsion is cooled down to and held at 50° C.
Step 5: The components 13 to 16 are mixed and stirred thoroughly to dissolve.
Step 6: The solution obtained in Step 5 is added to the emulsion obtained in Step 4. The resultant solution is further processed by the homo mixer, The resultant emulsion is cooled down to a room temperature.

Advantageous Effects

Rough skin improvement, anti-inflammatory effect, convergence, whitening effect, and the like are expected to be obtained with the medicinal component. This essence has a thick and dense texture, but can also provide smooth application feel, good spreading performance, and appropriate coating feel, with stickiness suppressed. The moisturizing effect can also be expected over a long period of time.

Formulation Example 18: Skin Lightening Emulsion (Components)
1. 1,2-hexanediol, 3.0 parts
2. 1,3-butanediol, 5.0 parts
3. Glycerin, 2.0 parts
4. Chenoxy ethanol 0.5 parts
5. Chamomile extract: BG solution (or any water-soluble medicinal component), 2.0 parts
6. silicone compound No. 9, 0.5 parts
7. 90% lactic acid, 0.1 parts
8. Polyoxyethylene hydrogenated castor oil, 0.1 parts
9. Ethanol, 5.0 parts 10. 4-n-butyl resorcinol 0.3 parts
11. Polymethacryloyl lysine, 0.1 parts
12. Polymethacryloyloxyethyl phosphorylcholine, 0.1 parts
13. Polyglucosyloxyethyl methacrylate, 0.1 parts
14. ion exchanged water, balance
(Method of Production)
Step 1: The component 1 to 10 are mixed thoroughly to uniformly dissolve.
Step 2: The component 11 to 14 are mixed thoroughly to uniformly dissolve.
Step 3: The solution obtained in Step 1 is added to the solution obtained in Step 2 being stirred, and the solution is homogenized.

Advantageous Effects

Rough skin improvement, anti-inflammatory effect, convergence, whitening effect, skin lightening effect, and the like are expected to be obtained with the medicinal component Formulation Example 19

(Components)
1. Squalane, 3.0 parts
2. Glyceryl 2-ethylhexanoate, 2.0 parts
3. Grape seed oil, 1.0 parts
4. Ascorbyl tetra 2-hexyldecanoate (or any oil soluble medicinal component), 3.0 parts
5. Cetanol, 1.5 parts
6. Stearyl alcohol, 0.5 parts
7. Cholesterol, 0.2 parts
8. Decaglyceryl myristate, 3.0 parts
9. Hydrogenated lecithin, 1.0 parts
10. Beeswax, 0.3 parts
11. Butylene glycol, 2.0 parts
12. Glycerin, 5.0 parts
13. Poly ethylene glycol (PEG600), 3.0 parts
14. Ellagic acid, 1.0 parts
15. Hyaluronic acid, 0.05 parts
16. Paraoxybenzoic acid ester, appropriate amount
17. Edetate disodium, appropriate amount
18. Hydroxyethyl cellulose, appropriate amount
19. Xanthan gum, appropriate amount
20. Ion exchanged water, balance
21. Dipropylene glycol, 5.0 parts
22. Dilicone compound No. 9, 0.5 parts
23. Glycolic acid, 2.1 parts
(Method of Production)
Step 1: The components 1 to 10 are mixed and heated to 80° C. to uniformly dissolve.
Step 2: The components 11 to 20 are mixed and heated to 80° C. to uniformly dissolve.
Step 3: The component 21 to 23 are mixed thoroughly to dissolve.
Step 4: The solution obtained in Step 1 is added to the solution obtained in Step 2 being stirred at 80° C., and the resultant solution is mixed thoroughly to be homogenized. Then, the solution is cooled down to or below 40° C.
Step 5: The solution obtained in Step 3 is added to the mixed solution obtained in Step 4, mixed thoroughly, and homogenized.

Advantageous Effects

Rough skin improvement, anti-inflammatory effect, convergence, whitening effect, skin lightening effect, and the like are expected to be obtained with the medicinal component The productivity also features excellent stability.

Formulation Example 20

(Components)
1. liposome suspension (containing 0.5% of linoleic acid) 10.0 parts
2. glycerin 1.0 parts
3. squalane (olive derived) 2.0 parts
4. olive oil 1.5 parts
5. jojoba oil 1.3 parts
6. pentaerythrityl tetraoctanoate 1.0 parts
7. polyoxyethylene oleyl ether 0.8 parts
8. silicone compound No. 7, 0.5 parts
9. caprylyl methicone 1.0 parts
10. methylparaben 0.1 parts
11. carboxyvinyl polymer 0.2 parts
12. xanthan gum 0.05 parts
13. Purified water balance
14. 5% aqueous potassium hydroxide solution appropriate amount (adjusted to pH of 6.5)
(Method of Production)
Step 1: The components 1 to 10 are mixed thoroughly and homogenized.
Step 2: The components 11 to 13 are mixed thoroughly to dissolve. An appropriate amount of the component 14 is added, and the resultant solution is mixed thoroughly to be homogenized.
Step 3: The mixture solution obtained in Step 1 is added to the mixture solution obtained in Step 2 being stirred. The solutions are mixed thoroughly to be homogenized.

Advantageous Effects

Skin care effects such as anti-inflammatory effect, whitening effect, and antiaging effect are expected to be obtained with linoleic acid. The productivity also features excellent stability. A smooth and slippery coating feel with excellent spreading performance, as well good skin absorption and penetration performance are expected to be obtained.

Formulation Example 21

(Components)
1. Liposome suspension (containing 0.5% of linoleic acid), 10.0 parts
2. Squalane (olive derived), 2.0 parts
3. Olive oil, 1.5 parts
4. Jojoba oil, 1.3 parts
5. Polyoxyethylene (20) sorbitan monooleate, 1.0 parts
6. Isotridecyl isononanoate, 1.0
7. Dibutylhydroxytoluene, 0.02 parts
8. Cholesterol, 1.0 parts
9. Paraben, 0.2 parts
10. Acrylic acid/alkyl methacrylate copolymer, 0.35 parts
11. Glycerin, 1.0 parts
12. PEG400, 0.5 parts
13. Ion exchanged water, balance
14. 10% potassium hydroxide water solution, 1.75 parts
15. Dipropylene glycol, 5.0 parts
16. Silicone compound No. 9, 0.6 parts
17. Glycolic acid, 0.1 parts
18. Ion-exchanged water, 5.0 parts (Method of Production)
Step 1: The components 1 to 9 are mixed thoroughly and heated to 40° C. to be homogenized.
Step 2: The components 10 to 13 are mixed thoroughly to dissolve. Then, the component 14 is added to be mixed thoroughly to be homogenized.
Step 3: The components 15 to 18 are mixed thoroughly to dissolve.
Step 4: The mixture solution obtained in Step 1 is added to the mixture solution obtained in Step 2 being stirred, and mixed thoroughly to be homogenized.
Step 5: Furthermore, the solution obtained in Step 3 is added to the mixed solution obtained in
Step 4, mixed thoroughly to be homogenized.

Skin care effects such as anti-inflammatory effect, whitening effect, and anti-aging effect are expected to be obtained with linoleic acid. The productivity also features excellent stability. A smooth and slippery coating feel with excellent spreading performance, as well good skin absorption and penetration performance are expected to be obtained.

Formulation Example 22: Body Care Shampoo (Components)
1. Ion exchanged water, balance
2. Propylene glycol, 10.0 parts
3. Lauramidopropyl betaine, 4.0 parts
4. Sulfosuccinic acid (C12-14) palace—2Na, 3.0 parts
5. Glycerin, 2.0 parts
6. Sorbitol, 1.5 parts
7. Cocoyl methyl taurine sodium, 1.0 parts
8. Sodium lauraminopropionate, 1.0 parts
9. Silicone compound No. 9, 0.5 parts
10. PCA-Na, 0.3 parts
11. Honey, 0.3 parts
12. Perfume, appropriate amount
13. Sodium benzoate, 0.3 parts
14. 90% lactic acid, appropriate amount (adjusted to pH 6.5 to 7.5)

(Method of Production)
Step 1: The components 2 to 13 and an appropriate amount of the compound 1 are mixed thoroughly to dissolve.
Step 2: The remainder of the component 1 is mixed into the solution obtained in Step 1, and a uniform solution is obtained.
Step 3: The component 14 is added to the solution obtained in Step 2, mixed thoroughly to be homogenized.

Advantageous Effects

The product obtained features excellent transparency, and is expected to provide excellent effects including rich at the time of use and fine foam quality (creaminess). The product provides smoothness to the skin at the time of rinsing, and prevents the skin from drying after the use, and can be expected to provide moisturizing and skincare effect for a long period of time.

The invention claimed is:
1. An organopolysiloxane represented by the following general formula (1) or acid-neutralized salt thereof:

wherein $R^1$ represents a monovalent organic group not having a nitrogen atom or a polyoxyalkylene structure or any reactive structure to radical polymerization with the proviso that $R^2$, L and Q are excluded therefrom, a hydrogen atom, or a hydroxyl group;
$R^2$ represents a halogen-substituted or non-substituted, and linear or branched monovalent hydrocarbon group having 6 to 30 carbon atoms;
$L^1$ represents a silylalkyl group having a siloxane dendron structure, in the case of i=1, represented by the following general formula (3)

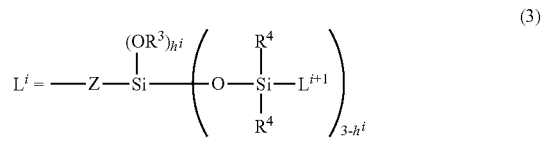

wherein $R^3$ independently represents a substituted or non-substituted, and linear or branched monovalent hydrocarbon group having 1 to 30 carbon atoms, $R^4$ independently represents an alkyl group having 1 to 6 carbon atoms or a phenyl group, Z is a divalent organic group, i specifies a number of generations of said silylalkyl group, represented by $L^i$, in the case in which a number of generations of said silylalkyl group, which is a number of repetitions of said silylalkyl group, is k, i is an integer ranging from 1 to k, and a number of generations k is an integer ranging from 1 to 10, $L^{i+1}$ is said silylalkyl group in the case of i<k, and $L^{i+1}$ is $R^4$ in the case of i=k, and $h^i$ is a number ranging from 0 to 3, or
an organosiloxane group in the form of a chain, represented by the following general formula (2-1)

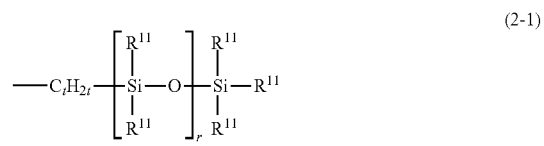

wherein $R^{11}$ is independently a substituted or non-substituted monovalent hydrocarbon group having 1 to 30 carbon atoms, a hydroxyl group or a hydrogen atom, at least one of $R^{11}$ is said monovalent hydrocarbon group; t is a number ranging from 2 to 10; and r is a number ranging from 1 to 500, or represented by the following general formula (2-2)

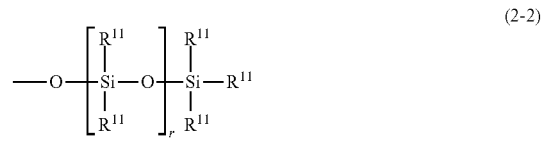

wherein $R^{11}$ and r are the same as defined above;
Q represents a side-chain bonded hydrophilic group having a tertiary-amine structure and represented by following general formula:

wherein q is a number ranging from 1 to 6, each of $R^{Q1}$ and $R^{Q2}$ is independently a halogen-substituted or non-substituted monovalent hydrocarbon group or an alkanol group, at least one of $R^{Q1}$ and $R^{Q2}$ has a hydroxyl group, provided the total number of hydroxyl groups in $R^{Q1}$ and $R^{Q2}$ is at most three (3), and any of $R^{Q1}$ and $R^{Q2}$ does not have a nitrogen atom in the group; and each of a, b, c, and d is independently a number having the following range: $1.0 \leq a \leq 2.5$, $0 \leq b \leq 1.5$, $0 \leq c \leq 1.5$, and $0.0001 \leq d \leq 1.5$;

and wherein the number of Si atoms ranges from 4 to 1000.

2. The organopolysiloxane or acid-neutralized salt thereof according to claim 1, which is represented by the following structural formula (1-1)

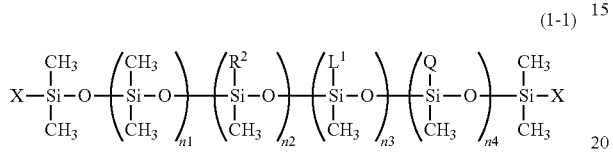

wherein $R^2$, $L^1$, and Q are independently the same as defined above,

X is a group selected from the group consisting of a methyl group, monoglycerol group, diglycerol group, triglycerol group, polyglycerol group or $R^2$, and $L^1$ group;

n1+n2+n3+n4 is a number ranging from 2 to 1,000, n1 is a number ranging from 1 to 999, n2 is a number ranging from 0 to 998, n3 is a number ranging from 0 to 998, and n4 is a number ranging from 1 to 999.

3. The organopolysiloxane or acid-neutralized salt thereof according to claim 1, wherein Q is a hydrophilic group having a tertiary-amine structure and represented by the following general formula (4-1)

wherein q is a number ranging from 1 to 6, and each $R^{Q3}$ independently represents a linear or branched C1-C10 alkanol group having one alcoholic hydroxyl group.

4. The organopolysiloxane or acid-neutralized salt thereof according to claim 1, wherein Q is a hydrophilic group having a tertiary-amine structure and represented by the following general formula (4-2)

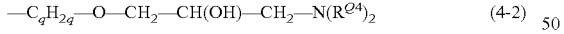

wherein q is a number ranging from 1 to 6, and each $R^{Q4}$ independently represents —$CH_2$—$CH(CH_3)$—OH or —$CH_2$—$CH_2$—OH.

5. The organopolysiloxane or acid-neutralized salt thereof according to claim 1, which further has at least one group selected from $R^2$ and $L^1$ groups.

6. A surfactant or dispersant comprising the organopolysiloxane or acid-neutralized salt thereof according to claim 1.

7. An oil agent comprising the organopolysiloxane or acid-neutralized salt thereof according to claim 1.

8. A thickening agent comprising the organopolysiloxane or acid-neutralized salt thereof according to claim 1.

9. A cosmetic raw material comprising the organopolysiloxane or acid-neutralized salt thereof according to claim 1.

10. A composition comprising:
(A) the organopolysiloxane or acid-neutralized salt thereof according to claim 1; and
(B) at least one oil agent, which is in the form of a liquid at 5 to 100° C., and is selected from the group consisting of a silicone oil, a non-polar organic compound, and a low-polar compound.

11. The composition according to claim 10, further comprising:
(C) water and/or at least one type of alcohol selected from the group consisting of lower alcohols and polyhydric alcohols.

12. A water-based composition comprising:
(A') an acid-neutralized product of the organopolysiloxane according to claim 1, wherein the acid of the acid-neutralized product is at least one type of acid selected from the group consisting of carboxylic acids, amino acids, and inorganic acids.

13. A cosmetic comprising the organopolysiloxane or acid-neutralized salt thereof according to claim 1.

14. A preparation for external use comprising the organopolysiloxane or acid-neutralized salt thereof according to claim 1.

15. A manufacturing process of the organopolysiloxane or acid-neutralized salt thereof as recited in claim 1, comprising the steps of:
(I) reacting organohydrogen polysiloxane with an epoxy compound having an unsaturated hydrocarbon group;
(II) removing unreacted epoxy compound having an unsaturated hydrocarbon group from the system following said step (I);
(III) processing ring-opening reaction between an epoxy functional group and a secondary amine compound having a hydroxyl group following said step (II); and
(IV) optionally, removing unreacted secondary amine compound having a hydroxyl group from the system following said step (III).

16. A manufacturing process of the organopolysiloxane or acid-neutralized salt thereof as recited in claim 1, comprising the steps of:
(I) obtaining an intermediate by processing ring-opening reaction between an epoxy compound having an unsaturated hydrocarbon group and a secondary amine compound having a hydroxyl group;
(II) removing unreacted raw materials from the system following said step (I); and
(III) reacting the intermediate with organohydrogen polysiloxane following said step (II).

* * * * *